United States Patent
Fu et al.

(10) Patent No.: US 12,077,506 B2
(45) Date of Patent: Sep. 3, 2024

(54) INDANE DERIVATIVES AS HYPOXIA INDUCIBLE FACTOR-2(α) INHIBITORS

(71) Applicant: NiKang Therapeutics, Inc., Wilmington, DE (US)

(72) Inventors: Jiping Fu, Danville, CA (US); Yan Lou, Dallas, TX (US); Yigang He, Newark, DE (US)

(73) Assignee: NiKang Therapeutics, Inc., Wilmington, DE (US)

( * ) Notice: Subject to any disclaimer, the term of this patent is extended or adjusted under 35 U.S.C. 154(b) by 590 days.

(21) Appl. No.: 17/286,818

(22) PCT Filed: Oct. 16, 2019

(86) PCT No.: PCT/US2019/056555
§ 371 (c)(1),
(2) Date: Apr. 19, 2021

(87) PCT Pub. No.: WO2020/081695
PCT Pub. Date: Apr. 23, 2020

(65) Prior Publication Data
US 2021/0380536 A1    Dec. 9, 2021

(51) Int. Cl.
C07D 221/04    (2006.01)
A61K 45/06     (2006.01)
C07C 43/295    (2006.01)
C07C 255/54    (2006.01)
C07D 213/65    (2006.01)
C07D 213/85    (2006.01)

(52) U.S. Cl.
CPC ............ C07D 221/04 (2013.01); A61K 45/06 (2013.01); C07C 43/295 (2013.01); C07C 255/54 (2013.01); C07D 213/65 (2013.01); C07D 213/85 (2013.01); C07B 2200/05 (2013.01)

(58) Field of Classification Search
CPC .. C07D 221/04; C07D 213/65; C07D 213/85; A61K 45/06; C07C 255/54
See application file for complete search history.

(56) References Cited

U.S. PATENT DOCUMENTS

| | | |
|---|---|---|
| 6,133,279 A | 10/2000 | Cynshi et al. |
| 6,262,087 B1 | 7/2001 | Perregaard et al. |
| 6,417,418 B2 | 7/2002 | Santi et al. |
| 9,908,845 B2 | 3/2018 | Dixon et al. |
| 10,098,878 B2 | 10/2018 | Bruick et al. |
| 10,155,726 B2 | 12/2018 | Wehn et al. |
| 10,278,942 B2 | 5/2019 | Josey et al. |
| 2016/0362390 A1 | 12/2016 | Wehn et al. |
| 2017/0217892 A1 | 8/2017 | Dixon et al. |
| 2017/0304300 A1 | 10/2017 | Bruick et al. |
| 2018/0148413 A1* | 5/2018 | Wehn ..................... A61K 45/06 |
| 2019/0048421 A1 | 2/2019 | Kim et al. |
| 2019/0282535 A1 | 9/2019 | Josey et al. |
| 2020/0361855 A1 | 11/2020 | Fu et al. |
| 2021/0246102 A1 | 8/2021 | Fu et al. |
| 2021/0347729 A1 | 11/2021 | Fu et al. |

FOREIGN PATENT DOCUMENTS

| | | |
|---|---|---|
| WO | WO 2006/094292 A2 | 9/2006 |
| WO | WO 2015/035223 A1 | 3/2015 |
| WO | WO 2015/095048 A1 | 6/2015 |
| WO | WO 2016/144825 A1 | 9/2016 |
| WO | WO 2016/145045 A1 | 9/2016 |
| WO | WO 2017/053192 A1 | 3/2017 |
| WO | WO 2018/031680 A1 | 2/2018 |
| WO | WO 2019/191227 A1 | 10/2019 |
| WO | WO 2020/055883 A1 | 3/2020 |
| WO | WO 2020/214853 A1 | 10/2020 |
| WO | WO 2021/016280 A1 | 1/2021 |

OTHER PUBLICATIONS

Murugesan et al. Targeting HIF-2 as therapy for advanced cancers, Drug Discovery Today, 23, 1444-1451. (Year: 2018).*
Luo et al. Principles of Cancer Therapy: Oncogene and Non-oncogene Addiction, Cell, 136, 823-837. (Year: 2009).*
Anonymous, Renal-Cancer-Prevention, 2021, https://www.cancer.org/cancer/kidney-cancer/causes-risks-prevention/prevention.htnnl, 1 page.
Anonymous, Renal-Cancer-Cure, 2021, https://www.cancergov/types/kidney/hp/kidney-treatment-pdq#:-:text=Renal%20cell%20cancer%2C%20also%20called,or%20degree%20of%20tunnor%20dissennination.
Anonymous, Renal-Carcinoma, 2021, https://ascopost.conn/news/february-2020/oral-hif2a-inhibitor-for-advanced-clear-cell-renal-cell-carcinonna/, 4 pages.
International Search Report and Written Opinion for PCT/US2019/056555 mailed Feb. 18, 2020, 10 pages.
Wehn et al., "Design and Activity of Specific Hypoxia-Inducible Factor 2# (HIF-2#) Inhibitors for the Treatment of Clear Cell Renal Cell Carcinoma: Discovery of Clinical Candidate (S)-3-((2,2-difluoro-1-hydroxy-7- (methylsulfonyl)-2,3-dihydro-1H-inden-4-yl)oxy)-5-fluorobenzonitrile (PT2385)", J. Med. Chem., DOI: 10.1021/acs.jmedchem.8b01196 Publication Date (Web): Oct. 5, 2018.
Xu et al., "3-[(1S,2S,3R)-2,3-Difluoro-1-hydroxy-7-methylsulfonyl-indan-4-yl]oxy-5-fluoro-benzonitrile (PT2977), a Hypoxia-Inducible Factor 2# (HIF-2#) Inhibitor for the Treatment of Clear Cell Renal Cell Carcinoma", J. Med. Chem., DOI: 10.1021/acs.jmedchem.9b00719, Publication Date (Web): Jun. 24, 2019.

* cited by examiner

*Primary Examiner* — Matthew P Coughlin
*Assistant Examiner* — Meghan C Heasley
(74) *Attorney, Agent, or Firm* — Squire Patton Boggs (US) LLP

(57) ABSTRACT

The present disclosure provides certain indane compounds that are Hypoxia Inducible Factor 2α (HIF-2α) inhibitors and are therefore useful for the treatment of diseases treatable by inhibition of HIF-2α. Also provided are pharmaceutical compositions containing such compounds and processes for preparing such compounds.

23 Claims, No Drawings

INDANE DERIVATIVES AS HYPOXIA INDUCIBLE FACTOR-2(α) INHIBITORS

CROSS REFERENCE TO RELATED APPLICATIONS

This application is a national stage entry under 37 C.F.R. § 371 of international application no. PCT/US2019/056555, filed on Oct. 16, 2019, which claims the benefit of U.S. Provisional Application No. 62/747,028, filed on Oct. 17, 2018; the entire contents of which are herein incorporated by reference.

FIELD OF THE DISCLOSURE

The present disclosure provides certain indane compounds that are Hypoxia Inducible Factor 2α (HIF-2α) inhibitors and are therefore useful for the treatment of diseases treatable by inhibition of HIF-2α. Also provided are pharmaceutical compositions containing such compounds and processes for preparing such compounds.

BACKGROUND

Hypoxia is as an important regulator of both physiological and pathological processes, including various types of cancer, liver disease such as nonalcoholic steatohepatitis (NASH), inflammatory disease such as inflammatory bowel disease (IBD), pulmonary diseases such as pulmonary arterial hypertension (PAH), and iron load disorders.

Hypoxia is well-known to drive cancer progression and is strongly associated with poor patient prognosis, resistance to chemotherapy and radiation treatment. With the progress over the past several decades in elucidating molecular mechanisms that enable cellular adaptation to chronic oxygen deprivation, there is a strong interest in developing drugs that can effectively block the hypoxic response pathway in tumors. Among signaling modules, involved in the hypoxic response, that have been explored as therapeutic targets for treating cancer, HIF-α proteins continue to draw interest as they offer the possibility to broadly inhibit downstream hypoxia effects within both tumor and tumor microenvironment. Thus, directly targeting HIF-α proteins offers an exciting opportunity to attack tumors on multiple fronts (see Keith, et al. Nature Rev. Cancer 12: 9-22, 2012).

Hypoxia-Inducible Factors (HIF-1α and HIF-2α) are key transcription factors in the hypoxia pathway, and therefore serve as attractive targets for therapeutic intervention. The half-life of HIF-α proteins is tightly regulated by the oxidative status within the cell. Under normoxic conditions, HIF-specific prolyl-hydroxylases (PHD) hydroxylate specific proline residues on the HIF proteins, which are then recognized by the tumor suppressor von Rippel-Lindau (VHL). The binding of VHL further recruits E3 ubiquition-ligase complex that targets HIF-α proteins for proteasome mediated degradation. Under hypoxic conditions, when PHDs are inhibited as they require oxygen to be functional, HIF-α proteins accumulate and enter the nucleus to actively drive gene expression. In addition, genetic mutations of the VHL gene which result in loss of VHL function lead to constitutively active HIF-α proteins independent of oxygen levels. Upon activation, these transcription factors stimulate the expression of genes that collectively regulate anaerobic metabolism, angiogenesis, cell proliferation, cell survival, extracellular matrix remodeling, pH homeostasis, amino acid and nucleotide metabolism, and genomic instability.

Both HIF-1α and HIF-2α dimerize with HIF-1β (also named as ARNT: aryl hydrocarbon receptor nuclear translocator) and the dimer subsequently binds to hypoxia response elements (HRE) on target genes. The expression of HIF-1β is independent of oxygen levels or VHL status, thus, transcriptional activity of the complex is primarily controlled by the availability of the HIF-α proteins. HIF-1α and HIF-2α differ in their tissue distribution, sensitivity to hypoxia, timing of activation and target gene specificity (Hu, et al. Mol. Cell Biol. 2003, 23, 9361-9374 and Keith, et al. Nature Rev. Cancer 2012, 12, 9-22). Whereas HIF-1α mRNA is ubiquitously expressed, the expression of HIF-2α mRNA is found predominantly in kidney fibroblasts, hepatocytes and intestinal lumen epithelial cells. Neither HIF-α is detected in normal tissue with the exception of HIF-2α, which is expressed in macrophages (see Talks, et al. Am. J Pathol. 2000, 157, 411-421). In response to hypoxia, HIF-1α exhibits a transient, acute transcriptional response. In contrast, HIF-2α presents a more prolonged transcriptional effect. Furthermore, HIF-2α has greater transcriptional activity than HIF-1α under moderately hypoxic conditions like those encountered in end capillaries (see Holmquist-Menge/bier, et al. Cancer Cell 10: 413-423, 2006). Although some hypoxia-regulated genes are regulated by both HIF-1α and HIF-2α, certain genes are only responsive to a specific HIF-α protein. For example, lactate dehydrogenase A (LDHA), phosphoglycerate kinase (PGK) and pyruvate dehydrogenase kinase 1 (PDK1) are mostly controlled by HIF-1α, while Oct-4 and erythropoietin (EPO) are exclusively regulated by HIF-2α.

In general, the relative contributions of HIF-α proteins on gene transcription are both cell type specific, and disease specific. In fact, there are reports supporting HIF-α proteins playing conflicting roles in tumorigenesis. One example is the regulation of HIF-α on MYC, which is an important transcription factor and frequently overexpressed in human cancers. It has been shown that HIF-2α activation increases MYC transcription activity, while HIF-1α inhibits MYC activity. As a result, in MYC driven tumors, HIF-2α inhibition decreased proliferation whereas HIF-1α inhibition increased growth (see Gordan, et al. Cancer Cell 2007, 11, 335-347 and Koshiji et al. EMBO J 2004, 23, 1949-1956). Therefore, identification of small molecules that specifically inhibit HIF-2α activity is desirable. In addition, HIF-2α is demonstrated to be a key driver of Clear Cell Renal Cell Carcinoma (ccRCC) with VHL deficiency and several other pseudohypoxic tumors (glioblastoma, neuroblastoma etc.). Thus, a specific HIF-2α inhibitor devoid of HIF-1α activity will offer therapeutic benefits with limited toxicity than a pan-HIF u inhibitor.

In addition to a direct role in regulating growth-promoting genes in tumor cells (e.g. ccRCC), HIF-2α also mediates the immunosuppressive effect of hypoxia on the tumor microenvironment. Expression of HIF-2α has been detected in cells of the myeloid lineage, and accumulation of HIF-2a protein has been readily detected in various human cancers (see Talks K L, et al. Am J Pathol. 2000, 157(2), 411-421). Overexpression of HIF-2α in tumor-associated macrophages (TAMs) is associated with high-grade human tumors and is specifically correlated with poor prognosis. Mechanistically, HIF-2α promotes the polarization of macrophages to the immunosuppressive M2 phenotype and enhances migration and invasion of tumor-associated macrophages (see Imtiyaz H Z et al. J Clin Invest. 2010, 120(8), 2699-2714). Furthermore, HIF-2α can indirectly promote additional immunosuppressive pathways (e.g. adenosine and arginase etc.) by modulating the expression of key signaling regulators such as adenosine A2B/A2A receptors and arginase. These data suggest that HIF-2α may be a potential therapeutic target for treating a broader range of inflammatory disorders and cancer, as a single agent or in combination with other therapeutic agents e.g., immunotherapies.

Because of the key roles of HIF-α proteins in regulating physiological response to the change of oxygen levels, they have been causally associated with many hypoxia-related pathological processes in addition to cancer. Inflammatory bowel disease (IBD) is a chronic relapsing inflammatory disease of the intestine. Normally, the intestines maintain a dynamic and rapid fluctuation in cellular oxygen tension, with the tips of the epithelial villi being hypoxic and the base of the epithelial villi better oxygenated. A dysregulated epithelial oxygen tension plays a critical role in intestinal inflammation and resolution in IBD (see Shah Y. M., *Molecular and Cellular Pediatrics,* 2016 December; 3(1):1). Even though HIF-1α and HIF-2α can bind to the same canonical HREs, multiple studies have demonstrated that HIF-1α and HIF-2α regulate distinct subset of genes, leading to contrasting effect in symptoms of IBD. HIF-1α in intestinal epithelial cells is widely recognized as a major protective factor in IBD (see Karhausen J, et al. *J Clin Invest.* 2004, 114(8), 1098-1106; Furuta G T, et al. *J Exp Med.* 2001, 193(9), 1027-1034). However, HIF-2α activation contributes to IBD through multiple mechanisms, including directly regulating a number of pro-inflammatory cytokines such as tumor necrosis factor-α to drive inflammation, and indirectly disrupting intestine barrier integrity through increasing the turnover of tight junction protein occluding (see Xue X, et al. *Gastroenterology.* 2013; 145 (4):831-841; Glover L E, et al. *Proc Natl Acad Sci USA.* 2013; 110(49):19820-19825). Therefore, in IBD, a specific HIF-2α inhibitor holds the promise of suppressing chronic activation of HIF-2α to revert the pro-inflammatory response and increase the intestinal barrier integrity.

With the growing epidemic of obesity and metabolic syndrome, NASH is becoming a common chronic liver disease, and limited therapeutic options are available. A recent study has demonstrated a positive correlation between intestinal HIF-2α signaling with body-mass index and hepatic toxicity, with further animal model study supporting the causality of this correlation (see Xie C, et al. *Nat Med.* 2017 November; 23(11), 1298-1308.). Thus, targeting intestinal HIF-2α represents a novel therapeutic strategy for NASH.

PAH is a life-threatening disease with very poor prognosis. Progressive pulmonary vascular remodeling, characterized by concentric pulmonary arterial wall thickening and obliterative intimal lesions, is one of the major causes for the elevation of pulmonary vascular resistance (PVR) and pulmonary arterial pressure (PAP) in patients with PAH (see Aggarwal S, et al. *Compr Physiol.* 2013 July, 3(3), 1011-34). Recently, HIF-2α is found to contribute to the process of hypoxic pulmonary vascular remodeling, reduced plasticity of the vascular bed, and ultimately, debilitating PAH (see Andrew S., et al. *Proc Natl Acad Sci U.S.A.* 2016 Aug. 2, 113(31), 8801-8806, Tang H, et al. *Am J Physiol Lung Cell Mol Physiol.* 2018 Feb. 1, 314(2), L256-L275.). These studies have offered new insight into the role of pulmonary endothelial HIF-2a in regulating the pulmonary vascular response to hypoxia, and more importantly, offer a much-needed intervention therapeutics strategy by targeting HIF-2α.

Iron is an essential nutrient that is required for oxygen delivery and serves as a cofactor in many key enzymatic and redox reactions. HIF-2α regulates the expression of key genes that contribute to iron absorption, which, when disrupted, leads to iron load disorders. For example, an elegant study with mice lacking HIF-2α in the intestinal epithelium showed HIF-2α knockout results in a significant decrease in the duodenal levels of Dmt, Dcytb and FPN mRNAs, all important genes in iron transport and absorption. More importantly, these effects were not compensated by HIF-1α (see Mastrogiannaki M, et al. *J Clin Invest.* 2009, 119(5), 1159-1166). Thus, a specific small molecule targeting HIF-2 α holds a great potential of improving iron homeostasis in patients with iron disorders. Therefore, identification of small molecules that inhibit HIF-2α activity is desirable. The present disclosure fulfills this and related needs.

SUMMARY

In a first aspect, provided is a compound of Formula (I):

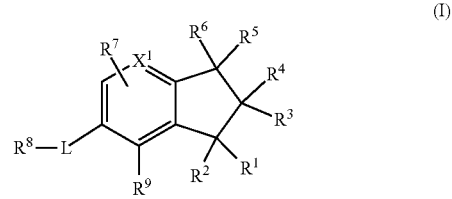

wherein:
 $X^1$ is CH or N;
 $R^1$ is hydroxy, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15}$ where R$^{10}$, R$^{11}$, and R$^{15}$ are independently alkyl or alkyl substituted with amino, carboxy or hydroxy, R$^{12}$ and R$^{13}$ are independently alkyl or alkyl substituted with amino, carboxy or hydroxy or R$^{12}$ and R$^{13}$ together with the nitrogen atom to which they are attached form optionally substituted heterocyclyl, and R$^{14}$ is hydrogen, alkyl, or haloalkyl;
 $R^2$ is hydrogen, deuterium, alkyl, haloalkyl, alkynyl, or alkenyl;
 $R^3$ and $R^4$ are independently hydrogen, deuterium, alkyl, cycloalkyl, halo, haloalkyl, hydroxyalkyl, or alkoxyalkyl; or
 $R^3$ and $R^4$ together with the carbon to which they are attached form oxo, cycloalkylene, or 4 to 6 membered optionally substituted heterocyclylene;
 $R^5$ is hydrogen, deuterium, alkyl, halo, haloalkyl, hydroxy, or alkoxy;
 $R^6$ is hydrogen, deuterium, alkyl, cycloalkyl, or halo; or
 $R^5$ and $R^6$ together with the carbon to which they are attached form cycloalkylene or 4 to 6 membered optionally substituted heterocyclylene; provided R$^1$ and R$^2$ and R$^3$ and R$^4$ together with the carbon to which they are attached do not form cycloalkylene or optionally substituted 4 to 6 membered heterocyclylene simultaneously;
 $R^7$ is hydrogen, deuterium, alkyl, alkoxy, cyano, halo, haloalkyl, or haloalkoxy;
 L is a bond, S, SO, SO$_2$, O, CO, or NR$^{16}$ where R$^{16}$ is hydrogen or alkyl;
 $R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and/or $R^1$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl; and $R^9$ is alkyl, alkenyl, alkynyl, cycloalkyl, alkoxy, cyano, halo, haloalkyl, haloalkoxy, alkylsulfoxide, or alkylsulfonyl, or heteroaryl wherein the heteroaryl is optionally substituted with $R^d$, $R^e$, and/or R independently selected from hydrogen, alkyl, haloalkyl, haloalkoxy, alkoxy, hydroxy, halo, and cyano; or a pharmaceutically acceptable salt thereof; provided that:

(i) (a) when L is O, then $R^8$ is not methyl; (b) when $R^2$, $R^3$, $R^4$ are hydrogen, $R^5$ and $R^6$ are independently hydrogen or methyl, $R^9$ is alkyl or alkoxy, and L is O, then $R^8$ is not ethyl; and (c) when $R^2$, $R^3$, $R^4$, $R^5$, and $R^6$ are hydrogen, $R^7$ is hydrogen or bromo, $R^9$ is alkyl, alkoxy, and L is O, then $R^8$ is not benzyl, cyclopentyl, hexyl, 2-phenethyl, or alkyl; and (ii) the compound of formula (I) is not 1(2H)-Isoquinolinone, 5-[(3-amino-4,6-difluoro-2,3-dihydro-1H-inden-5-yl)carbonyl]; 1H-Inden-1-amine, 7-chloro-2,3-dihydro-6-(trifluoromethoxy); 1H-Inden-1-amine, 7-fluoro-2,3-dihydro-6-(trifluoromethoxy); 1H-Indene-5-propanol, 2,3-dihydro-3-hydroxy-4,6-dimethyl; 1H-Indene-5-pentanol, 2,3-dihydro-3-hydroxy-4-methoxy; 1H-Inden-4-ol, 3-amino-2,3-dihydro-2,2,7-trimethyl-5-propyl-; 1H-Indene-5-ethanol, 2,3-dihydro-3-hydroxy-2,4,6-trimethyl-; 1H-Inden-1-ol, 6-ethyl-2,3-dihydro-2,5,7-trimethyl-; 1H-Indene-5-ethanol, 2,3-dihydro-3-hydroxy-2,4,6-trimethyl-; or 1H-Inden-1-ol, 6-(2-chloroethyl)-2,3-dihydro-2,2,5,7-tetramethyl; or a pharmaceutically acceptable salt thereof.

In a second aspect, this disclosure is directed to a method of treating a disease treatable by inhibition of HIF2α in a patient, preferably a patient in need of such treatment, which method comprises administering to the patient, preferably a patient in need thereof, a therapeutically effective amount of a compound of Formula (I'):

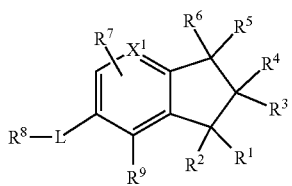

wherein:

$X^1$ is CH or N;

$R^1$ is hydroxy, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15}$ where $R^{10}$, $R^{11}$, and $R^{15}$ are independently alkyl or alkyl substituted with amino, carboxy or hydroxy, $R^{12}$ and $R^{13}$ are independently alkyl or alkyl substituted with amino, carboxy or hydroxy or $R^{12}$ and $R^{13}$ together with the nitrogen atom to which they are attached form optionally substituted heterocyclyl, and $R^{14}$ is hydrogen, alkyl, or haloalkyl;

$R^2$ is hydrogen, deuterium, alkyl, haloalkyl, alkynyl, or alkenyl;

$R^3$ and $R^4$ are independently hydrogen, deuterium, alkyl, cycloalkyl, halo, haloalkyl, hydroxyalkyl, or alkoxyalkyl; or $R^3$ and $R^4$ together with the carbon to which they are attached form oxo, cycloalkylene, or 4 to 6 membered optionally substituted heterocyclylene;

$R^5$ is hydrogen, deuterium, alkyl, halo, haloalkyl, hydroxy, or alkoxy;

$R^6$ is hydrogen, deuterium, alkyl, cycloalkyl, or halo; or $R^5$ and $R^6$ together with the carbon to which they are attached form cycloalkylene or 4 to 6 membered optionally substituted heterocyclylene provided $R^1$ and $R^2$ and $R^3$ and $R^4$ together with the carbon to which they are attached do not form cycloalkylene or optionally substituted 4 to 6 membered heterocyclylene simultaneously;

$R^7$ is hydrogen, deuterium, alkyl, alkoxy, cyano, halo, haloalkyl, or haloalkoxy;

L is a bond, S, SO, SO$_2$, O, CO, or NR$^{16}$ where $R^{16}$ is hydrogen or alkyl;

$R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl; and $R^9$ is hydrogen, alkyl, alkenyl, alkynyl, cycloalkyl, alkoxy, cyano, halo, haloalkyl, haloalkoxy, alkylsulfoxide, or alkylsulfonyl, or heteroaryl wherein the heteroaryl is optionally substituted with $R^d$, $R^e$, and/or $R^f$ independently selected from hydrogen, alkyl, haloalkyl, haloalkoxy, alkoxy, hydroxy, halo, and cyano; or a pharmaceutically acceptable salt thereof, or a compound of Formula (I) as described in the first aspect above, a pharmaceutically acceptable salt (or any of the embodiments thereof described herein); or comprises administering to the patient, preferably a patient in need of such treatment, a therapeutically effective amount of a pharmaceutical composition comprising a compound of Formula (I) or (I'), or a pharmaceutically acceptable salt thereof (or any of the embodiments thereof described herein) and a pharmaceutically acceptable excipient.

In one embodiment the disease is cancer such as renal cancer, glioblastoma (see *PNAS* 2017, 114, E6137-E6146), renal cell carcinoma, pheochromocytomas, and paragangliomas (see *European Journal of Cancer* 2017, 86, 1-4). In another embodiment, non-cancer diseases that could benefit from Hif-2α inhibition include VHL (von Hippel-Lindau) disease (see *Oncotarget,* 2015, 6, 23036-23037), PAH (pulmonary artery hypertension) (see *Mol. Cell. Biol.* 2016, 36, 1584-1594), reflux esophagitis (see *Current Opinion in Pharmacology* 2017, 37, 93-99), hepatic steatosis (see *Nature Medicine* 2017, 23, 1298-1308), inflammatory disease such as inflammatory bowel disease (see *Nature*

*Reviews gastroenterology & Hepatology* 2017, 14, 596), and autoimmune disease such as Graft-versus-Host-Disease (see *Blood,* 2015, 126, 1865).

In a third aspect, the disclosure is directed to a pharmaceutical composition comprising a compound a compound of Formula (I) (or any of the embodiments thereof described herein) or a compound of Formula (I') or a pharmaceutically acceptable salt thereof; and a pharmaceutically acceptable excipient.

In a fourth aspect, the disclosure is directed to a compound of Formula (I) or (I'), (or any embodiments thereof described herein) or a pharmaceutically acceptable salt thereof for use as a medicament. In one embodiment, the compound of Formula (I) or (I') (and any embodiments thereof described herein) or a pharmaceutically acceptable salt thereof is useful for the treatment of one or more of diseases disclosed in the second aspect above.

In a fifth aspect provided is the use of a compound of Formula (I) or (I') or a pharmaceutically acceptable salt thereof (and any embodiments thereof disclosed herein) in the manufacture of a medicament for treating a disease in a patient in which the activity of HIF2α contributes to the pathology and/or symptoms of the disease. In one embodiment the disease is one or more of diseases disclosed in the second aspect above.

In a sixth aspect provided is a method of inhibiting HIF2α which method comprises contacting HIF2α with a compound of Formula (I) or (I') (or any of the embodiments thereof described herein) or a pharmaceutically acceptable salt thereof; or contacting HIF2α with a pharmaceutical composition comprising a compound of Formula (I) or (I') (or any of the embodiments thereof described herein) or a pharmaceutically acceptable salt thereof, and a pharmaceutically acceptable excipient.

In any of the aforementioned aspects and embodiments therein, involving the treatment of cancer, are further embodiments comprising administering the compound of Formula (I) or (I') or a pharmaceutically acceptable salt thereof (or any embodiments thereof disclosed herein) in combination with at least one additional anticancer agent such as an EGFR inhibitor including gefitinib, erlotinib, afatinib, icotinib, neratnib, rociletinib, cetuximab, panitumumab, zalutumumab, nimotuzumab, and matuzumab. In another embodiment, the compound of Formula (I) or (I') (and any embodiments thereof described herein) or a pharmaceutically acceptable salt thereof is administered in combination with a HER2/neu inhibitor including lapatinib, trastuzumab, and pertuzumab. In another embodiment, the compound of Formula (I) or (I') (and any embodiments thereof described herein) or a pharmaceutically acceptable salt thereof is administered in combination with a PI3k/mTOR inhibitor including idelalisib, buparlisib, BYL719, and LY3023414. In another embodiment, the compound of Formula (I) or (I') (and any embodiments thereof described herein) or a pharmaceutically acceptable salt thereof is administered in combination with a VEGF inhibitors such as bevacizumab, and/or a multi-tyrosine kinase inhibitors such as sorafenib, sunitinib, pazopanib, and cabozantinib. In another embodiment, the compound of Formula (I) or (I') (and any embodiments thereof described herein) or a pharmaceutically acceptable salt thereof is administered in combination with an immunotherapeutic agents such as PD-1 and PD-L1 inhibitors, CTLA4 inhibitors, IDO inhibitors, TDO inhibitors, A2A agonists, A2B agonists, STING agonists, RIG-1 agonists, Tyro/Axl/Mer inhibitors, glutaminase inhibitors, arginase inhibitors, CD73 inhibitors, CD39 inhibitors, TGF-β inhibitors, IL-2, interferon, PI3K-γ inhibitors, CSF-1R inhibitors, GITR agonists, OX40 agonists, TIM-3 antagonists, LAG-3 antagonists, CAR-T therapies, and therapeutic vaccines. When combination therapy is used, the agents can be administered simultaneously or sequentially.

DEFINITIONS

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear monovalent hydrocarbon radical of two to six carbon atoms or a branched monovalent hydrocarbon radical of three to six carbon atoms containing a double bond, e.g., propenyl, butenyl, and the like.

"Alkyldienyl" is alkenyl as defined above that is attached via the terminal divalent carbon. For example, in the compound below:

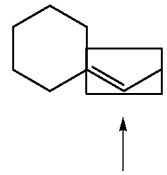

the alkyldienyl group is enclosed by the box which is indicated by the arrow.

"Haloalkyldienyl" is alkyldienyl that is substituted with one or two halo, each group as defined herein.

"Alkynyl" means a linear monovalent hydrocarbon radical of two to six carbon atoms or a branched monovalent hydrocarbon radical of three to six carbon atoms containing a triple bond, e.g., propynyl, butynyl, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Alkylsulfoxide" means a —SOR radical where R is alkyl as defined above, e.g., methylsulfoxide, ethylsulfoxide, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, hydroxyalkyl, alkoxyalkyl, or alkylcarbonyl, each as defined herein, e.g., aminomethyl, aminoethyl, methylaminomethyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Alkylcarbonyl" means a —C(O)R radical where R is alkyl as defined herein, e.g., methylcarbonyl, ethylcarbonyl, and the like.

"Aryl" means a monovalent monocyclic or bicyclic aromatic hydrocarbon radical of 6 to 10 ring atoms e.g., phenyl and naphthyl.

"Aralkyl" means a-(alkylene)-R radical where R is aryl as defined above, e.g., benzyl, phenethyl, and the like.

"Bicyclic cycloalkyl" means a fused bicyclic saturated monovalent hydrocarbon radical of six to ten carbon atoms optionally substituted with one or two substituents independently selected from alkyl, halo, alkoxy, hydroxy, and cyano. Examples include, but are not limited to, decalin, octahydro-1H-indene, and the like.

"Cycloalkyl" means a monocyclic saturated monovalent hydrocarbon radical of three to ten carbon atoms optionally substituted with one or two substituents independently selected from alkyl, alkyldienyl, halo, alkoxy, hydroxy, cyano, haloalkyldienyl and cyanoalkyl. Examples include, but are not limited to, cyclopropyl, cyclobutyl, cyclopentyl, cyclohexyl, 1-cyanocycloprop-1-yl, 1-cyanomethylcycloprop-1-yl, 3-fluorocyclohexyl, and the like. Cycloalkyl may include cycloalkylene as defined herein.

"Cycloalkylalkyl" means a-(alkylene)-R radical where R is cycloalkyl as defined above, e.g., cyclopropylmethyl, cyclohexylmethyl, and the like.

"Cycloalkylene" means a divalent cycloalkyl, as defined above, unless stated otherwise.

"Cycloalkenyl" means a monocyclic monovalent hydrocarbon radical of three to ten carbon atoms containing one or two double bond(s) optionally substituted with one or two substituents independently selected from alkyl, halo, alkoxy, hydroxy, cyano, and cyanoalkyl. Examples include, but are not limited to, cyclopropenyl, cyclobutenyl, cyclopentenyl, or cyclohexenyl, and the like.

"Oxocycloalkenyl" means a monocyclic monovalent hydrocarbon radical of three to ten carbon atoms containing one or two double bond(s) and an oxo group, and optionally substituted with one or two substituents independently selected from alkyl, halo, alkoxy, hydroxy, cyano, and cyanoalkyl. Examples include, but are not limited to, 3-oxocyclohex-1-enyl, and the like.

"Cyanoalkyl" means a linear monovalent hydrocarbon radical of one to six carbon atoms or a branched monovalent hydrocarbon radical of three to six carbons substituted with cyano e.g., cyanomethyl, cyanoethyl, and the like.

"Carboxy" means —C(O)OH.

"Dialkylamino" means a —NRR' radical where R and R' are alkyl as defined above, e.g., dimethylamino, methylethylamino, and the like.

"Halo" means fluoro, chloro, bromo, or iodo, preferably fluoro or chloro.

"Haloalkyl" means alkyl radical as defined above, which is substituted with one or more halogen atoms, e.g., one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C. Additionally, one or two ring carbon atoms in the heterocyclyl ring can optionally be replaced by a —C(O)— group. More specifically the term heterocyclyl includes, but is not limited to, pyrrolidinyl, piperidinyl, homopiperidinyl, 2-oxopyrrolidinyl, 2-oxopiperidinyl, morpholinyl, piperazinyl, tetrahydro-pyranyl, thiomorpholinyl, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylalkyl" or "heterocycloalkyl" means a-(alkylene)-R radical where R is heterocyclyl ring as defined above e.g., tetraydrofuranylmethyl, piperazinylmethyl, morpholinylethyl, and the like.

"Heterocyclylene" means a divalent heterocyclyl, as defined above, unless stated otherwise.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroarylene" means a divalent heteroaryl radical as defined above.

"Heteroaralkyl" means a-(alkylene)-R radical where R is heteroaryl as defined above, e.g., pyridinylmethyl, and the like. When the heteroaryl ring in heteroaralkyl contains 5- or 6 ring atoms it is also referred to herein as 5- or 6-membered heteroaralkyl.

The term "oxo," as used herein, alone or in combination, refers to =(0).

When needed, any definition herein may be used in combination with any other definition to describe a composite structural group. By convention, the trailing element of any such definition is that which attaches to the parent moiety. For example, the composite group alkoxyalkyl means that an alkoxy group attached to the parent molecule through an alkyl group.

The present disclosure also includes protected derivatives of compounds of Formula (I) or (I'), or a pharmaceutically acceptable salt thereof. For example, when compounds of Formula (I) or (I'), or a pharmaceutically acceptable salt thereof contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, 5$^{th}$ Ed., John Wiley & Sons, Inc. (2014), the disclosure of which is incorporated herein by reference in its entirety. The protected derivatives of compounds of Formula (I) or (I'), or a pharmaceutically acceptable salt thereof can be prepared by methods well known in the art.

The present disclosure also includes polymorphic forms and deuterated forms of the compound of Formula (I) or (I'), or a pharmaceutically acceptable salt thereof.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the active compound. Prodrugs are often useful because, in some situations, they may be easier to administer than the compound, or parent drug. They may, for instance, be bioavailable by oral administration whereas the parent drug is not. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. In some or any embodiments, compounds disclosed herein may be an active compound or active entity of a prodrug compound.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, PA, 1985, which is incorporated herein by reference in its entirety.

The compounds of Formula (I) or (I'), or a pharmaceutically acceptable salt thereof may have asymmetric centers. Compounds of Formula (I) or (I'), or a pharmaceutically acceptable salt thereof containing an asymmetrically substituted atom may be isolated in optically active or racemic forms. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. All chiral forms, diastereomeric forms, all mixtures of chiral and/or diasteromeric forms, and racemic forms are within the scope of this disclosure, unless a specific stereochemistry or isomeric form is specifically indicated. It will also be understood by a person of ordinary skill in the art that when a compound is denoted as (R) stereoisomer, it may contain the corresponding (S) stereoisomer as an impurity and vice versa. In some or any embodiments, the impurity is ≤15%, ≤10%, ≤5%, ≤2%, or ≤1%

Certain compounds of Formula (I) or (I'), or a pharmaceutically acceptable salt thereof can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, and heterocyclyl are substituted, they include all the positional isomers albeit only a few examples are set forth. Furthermore, all hydrates of a compound of Formula (I) or (I'), or a pharmaceutically acceptable salt thereof are within the scope of this disclosure.

The compounds of Formula (I) or (I'), or a pharmaceutically acceptable salt thereof may also contain unnatural amounts of isotopes at one or more of the atoms that constitute such compounds. Unnatural amounts of an isotope may be defined as ranging from the amount found in nature to an amount 100% of the atom as an isotope in question. that differ only in the presence of one or more isotopically enriched atoms. Exemplary isotopes that can be incorporated into compounds of the present invention, such as a compound of Formula (I) (and any embodiment thereof disclosed herein including specific compounds) include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$, respectively. Isotopically-labeled compounds (e.g., those labeled with $^3H$ and $^{14}C$) can be useful in compound or substrate tissue distribution assays. Tritiated (i.e., $^3H$) and carbon-14 (i.e., $^{14}C$) isotopes can be useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^2$H or $^3$H, or one or more carbon atoms are replaced by $^{13}$C- or $^{14}$C-enriched carbon. Positron emitting isotopes such as $^{15}$O, $^{13}$N, $^{11}$C, and $^{15}$F are useful for positron emission tomography (PET) studies to examine substrate receptor occupancy.

Isotopically labeled compounds can generally be prepared by following procedures analogous to those disclosed in the Schemes or in the Examples herein, by substituting an isotopically labeled reagent for a non-isotopically labeled reagent.

Certain structures provided herein are drawn with one or more floating substituents. Unless provided otherwise or otherwise clear from the context, the substituent(s) may be present on any atom of the ring to which it is attached, where chemically feasible and valency rules permitting. For example, in the structure:

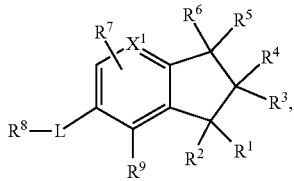

the $R^7$ substituent can replace any hydrogen on the benzo portion of the bicyclic ring, including the hydrogen of CH when $X^1$ is CH.

"Optionally substituted aryl" means aryl that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylthio, alkylsulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano, unless stated otherwise.

"Optionally substituted heterocyclylene" is a divalent optionally substituted heterocyclyl as defined above.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Spirocycloalkyl" means a saturated bicyclic ring having 6 to 10 ring carbon atoms wherein the rings are connected through only one atom, the connecting atom is also called the spiroatom, most often a quaternary carbon ("spiro carbon"). The spirocycloalkyl ring is optionally substituted with one or two substituents independently selected from alkyl, halo, alkoxy, hydroxy, and cyano. Representative examples include, but are not limited to, spiro[3.3]heptane, spiro[3.4]octane, spiro[3.5]nonane, spiro[4.4]nonane (1:2:1), and the like.

"Spiroheterocyclyl" means a saturated bicyclic ring having 6 to 10 ring atoms in which one, two, or three ring atoms are heteroatom selected from N, O, and S(O)$_n$, where n is an integer from 0 to 2, the remaining ring atoms being C and the rings are connected through only one atom, the connecting atom is also called the spiroatom, most often a quaternary carbon ("spiro carbon"). The spiroheterocyclyl ring is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano. Representative examples include, but are not limited to, 2,6-diazaspiro[3.3]heptane, 2,6-diazaspiro[3.4]octane, 2-azaspiro[3.4]octane, 2-azaspiro[3.5]nonane, 2,7-diazaspiro[4.4]nonane, and the like.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a disease or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease;
(2) inhibiting the disease, i.e., arresting or reducing the development of the disease or its clinical symptoms; or
(3) relieving the disease, i.e., causing regression of the disease or its clinical symptoms.

A "therapeutically effective amount" means the amount of a compound of Formula (I) or (I') or a pharmaceutically acceptable salt thereof that, when administered to a patient for treating a disease, is sufficient to affect such treatment for the disease. The "therapeutically effective amount" will vary depending on the compound, the disease and its severity and the age, weight, etc., of the mammal to be treated.

The terms "inhibiting" and "reducing," or any variation of these terms in relation of HIF-2α, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of HIF-2α activity compared to normal.

EMBODIMENTS

In further embodiments 1-21 below, the present disclosure includes: 1. In embodiment 1, the compound of Formula (I) is as described in the first aspect of the Summary above.

In a first subembodiment of embodiment 1, the compound of Formula (I) or a pharmaceutical salt thereof is wherein $R^1$ is hydroxy. In a second subembodiment of embodiment 1, the compound of Formula (I) or a pharmaceutical salt thereof is wherein $R^1$ is amino. In a third subembodiment of embodiment 1, the compound of Formula (I) or a pharmaceutical salt thereof is wherein $R^1$ is —$OCOR^{10}$, —$OCOOR^{11}$, —$OCONR^{12}R^{13}$, —$OCHR^{14}OCOR^{15}$ or —$OCHR^{14}OCOOR^{15}$ where $R^{10}$, $R^{11}$, and $R^{15}$ are as defined in the Summary.

In a fourth subembodiment of embodiment 1 and subembodiments contained therein (i.e. first, second, and third subembodiments above), the compounds of Formula (I) or a pharmaceutical salt thereof are those wherein $R^6$ is halo, preferably $R^6$ is fluoro.

In a fifth subembodiment of embodiment 1 and subembodiments contained therein (i.e. first, second, and third subembodiments), the compounds of Formula (I) or a pharmaceutical salt thereof are those wherein $R^6$ is alkyl, preferably $R^6$ is methyl.

In a sixth subembodiment of embodiment 1 and subembodiments contained therein (i.e. first, second, and third subembodiments), the compounds of Formula (I) or a pharmaceutical salt thereof are those wherein $R^6$ is hydrogen or deuterium.

In a seventh subembodiment of embodiment 1 and subembodiments contained therein (i.e. first, second, and third subembodiments), the compounds of Formula (I) or a pharmaceutical salt thereof are those wherein $R^6$ is cycloalkyl, preferably $R^6$ is cyclopropyl, cyclobutyl, cyclopentyl, or cyclohexyl.

In an eighth subembodiment of embodiment 1, and subembodiments contained therein (i.e. first, second, third, fourth, fifth, six, and seventh subembodiments above), the compounds of Formula (I) or a pharmaceutical salt thereof are those wherein $R^5$ is halo or haloalkyl, preferably $R^5$ is difluoromethyl or trifluoromethyl.

In a ninth subembodiment of embodiment 1 and subembodiments contained therein (i.e. first, second, third, fourth, fifth, six, and seventh subembodiments above), the compounds of Formula (I) or a pharmaceutical salt thereof are those wherein $R^5$ is alkyl, preferably $R^5$ is methyl or ethyl.

In a tenth subembodiment of embodiment 1 and subembodiments contained therein (i.e. first, second, third, fourth, fifth, six, and seventh subembodiments), the compounds of Formula (I) or a pharmaceutical salt thereof are those wherein $R^5$ is hydrogen or alkoxy.

In an eleventh subembodiment of embodiment 1 and subembodiments contained therein (i.e. first, second, and third subembodiments), the compounds of Formula (I) or a pharmaceutical salt thereof are those wherein $R^5$ and $R^6$ together with the carbon to which they are attached form cycloalkylene, preferably $R^5$ and $R^6$ together with the carbon to which they are attached form cyclopropylene, cyclobutylene, or cyclopentylene each optionally substituted with one or two fluoro.

In a twelfth subembodiment of embodiment 1 and subembodiments contained therein (i.e. first, second, and third subembodiments), the compounds of Formula (I) or a pharmaceutical salt thereof are those wherein $R^5$ and $R^6$ together with the carbon to which they are attached form or 4 to 6 membered optionally substituted heterocyclylene, preferably $R^5$ and $R^6$ together with the carbon to which they are attached form

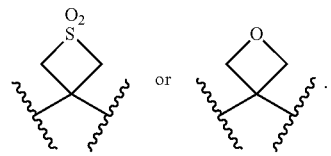 [SMILES: *C1(*)CS(=O)(=O)C1 ; *C1(*)COC1]

In a thirteenth subembodiment of embodiment 1 and subembodiments contained therein (i.e. first to twelfth subembodiments), the compounds of Formula (I) or a pharmaceutical salt thereof are those wherein $X^1$ is CH or $CR^7$.

In a fourteenth subembodiment of embodiment 1 and subembodiments contained therein (i.e. first to twelfth subembodiments), the compounds of Formula (I) or a pharmaceutical salt thereof are those wherein $X^1$ is N.

2. In embodiment 2, the compound of embodiment 1 or a pharmaceutically acceptable salt thereof has the structure of formula (IIa) or (IIb):

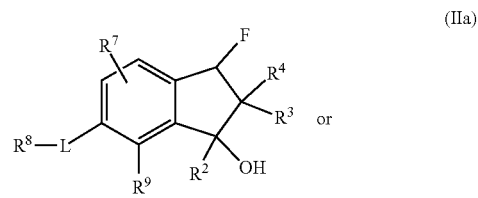

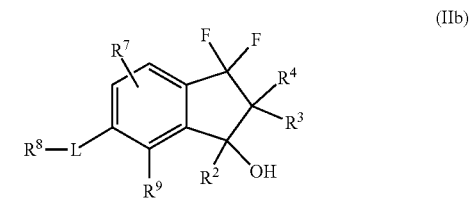

In a first subembodiment of embodiment 2 the compound or a pharmaceutically acceptable salt thereof has the structure of formula (IIa). In a second subembodiment of embodiment 2 the compound or a pharmaceutically acceptable salt thereof has the structure of formula (IIb).

3. In embodiment 3, the compound of embodiment 1 or a pharmaceutically acceptable salt thereof has the structure of formula (IIIa) or (IIIb):

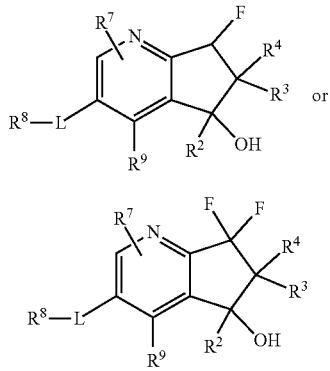
(IIIa)

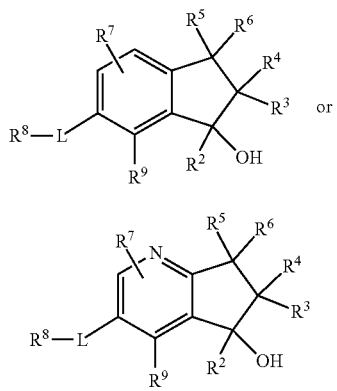
(IIIb)

In a first subembodiment of embodiment 3, the compound or a pharmaceutically acceptable salt thereof has the structure of formula (IIIa). In a second subembodiment of embodiment 3, the compound or a pharmaceutically acceptable salt thereof has the structure of formula (IIIb).

4. In embodiment 4, the compound of embodiment 1 or a pharmaceutically acceptable salt thereof has the structure of formula (IVa) or (IVb):

(IVa)

(IVb)

where $R^5$ and $R^6$ together with the carbon to which they are attached form cycloalkylene, preferably $R^5$ and $R^6$ together with the carbon to which they are attached form cyclopropylene, cyclobutylene or cyclopentylene optionally substituted with one or two fluoro. In a first subembodiment of embodiment 4, the compound or a pharmaceutically acceptable salt thereof has the structure of formula (IVa). In a second subembodiment of embodiment 4, the compound or a pharmaceutically acceptable salt thereof has the structure of formula (IVb).

5. In embodiment 5, the compound of embodiment 1 or a pharmaceutically acceptable salt thereof has the structure of formula (Va) or (Vb):

(Va)

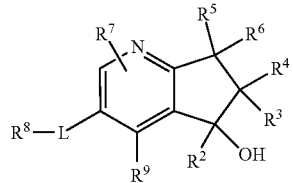
(Vb)

where $R^5$ and $R^6$ together with the carbon to which they are attached form or 4 to 6 membered optionally substituted heterocyclylene, preferably $R^5$ and $R^6$ together with the carbon to which they are attached form

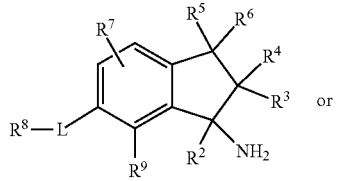

In a first subembodiment of embodiment 5, the compound or a pharmaceutically acceptable salt thereof has the structure of formula (Va). In a second subembodiment of embodiment 5, the compound or a pharmaceutically acceptable salt thereof has the structure of formula (Vb).

6. In embodiment 6, the compound of embodiment 1 or a pharmaceutically acceptable salt thereof has the structure of formula (VIa) or (VIb):

(VIa)

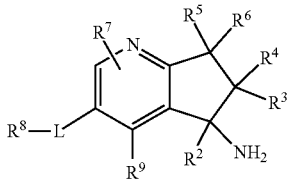
(VIb)

where $R^5$ and $R^6$ together with the carbon to which they are attached form cycloalkylene, preferably $R^5$ and $R^6$ together with the carbon to which they are attached form cyclopropylene, cyclobutylene or cyclopentylene optionally substituted with one or two fluoro. In a first subembodiment of embodiment 6, the compound or a pharmaceutically acceptable salt thereof has the structure of formula (VIa). In a second subembodiment of embodiment 6, the compound or a pharmaceutically acceptable salt thereof has the structure of formula (VIb)

7. In embodiment 7, the compound of embodiment 1 or a pharmaceutically acceptable salt thereof has the structure of formula (VIIa) or (VIIb):

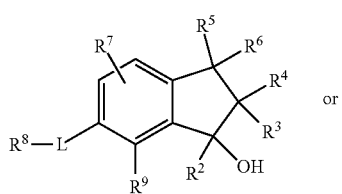

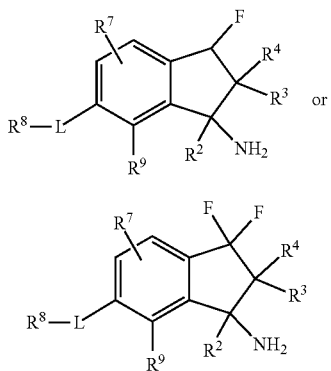

(VIIa)

(VIIb)

In a first subembodiment of embodiment 7, the compound or a pharmaceutically acceptable salt thereof has the structure of formula (VIIa). In a second subembodiment of embodiment 7, the compound or a pharmaceutically acceptable salt thereof has the structure of formula (VIIb).

8. In embodiment 8, the compound of any of embodiments 1 to 7 and subembodiments contained therein (e.g., subembodiments first to fourteenth of embodiment 1) or a pharmaceutically acceptable salt thereof, are where one of $R^3$ and $R^4$ is halo, preferably fluoro.

In a first subembodiment, one of $R^3$ is fluoro and $R^4$ is hydrogen. 9. In embodiment 9, the compound of any of embodiments 1 to 7 and subembodiments contained therein or a pharmaceutically acceptable salt thereof, are where $R^3$ and $R^4$ are halo, preferably fluoro.

10. In embodiment 10, the compound of any one of embodiments 1 to 9 and subembodiments contained therein or a pharmaceutically acceptable salt thereof is wherein L is O, S, SO, $SO_2$, or NH. In a first subembodiment of embodiment 10, L is O. In a second subembodiment of embodiment 10, L is S. In a third subembodiment of embodiment 10, L is NH. In a fourth subembodiment of embodiment 10, L is SO or $SO_2$. In a fourth subembodiment of embodiment 10 and subembodiments contained therein $R^8$ is cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl.

11. In embodiment 11, the compound of any one of embodiments 1 to 10 and subembodiments contained therein or a pharmaceutically acceptable salt thereof is wherein $R^9$ is methyl, ethyl, methoxy, fluoro, bromo, cyano, cyclopropyl, trifluoromethyl, difluoromethyl, difluoromethoxy, trifluoromethoxy, or methylsulfonyl. In a first subembodiment of embodiment 11, $R^7$ is difluoromethyl, difluoromethoxy, trifluoromethyl, or trifluoromethoxy. In a second subembodiment of embodiment 11, $R^9$ is difluoromethyl.

12. In embodiment 12, the compound of any one of embodiments 1 to 11 and subembodiments contained therein or a pharmaceutically acceptable salt thereof is wherein $R^8$ is phenyl substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl. In a first subembodiment of embodiment 12, $R^a$ and $R^b$ are independently selected from hydrogen, alkyl, alkoxy, hydroxy, halo, haloalkyl, haloalkoxy, and cyano. In a second subembodiment of embodiment 12, $R^a$, $R^b$, and $R^c$ are independently selected from hydrogen, methyl, methoxy, hydroxy, chloro, fluoro, cyano, difluoromethyl, trifluoromethyl, difluoromethoxy, and trifluoromethoxy. In a third subembodiment of embodiment 12, $R^a$, $R^b$, and/or $R^c$ are independently selected from hydrogen, alkyl, haloalkyl, alkoxy, halo, and cyano. In a fourth subembodiment of embodiment 12, $R^8$ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, or 3-cyano-5-difluoromethylphenyl. In a fourth subembodiment of embodiment 12, $R^8$ is 3-cyano-5-fluorophenyl.

13. In embodiment 13, the compound of any one of embodiments 1 to 11 and subembodiments contained therein or a pharmaceutically acceptable salt thereof is wherein $R^8$ is cycloalkyl or cycloalkylalkyl each optionally substituted with one or two substituents independently selected from alkyl, halo, alkoxy, cyano, alkyldienyl, haloalkyldienyl, and hydroxy. In a first subembodiment of embodiment 13, $R^8$ is cyclopropylmethyl, cyclopropylethyl, cyclobutylmethyl, cyclobutylethyl, cyclopentylmethyl, cyclopentylethyl, or cyclohexylmethyl, each optionally substituted with one or two substituents independently selected from alkyl, halo, alkoxy, cyano, and hydroxy. In a second subembodiment of embodiment 13, $R^8$ is cyclopropylmethyl, cyclopropylethyl, cyclobutylmethyl, cyclobutylethyl, cyclopentylmethyl, cyclopentylethyl, or cyclohexylmethyl, each substituted with one or two substituents independently selected from hydrogen, methyl, methoxy, cyano, and fluoro, preferably $R^8$ is cyclopropylmethyl, 1-cyanocyclopropylmethyl, cyclobutylmethyl, 2-fluorocyclopropylmethyl, or 1-cyanocyclobutylmethyl. In a third subembodiment of embodiment 13, $R^8$ is cyclopropyl, cyclobutyl, cyclopentyl, or cyclohexyl, each optionally substituted with one or two substituents independently selected from alkyl, halo, alkoxy, cyano, and hydroxy. In a fourth subembodiment of embodiment 13, $R^8$ is cyclopropyl, cyclobutyl, cyclopentyl, or cyclohexyl, each optionally substituted with one or two substituents independently selected from methyl, cyano, methoxy, and fluoro, preferably, $R^8$ is cyclobutyl, 3-fluorocyclobutyl, 3,3-difluorocyclobutyl, 3-cyanocyclobutyl, 3-fluorocyclohexyl, or 3-cyano-3-methylcyclobutyl.

14. In embodiment 14, the compound of any one of embodiments 1 to 11 and subembodiments contained therein or a pharmaceutically acceptable salt thereof is wherein $R^8$ is heteroaryl substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl. In a first subembodiment of embodiment 14, $R^8$ is 5- or 6-membered heteroaryl e.g., pyridyl, pyridazinyl, pyrimidinyl, thienyl, furanyl, thiazolyl, oxazolyl, imidazolyl, or pyrazinyl, each ring substituted with $R^a$, $R^b$, and/or $R^c$ wherein $R^a$ and $R^b$ are independently selected from hydrogen, alkyl, alkoxy, hydroxy, halo, haloalkyl, haloalkoxy, and cyano and $R^c$ is selected from hydrogen, alkyl, halo, haloalkyl, and haloalkoxy. In a second subembodiment of embodiment 14, $R^8$ is pyridin-3-yl, pyridin-2-yl, pyridazin-3-yl, pyridazin-4-yl, pyrimidin-5-yl, pyrimidin-2-yl, thien-2-yl, furan-2-yl, thiazol-5-yl, oxazol-5-yl, imidazol-5-yl, furan-3-yl thien-3-yl, thiazol-4-yl, pyridin-4-yl, oxazol-2-yl, imidazol-2-yl, pyridin-2-yl, pyrazin-2-yl or thiazol-2-yl, each ring substituted with $R^a$, $R^b$, and/or $R^c$ wherein $R^a$ and $R^b$ are independently selected from hydrogen, methyl, methoxy, hydroxy, chloro, fluoro, difluoromethyl, trifluoromethyl, difluoromethoxy, and trifluoromethoxy and $R^c$ is selected from hydrogen, methyl, cyano, chloro, fluoro, difluoromethyl, trifluoromethyl, difluoromethoxy, and trifluoromethoxy. In a third subembodiment of embodiment 14, $R^8$ is 5-cyanopyridin-3-yl, 5-chloropyridin-3-yl, or 5-fluoropyridin-3-yl.

15. In embodiment 12, the compound of any one of embodiments 1-11 and subembodiments contained therein or a pharmaceutically acceptable salt thereof is wherein $R^8$ is bicyclic heteroaryl substituted with $R^a$, $R^b$, and/or $R^c$, wherein $R^a$ and $R^b$ are independently selected from hydrogen, alkyl, alkoxy, hydroxy, halo, haloalkyl, haloalkoxy, and cyano and $R^c$ is selected from hydrogen, alkyl, halo, haloalkyl, haloalkoxy, hydroxyalkyl, alkoxyalkyl, and aminoalkyl.

16. In embodiment 16, the compound of any one of embodiments 1 to 11 and subembodiments contained therein or a pharmaceutically acceptable salt thereof is wherein $R^8$ is heterocyclyl, wherein heterocyclyl is substituted with $R^a$, $R^b$, and/or $R^c$ wherein $R^a$ and $R^b$ are independently selected from hydrogen, alkyl, alkoxy, hydroxy, halo, haloalkyl, haloalkoxy, and cyano and $R^c$ is hydrogen, alkyl, halo, haloalkyl, haloalkoxy, hydroxyalkyl, alkoxyalkyl, or aminoalkyl. In a first subembodiment of embodiment 18, $R^8$ is tetrahydrofuranyl, tetrahydrohydropyranyl, or oxetanyl, each ring independently substituted with $R^a$ and $R^b$ wherein $R^a$ and $R^b$ are independently selected from hydrogen, methyl, and fluoro.

17. In embodiment 17, the compound of any one of embodiments 1 to 11 and subembodiments contained therein or a pharmaceutically acceptable salt thereof is wherein $R^8$ is spiroheterocyclyl. In one embodiment, the spiroheterocyclyl ring contains at least one nitrogen atom. In a second embodiment, the spiroheterocyclyl ring contains at least one oxygen atom.

18. In embodiment 18, the compound of any one of embodiments 1 to 17 and subembodiments contained therein or a pharmaceutically acceptable salt thereof is wherein $R^7$ is hydrogen, methyl, ethyl, methoxy, fluoro, trifluoromethyl or trifluoromethoxy. In a first subembodiment, $R^7$ is hydrogen.

19. In embodiment 19, the compound of any one of embodiments 1 to 18 and subembodiments contained therein or a pharmaceutically acceptable salt thereof is wherein $R^2$ is hydrogen, deuterium, methyl or ethyl. In a first subembodiment, $R^2$ is hydrogen. In a second subembodiment, $R^2$ is methyl. In a second subembodiment, $R^2$ is hydrogen, methyl, or ethyl.

20. In embodiment 20, the compound of any one of embodiments 1 to 19 and subembodiments contained therein or a pharmaceutically acceptable salt thereof is wherein the stereochemistry at the carbon to which $R^1$ is attached is (R).

21. In embodiment 20, the compound of any one of embodiments 1 to 19 and subembodiments contained therein or a pharmaceutically acceptable salt thereof is wherein the stereochemistry at the carbon to which $R^1$ is attached is (S).

Additional embodiments are provided in embodiments 22-52 below:

22. In embodiment 22, provided is compound of Formula (I), or a pharmaceutically acceptable salt thereof is as defined in the Summary.

23. In embodiment 23, the compound of embodiment 22, or a pharmaceutically salt thereof is wherein $R^3$ and $R^4$ are independently halo.

24. In embodiment 24, the compound of embodiment 22, or a pharmaceutically salt thereof is wherein $R^3$ is halo and $R^4$ is hydrogen.

25. In embodiment 25, the compound of any one of embodiments 22 to 24, or a pharmaceutically salt thereof is wherein $R^1$ is hydroxy.

26. In embodiment 26, the compound of any one of embodiments 22 to 24, or a pharmaceutically salt thereof is wherein $R^1$ is amino.

27. In embodiment 27, the compound of any one of embodiments 22 to 26, or a pharmaceutically salt thereof is wherein $R^6$ is halo.

28. In embodiment 28, the compound of any one of embodiments 22 to 26, or a pharmaceutically salt thereof is wherein $R^6$ is alkyl, preferably methyl.

29. In embodiment 29, the compound of any one of embodiments 22 to 26 and subembodiments contained, or a pharmaceutically salt thereof is wherein $R^6$ is hydrogen or deuterium.

30. In embodiment 30, the compound of any one of embodiments 22 to 26 and subembodiments contained, or a pharmaceutically salt thereof is wherein $R^6$ is cycloalkyl, preferably cyclopropyl, cyclobutyl, cyclopentyl, or cyclohexyl.

31. In embodiment 31, the compound of any one of embodiments 22 to 30 and subembodiments contained, or a pharmaceutically salt thereof is wherein $R^5$ is halo, preferably fluoro.

32. In embodiment 32, the compound of any one of embodiments 22 to 30 and subembodiments contained, or a pharmaceutically salt thereof is wherein $R^5$ is haloalkyl, preferably difluoromethyl, or trifluoromethyl.

33. In embodiment 33, the compound of any one of embodiments 22 to 30 and subembodiments contained, or a pharmaceutically acceptable salt thereof is wherein $R^5$ is alkyl, preferably methyl or ethyl.

34. In embodiment 34, the compound of any one of embodiments 22 to 30 and subembodiments contained, or a pharmaceutically salt thereof is wherein $R^5$ is hydrogen or alkoxy.

35. In embodiment 35, the compound of any one of embodiments 22 to 26 and subembodiments contained, or a pharmaceutically salt thereof is wherein $R^5$ and $R^6$ together with the carbon to which they are attached form cycloalkylene, preferably cyclopropylene, cyclobutylene, or cyclopentylene optionally substituted with one or two fluoro.

36. In embodiment 36, the compound of any one of embodiments 22 to 35 and subembodiments contained, or a pharmaceutically salt thereof is wherein $X^1$ is CH or $CR^7$.

37. In embodiment 37, the compound of embodiment 22, or a pharmaceutically salt thereof is wherein has a structure of formula (IIa) or (IIb):

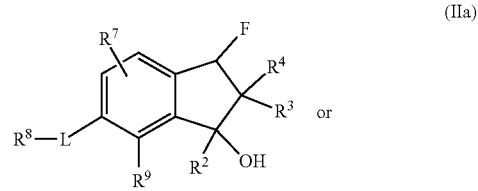

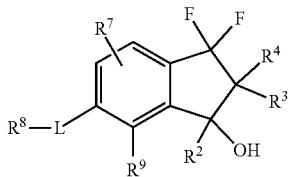
(IIb)

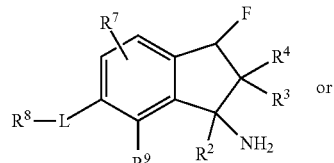
(VIIa)

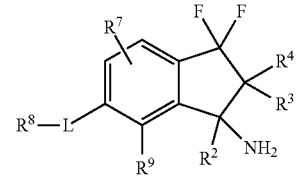
(VIIb)

In a first subembodiment of embodiment 37, the compound or a pharmaceutically acceptable salt thereof has the structure of formula (IIa). In a second subembodiment of embodiment 37, the compound or a pharmaceutically acceptable salt thereof has the structure of formula (IIb).

38. In embodiment 38, the compound of embodiment 22, or a pharmaceutically salt thereof has a structure of formula (IVa):

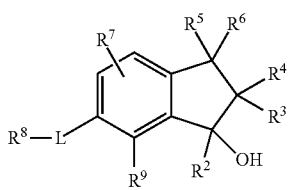
(IVa)

where $R^5$ and $R^6$ together with the carbon to which they are attached form cycloalkylene, preferably cyclopropylene, cyclobutylene or cyclopentylene optionally substituted with one or two fluoro.

39. In embodiment 39, the compound of embodiment 22, or a pharmaceutically salt thereof has a structure of formula (VIa) or (VIb):

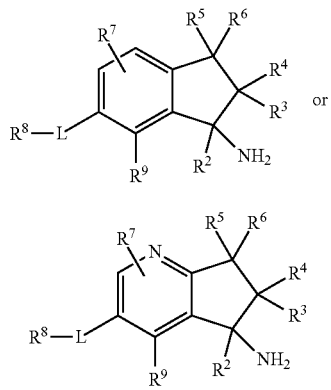
(VIa)

(VIb)

where $R^5$ and $R^6$ together with the carbon to which they are attached form cycloalkylene, preferably cyclopropylene, cyclobutylene or cyclopentylene optionally substituted with one or two fluoro. In a first subembodiment of embodiment 39, the compound or a pharmaceutically acceptable salt thereof has the structure of formula (VIa). In a second subembodiment of embodiment 39, the compound or a pharmaceutically acceptable salt thereof has the structure of formula (VIb).

40. In embodiment 40, the compound of embodiment 22, or a pharmaceutically acceptable salt thereof has a structure of formula (VIIa) or (VIIb):

In a first subembodiment of embodiment 40, the compound or a pharmaceutically acceptable salt thereof has the structure of formula (VIIa). In a second subembodiment of embodiment 40, the compound or a pharmaceutically acceptable salt thereof has the structure of formula (VIIb).

41. In embodiment 41, the compound of any one of embodiments 22 to 40 and subembodiments contained therein, or a pharmaceutical salt thereof is wherein $R^3$ fluoro.

42. In embodiment 42, the compound of any one of embodiments 22 to 40 and subembodiments contained therein, or a pharmaceutical salt thereof is wherein $R^3$ and $R^4$ are fluoro.

43. In embodiment 43, the compound of any one of embodiments 22 to 42 and subembodiments contained therein, or a pharmaceutical salt thereof is wherein L is O, S, SO, $SO_2$, or NH. In a first subembodiment of embodiment 43, L is O. In a second subembodiment of embodiment 43, L is S. In a third subembodiment of embodiment 43, L is NH. In a fourth subembodiment of embodiment 43, L is SO or $SO_2$.

44. In embodiment 44, the compound of any one of embodiments 22 to 42 and subembodiments contained therein, or a pharmaceutical salt thereof is wherein L is O.

45. In embodiment 45, the compound of any one of embodiments 22 to 44 and subembodiments contained therein, or a pharmaceutical salt thereof is wherein $R^8$ is cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl.

46. In embodiment 46, the compound of any one of embodiments 22 to 45 and subembodiments contained therein, or a pharmaceutical salt thereof is wherein $R^9$ is methyl, ethyl, methoxy, fluoro, bromo, cyano, cyclopropyl, trifluoromethyl, difluoromethyl, difluoromethoxy, trifluoromethoxy, or methylsulfonyl. In a first subembodiment of embodiment 46, $R^9$ is difluoromethyl, difluoromethoxy, trifluoromethyl, or trifluoromethoxy. In a second subembodiment of embodiment 46, $R^9$ is difluoromethyl.

47. In embodiment 47, the compound of any one of embodiments 22 to 46 and subembodiments contained therein, or a pharmaceutical salt thereof is wherein $R^8$ is phenyl substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl. In a first subembodiment of embodiment 47, $R^a$, $R^b$, and are independently selected from hydrogen, alkyl, alkoxy, hydroxy, halo, haloalkyl, haloalkoxy, and cyano. In a second subembodiment of embodiment 47, $R^a$, $R^b$, and $R^c$ are independently selected from hydrogen, methyl, methoxy, hydroxy, chloro, fluoro, cyano, difluoromethyl, trifluoromethyl, difluoromethoxy, and trifluoromethoxy 48. In embodiment 48, the compound of any one of embodiments 22 to 46 and subembodiments contained therein, or a pharmaceutical salt thereof is wherein $R^8$ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, or 3-cyano-5-difluoromethylphenyl. In a fourth subembodiment of embodiment 26, $R^{10}$ is 3-cyano-5-fluorophenyl.

49. In embodiment 49, the compound of any one of embodiments 22 to 46 and subembodiments contained therein, or a pharmaceutical salt thereof is wherein $R^8$ is cycloalkyl or cycloalkylalkyl each optionally substituted with one or two substituents independently selected from alkyl, halo, alkoxy, cyano, and hydroxy. In a first subembodiment of embodiment 49, $R^8$ is cyclopropylmethyl, cyclopropylethyl, cyclobutylmethyl, cyclobutylethyl, cyclopentylmethyl, cyclopentylethyl, or cyclohexylmethyl, each optionally substituted with one or two substituents independently selected from alkyl, halo, alkoxy, cyano, and hydroxy. In a second subembodiment of embodiment 49, $R^6$ is cyclopropylmethyl, cyclopropylethyl, cyclobutylmethyl, cyclobutylethyl, cyclopentylmethyl, cyclopentylethyl, or cyclohexylmethyl, each substituted with one or two substituents independently selected from hydrogen, methyl, methoxy, cyano, and fluoro, preferably $R^8$ is cyclopropylmethyl, 1-cyanocyclopropylmethyl, cyclobutylmethyl, 2-fluorocyclopropylmethyl, or 1-cyanocyclobutylmethyl. In a third subembodiment of embodiment 49, $R^8$ is cyclopropyl, cyclobutyl, cyclopentyl, or cyclohexyl, each optionally substituted with one or two substituents independently selected from alkyl, halo, alkoxy, cyano, and hydroxy. In a fourth subembodiment of embodiment 49, $R^8$ is cyclopropyl, cyclobutyl, cyclopentyl, or cyclohexyl, each optionally substituted with one or two substituents independently selected from methyl, cyano, methoxy, and fluoro, preferably, $R^8$ is cyclobutyl, 3-fluorocyclobutyl, 3,3-difluorocyclobutyl, 3-cyanocyclobutyl, 3-fluorocyclohexyl, or 3-cyano-3-methylcyclobutyl.

50. In embodiment 50, the compound of any one of embodiments 22 to 46 and subembodiments contained therein, or a pharmaceutical salt thereof is wherein $R^8$ is heteroaryl substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl. In a first subembodiment of embodiment 50, $R^8$ is 5- or 6-membered heteroaryl e.g., pyridyl, pyridazinyl, pyrimidinyl, thienyl, furanyl, thiazolyl, oxazolyl, imidazolyl, or pyrazinyl, each ring substituted with $R^a$, $R^b$, and/or $R^c$ wherein $R^a$ and $R^b$ are independently selected from hydrogen, alkyl, alkoxy, hydroxy, halo, haloalkyl, haloalkoxy, and cyano and $R^c$ is selected from hydrogen, alkyl, halo, haloalkyl, and haloalkoxy. In a second subembodiment of embodiment 50, $R^8$ is independently pyridin-3-yl, pyridin-2-yl, pyridazin-3-yl, pyridazin-4-yl, pyrimidin-5-yl, pyrimidin-2-yl, thien-2-yl, furan-2-yl, thiazol-5-yl, oxazol-5-yl, imidazol-5-yl, furan-3-yl thien-3-yl, thiazol-4-yl, pyridin-4-yl, oxazol-2-yl, imidazol-2-yl, pyridin-2-yl, pyrazin-2-yl or thiazol-2-yl, each ring substituted with $R^a$, $R^b$, and/or $R^c$ wherein $R^a$ and $R^b$ are independently selected from hydrogen, methyl, methoxy, hydroxy, chloro, fluoro, difluoromethyl, trifluoromethyl, difluoromethoxy, and trifluoromethoxy and $R^c$ is selected from hydrogen, methyl, cyano, chloro, fluoro, difluoromethyl, trifluoromethyl, difluoromethoxy, and trifluoromethoxy. In a third subembodiment of embodiment 50, $R^8$ is 5-cyanopyridin-3-yl, 5-chloropyridin-3-yl, or 5-fluoropyridin-3-yl.

51. In embodiment 51, the compound of any one of embodiments 22 to 50 and subembodiments contained therein, or a pharmaceutical salt thereof is wherein $R^7$ is hydrogen, methyl, ethyl, methoxy, fluoro, trifluoromethyl or trifluoromethoxy. In a first subembodiment of embodiment 51, $R^7$ is hydrogen.

52. In embodiment 52, the compound of any one of embodiments 22 to 51 and subembodiments contained therein, or a pharmaceutical salt thereof is wherein $R^2$ is hydrogen, methyl, or ethyl. In a first subembodiment of embodiment 52, $R^2$ is hydrogen.

Representative compounds of the disclosure made are disclosed in Table I below:

TABLE I

| Cpd # | Structure | Name |
|---|---|---|
| I-1 | 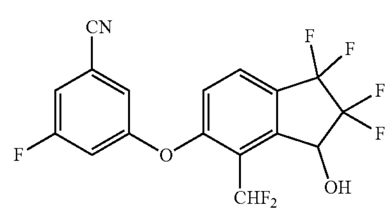 [SMILES: N#Cc1cc(F)cc(Oc2ccc3c(c2C(F)F)C(O)C(F)(F)C3(F)F)c1] | 3-((4-(difluoromethyl)-1,1,2,2-tetrafluoro-3-hydroxy-2,3-dihydro-1H-inden-5-yl)oxy)-5-fluorobenzonitrile |

TABLE I-continued

| Cpd # | Structure | Name |
|---|---|---|
| I-1a | 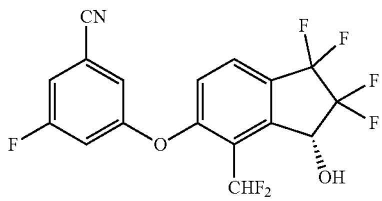 | (R)-3-((4-(difluoromethyl)-1,1,2,2-tetrafluoro-3-hydroxy-2,3-dihydro-1H-inden-5-yl)oxy)-5-fluorobenzonitrile |
| I-1b | 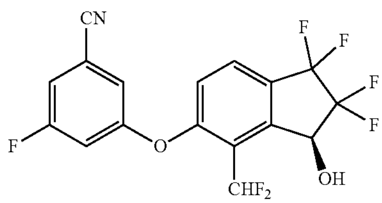 [SMILES: N#Cc1cc(F)cc(Oc2ccc3c(c2C(F)F)[C@H](O)C(F)(F)C3(F)F)c1] | (S)-3-((4-(difluoromethyl)-1,1,2,2-tetrafluoro-3-hydroxy-2,3-dihydro-1H-inden-5-yl)oxy)-5-fluorobenzonitrile |
| I-1c | 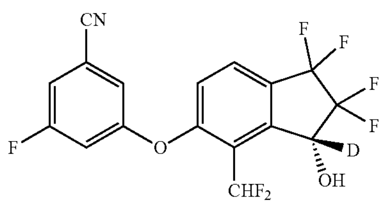 [SMILES: [2H][C@@]1(O)c2c(ccc(Oc3cc(F)cc(C#N)c3)c2C(F)F)C(F)(F)C1(F)F] | (R)-3-((4-(difluoromethyl)-1,1,2,2-tetrafluoro-3-hydroxy-2,3-dihydro-1H-inden-5-yl-3-d)oxy)-5-fluorobenzonitrile |
| I-1d | 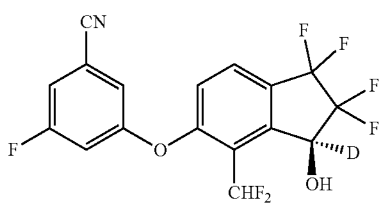 [SMILES: [2H][C@]1(O)c2c(ccc(Oc3cc(F)cc(C#N)c3)c2C(F)F)C(F)(F)C1(F)F] | (S)-3-((4-(difluoromethyl)-1,1,2,2-tetrafluoro-3-hydroxy-2,3-dihydro-1H-inden-5-yl-3-d)oxy)-5-fluorobenzonitrile |
| I-2 | 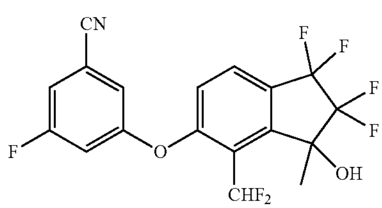 [SMILES: CC1(O)c2c(ccc(Oc3cc(F)cc(C#N)c3)c2C(F)F)C(F)(F)C1(F)F] | 3-((4-(difluoromethyl)-1,1,2,2-tetrafluoro-3-hydroxy-3-methyl-2,3-dihydro-1H-inden-5-yl)oxy)-5-fluorobenzonitrile |
| I-3 | 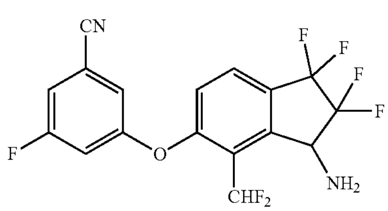 [SMILES: N#Cc1cc(F)cc(Oc2ccc3c(c2C(F)F)C(N)C(F)(F)C3(F)F)c1] | 3-((3-amino-4-(difluoromethyl)-1,1,2,2-tetrafluoro-2,3-dihydro-1H-inden-5-yl)oxy)-5-fluorobenzonitrile |
| I-3a | 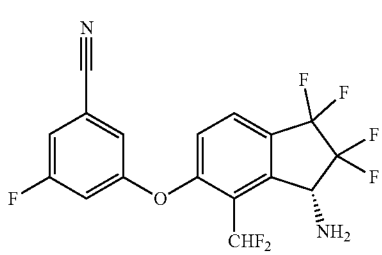 | (R)-3-((3-amino-4-(difluoromethyl)-1,1,2,2-tetrafluoro-2,3-dihydro-1H-inden-5-yl)oxy)-5-fluorobenzonitrile |

TABLE I-continued

| Cpd # | Structure | Name |
|---|---|---|
| I-3b | 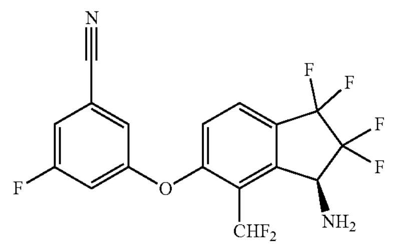 [SMILES: N#Cc1cc(F)cc(Oc2ccc3c(c2C(F)F)[C@H](N)C(F)(F)C3(F)F)c1] | (S)-3-((3-amino-4-(difluoromethyl)-1,1,2,2-tetrafluoro-2,3-dihydro-1H-inden-5-yl)oxy)-5-fluorobenzonitrile |
| I-4 | 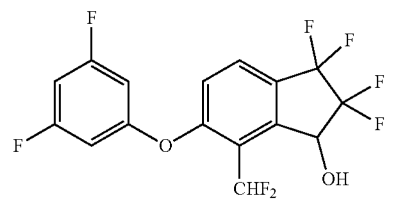 | 7-(difluoromethyl)-6-(3,5-difluorophenoxy)-2,2,3,3-tetrafluoro-2,3-dihydro-1H-inden-1-ol |
| I-5 | 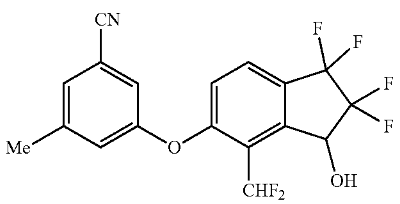 [SMILES: Cc1cc(C#N)cc(Oc2ccc3c(c2C(F)F)C(O)C(F)(F)C3(F)F)c1] | 3-((4-(difluoromethyl)-1,1,2,2-tetrafluoro-3-hydroxy-2,3-dihydro-1H-inden-5-yl)oxy)-5-methylbenzonitrile |
| I-6 | 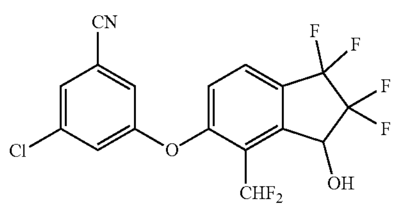 [SMILES: N#Cc1cc(Cl)cc(Oc2ccc3c(c2C(F)F)C(O)C(F)(F)C3(F)F)c1] | 3-chloro-5-((4-(difluoromethyl)-1,1,2,2-tetrafluoro-3-hydroxy-2,3-dihydro-1H-inden-5-yl)oxy)benzonitrile |
| I-7 | 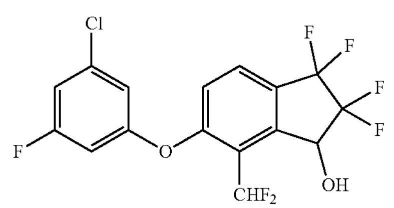 [SMILES: OC1c2c(ccc(Oc3cc(F)cc(Cl)c3)c2C(F)F)C(F)(F)C1(F)F] | 6-(3-chloro-5-fluorophenoxy)-7-(difluoromethyl)-2,2,3,3-tetrafluoro-2,3-dihydro-1H-inden-1-ol |
| I-8 | 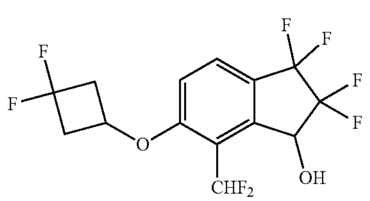 [SMILES: OC1c2c(ccc(OC3CC(F)(F)C3)c2C(F)F)C(F)(F)C1(F)F] | 6-(3,3-difluorocyclobutoxy)-7-(difluoromethyl)-2,2,3,3-tetrafluoro-2,3-dihydro-1H-inden-1-ol |
| I-9 | 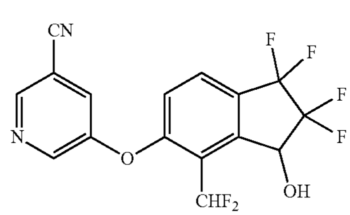 [SMILES: N#Cc1cncc(Oc2ccc3c(c2C(F)F)C(O)C(F)(F)C3(F)F)c1] | 5-((4-(difluoromethyl)-1,1,2,2-tetrafluoro-3-hydroxy-2,3-dihydro-1H-inden-5-yl)oxy)nicotinonitrile |

TABLE I-continued

| Cpd # | Structure | Name |
|---|---|---|
| I-10 | 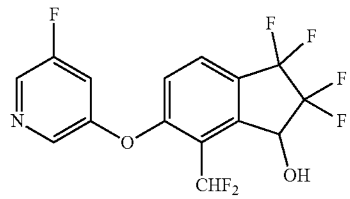 [SMILES: OC1c2c(ccc(Oc3cncc(F)c3)c2C(F)F)C(F)(F)C1(F)F] | 7-(difluoromethyl)-2,2,3,3-tetrafluoro-6-((5-fluoropyridin-3-yl)oxy)-2,3-dihydro-1H-inden-1-ol |
| I-11a | 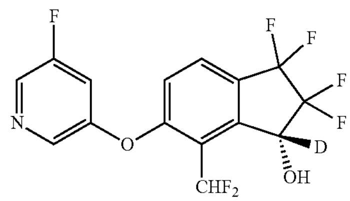 [SMILES: [2H][C@@]1(O)c2c(ccc(Oc3cncc(F)c3)c2C(F)F)C(F)(F)C1(F)F] | (R)-7-(difluoromethyl)-2,2,3,3-tetrafluoro-6-((5-fluoropyridin-3-yl)oxy)-2,3-dihydro-1H-inden-1-d-1-ol |
| I-11b | 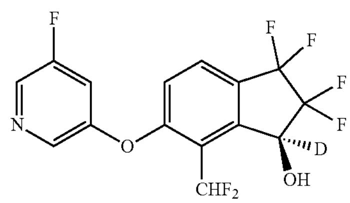 [SMILES: [2H][C@]1(O)c2c(ccc(Oc3cncc(F)c3)c2C(F)F)C(F)(F)C1(F)F] | (S)-7-(difluoromethyl)-2,2,3,3-tetrafluoro-6-((5-fluoropyridin-3-yl)oxy)-2,3-dihydro-1H-inden-1-d-1-ol |
| I-12a | 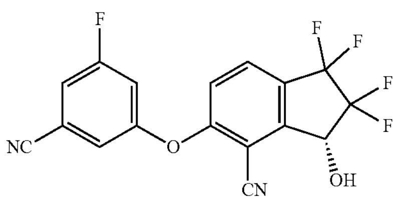 [SMILES: N#Cc1cc(F)cc(Oc2ccc3c(c2C#N)[C@@H](O)C(F)(F)C3(F)F)c1] | (R)-5-(3-cyano-5-fluorophenoxy)-1,1,2,2-tetrafluoro-3-hydroxy-2,3-dihydro-1H-indene-4-carbonitrile |
| I-12b | 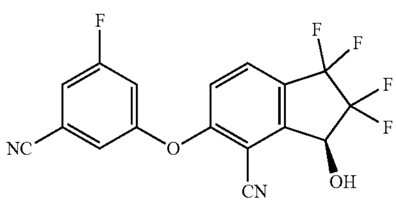 [SMILES: N#Cc1cc(F)cc(Oc2ccc3c(c2C#N)[C@H](O)C(F)(F)C3(F)F)c1] | (S)-5-(3-cyano-5-fluorophenoxy)-1,1,2,2-tetrafluoro-3-hydroxy-2,3-dihydro-1H-indene-4-carbonitrile |
| I-13b | 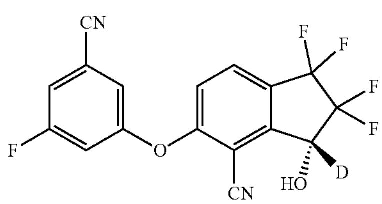 [SMILES: [2H][C@@]1(O)c2c(ccc(Oc3cc(F)cc(C#N)c3)c2C#N)C(F)(F)C1(F)F] | (R)-5-(3-cyano-5-fluorophenoxy)-1,1,2,2-tetrafluoro-3-hydroxy-2,3-dihydro-1H-indene-4-carbonitrile-3-d |
| I-13a | 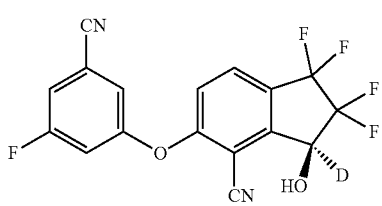 [SMILES: [2H][C@]1(O)c2c(ccc(Oc3cc(F)cc(C#N)c3)c2C#N)C(F)(F)C1(F)F] | (S)-5-(3-cyano-5-fluorophenoxy)-1,1,2,2-tetrafluoro-3-hydroxy-2,3-dihydro-1H-indene-4-carbonitrile-3-d |

TABLE I-continued

| Cpd # | Structure | Name |
|---|---|---|
| I-14 | 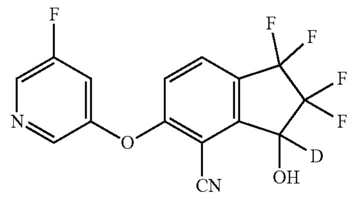 [SMILES: [2H]C1(O)c2c(ccc(Oc3cncc(F)c3)c2C#N)C(F)(F)C1(F)F] | 1,1,2,2-tetrafluoro-5-((5-fluoropyridin-3-yl)oxy)-3-hydroxy-2,3-dihydro-1H-indene-4-carbonitrile-3-d |
| I-15 | 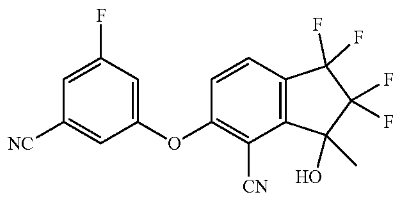 [SMILES: CC1(O)c2c(ccc(Oc3cc(F)cc(C#N)c3)c2C#N)C(F)(F)C1(F)F] | 5-(3-cyano-5-fluorophenoxy)-1,1,2,2-tetrafluoro-3-hydroxy-3-methyl-2,3-dihydro-1H-indene-4-carbonitrile |
| I-16 | 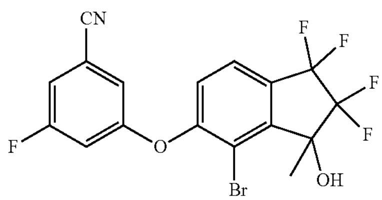 [SMILES: CC1(O)c2c(ccc(Oc3cc(F)cc(C#N)c3)c2Br)C(F)(F)C1(F)F] | 3-((4-bromo-1,1,2,2-tetrafluoro-3-hydroxy-3-methyl-2,3-dihydro-1H-inden-5-yl)oxy)-5-fluorobenzonitrile |
| I-17 | 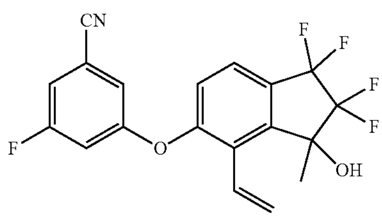 [SMILES: C=Cc1c(Oc2cc(F)cc(C#N)c2)ccc2c1C(C)(O)C(F)(F)C2(F)F] | 3-fluoro-5-((1,1,2,2-tetrafluoro-3-hydroxy-3-methyl-4-vinyl-2,3-dihydro-1H-inden-5-yl)oxy)benzonitrile |
| I-18 | 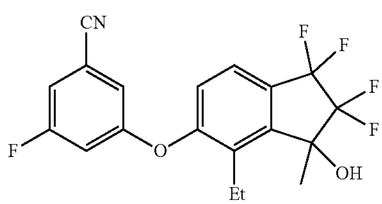 [SMILES: CCc1c(Oc2cc(F)cc(C#N)c2)ccc2c1C(C)(O)C(F)(F)C2(F)F] | 3-((4-ethyl-1,1,2,2-tetrafluoro-3-hydroxy-3-methyl-2,3-dihydro-1H-inden-5-yl)oxy)-5-fluorobenzonitrile |
| I-19 | 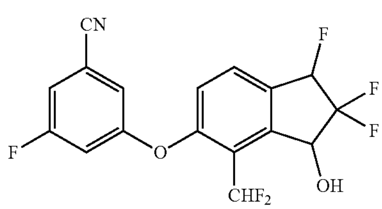 [SMILES: N#Cc1cc(F)cc(Oc2ccc3c(c2C(F)F)C(O)C(F)(F)C3F)c1] | 3-((4-(difluoromethyl)-1,2,2-trifluoro-3-hydroxy-2,3-dihydro-1H-inden-5-yl)oxy)-5-fluorobenzonitrile |
| I-20 | 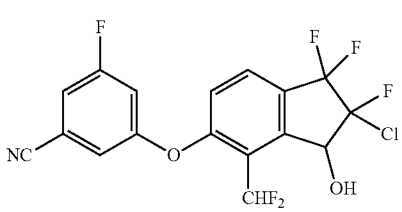 [SMILES: N#Cc1cc(F)cc(Oc2ccc3c(c2C(F)F)C(O)C(F)(Cl)C3(F)F)c1] | 3-((2-chloro-4-(difluoromethyl)-1,1,2-trifluoro-3-hydroxy-2,3-dihydro-1H-inden-5-yl)oxy)-5-fluorobenzonitrile |

TABLE I-continued

| Cpd # | Structure | Name |
|---|---|---|
| I-21a | 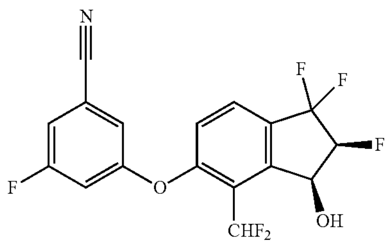 [SMILES: N#Cc1cc(F)cc(Oc2ccc3c(c2C(F)F)[C@H](O)[C@H](F)C3(F)F)c1] | rac-3-(((2S,3S)-4-(difluoromethyl)-1,1,2-trifluoro-3-hydroxy-2,3-dihydro-1H-inden-5-yl)oxy)-5-fluorobenzonitrile |

Additional representative compounds of Formula (I) that can be prepared are shown in Table II below:

TABLE 2

| | Structure | Name |
|---|---|---|
| II-1 | 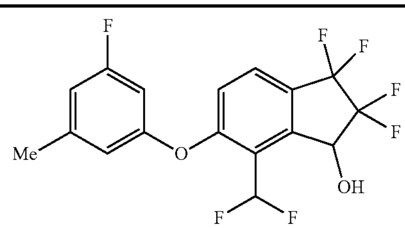 | 7-(difluoromethyl)-2,2,3,3-tetrafluoro-6-(3-fluoro-5-methylphenoxy)-2,3-dihydro-1H-inden-1-ol |
| II-2 | 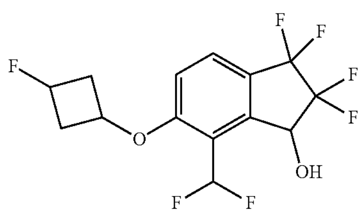 [SMILES: OC1c2c(ccc(OC3CC(F)C3)c2C(F)F)C(F)(F)C1(F)F] | 7-(difluoromethyl)-2,2,3,3-tetrafluoro-6-(3-fluorocyclobutoxy)-2,3-dihydro-1H-inden-1-ol |
| II-3 | 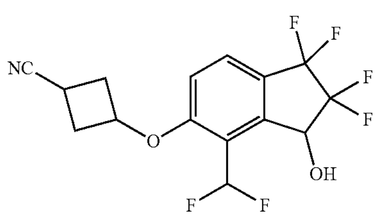 [SMILES: N#CC1CC(Oc2ccc3c(c2C(F)F)C(O)C(F)(F)C3(F)F)C1] | 3-((4-(difluoromethyl)-1,1,2,2-tetrafluoro-3-hydroxy-2,3-dihydro-1H-inden-5-yl)oxy)cyclobutane-1-carbonitrile |
| II-4 | 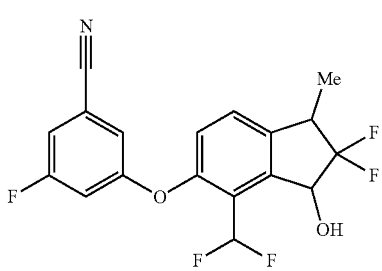 [SMILES: CC1c2ccc(Oc3cc(F)cc(C#N)c3)c(C(F)F)c2C(O)C1(F)F] | 3-((4-(difluoromethyl)-2,2-difluoro-3-hydroxy-1-methyl-2,3-dihydro-1H-inden-5-yl)oxy)-5-fluorobenzonitrile |
| II-5 | 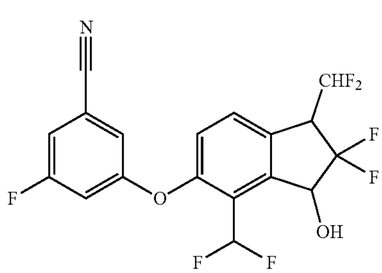 [SMILES: N#Cc1cc(F)cc(Oc2ccc3c(c2C(F)F)C(O)C(F)(F)C3C(F)F)c1] | 3-((1,4-bis(difluoromethyl)-2,2-difluoro-3-hydroxy-2,3-dihydro-1H-inden-5-yl)oxy)-5-fluorobenzonitrile |

TABLE 2-continued

II-6

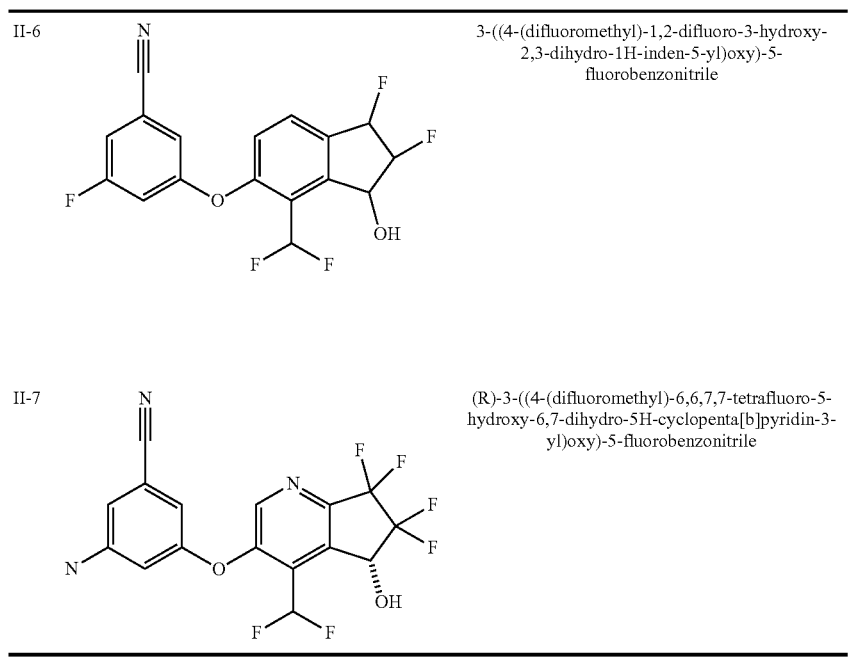

3-((4-(difluoromethyl)-1,2-difluoro-3-hydroxy-2,3-dihydro-1H-inden-5-yl)oxy)-5-fluorobenzonitrile

II-7

(R)-3-((4-(difluoromethyl)-6,6,7,7-tetrafluoro-5-hydroxy-6,7-dihydro-5H-cyclopenta[b]pyridin-3-yl)oxy)-5-fluorobenzonitrile General Synthetic Scheme Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I) where $X^1$ is CH, and $R^1$, $R^2$, $R^3$, $R^4$, $R^5$, $R^6$, $R^7$, $R^8$ and $R^9$ are as defined in the Summary can be prepared as illustrated and described in Scheme 1 below.

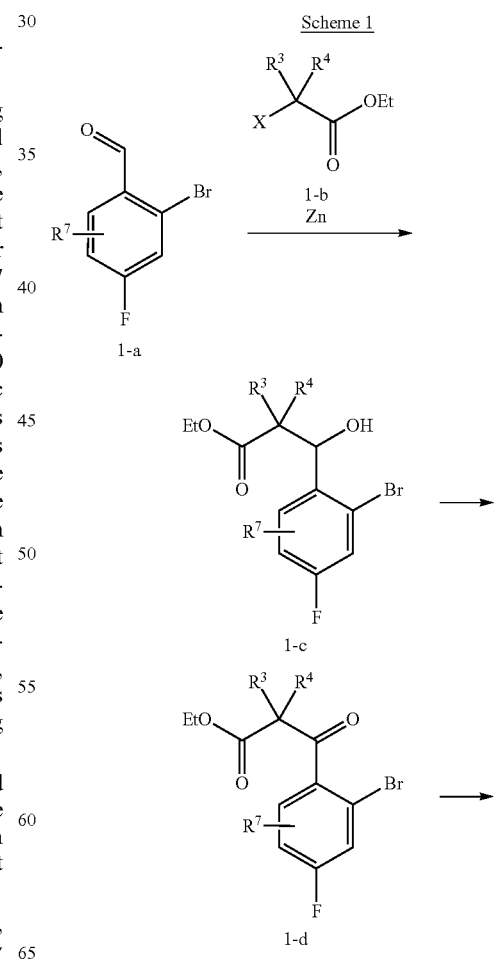

Scheme 1

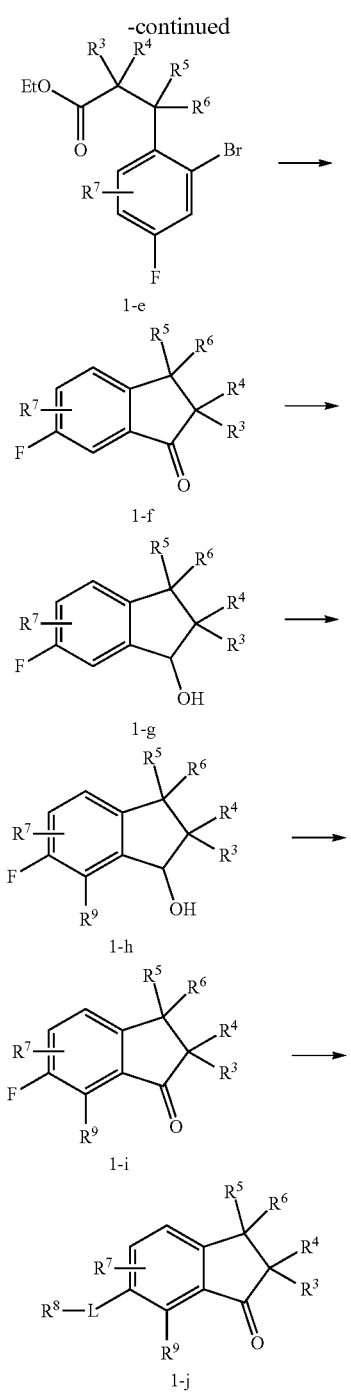

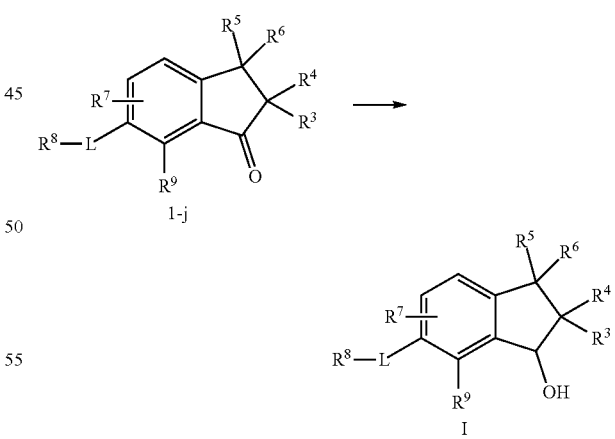

zoic acid (IBX) to give a ketone of formula 1-d. The keto group in compound of formula 1-d can be functionalized to provide compound of formula 1-e where $R^5$ and $R^6$ are as described in the Summary by methods well known in the art. For example, a compound of formula 1-e where $R^5$ and $R^6$ are fluoro can be synthesized from 1-d by treatment with a fluorinating agent such as DAST under conditions well known in the art. Cyclization of 1-e can be achieved by treating it with alkyl lithium reagent such n-BuLi to give ketone 1-f. The carbonyl group in 1-f can be reduced with reducing reagents such as $NaBH_4$ to provide alcohol 1-g. Compounds of formula 1-g can be coverted to compounds of formula 1-h where $R^9$ is as described in the Summary by methods well known in the art. For example, lithiation of 1-g, followed by treatment of the lithio intermediate with formaldehyde followed by fluorination of the resulting aldehyde provides compounds of formula 1-h where $R^9$ is difluoromethane. Oxidation of 1-h with oxidative reagents such as IBX provides ketone of formula 1-i. The fluoro group in compounds of formulae 11-i is converted to a group of formula $-L-R^8$ where L and $R^8$ are as described in the Summary by treating compound 1-i with a compound of formula $R^8$-LH where L is N, O, or S and $R^8$ is a defined in the Summary by method well known in the art. Compounds of formula $R^8$-LH are commercially available or they can be prepared by methods well known in the art. For example, 3-fluoro-5-hydroxybenzonitrile, 3,5-difluorophenol, 3-chloro-5-fluorophenol, 3-chloro-5-hydroxy-benzonitrile, 5-fluoropyridin-3-ol, 5-chloropyridin-3-ol, 5-hydroxynicotinonitrile, 3-fluoro-5-mercaptobenzonitrile, 3-amino-5-fluorobenzonitrile, 3,3-difluorocyclobutan-1-ol, 3-amino-5-fluorobenzonitrile, 3-fluoro-5-mercaptobenzonitrile, 3-chloro-5-mercaptobenzonitrile, 3-amino-5-chlorobenzonitrile are commercially available.

Compounds of Formula (I) with $R^1$ and $R^2$ as described in the Summary can be synthesized from the compounds of Formula 1-j by further functionalizing the carbonyl group. Some illustrative examples are provided below.

Method (i)

Reformastky reaction between an aldehyde of formula 1-a where $R^7$ is as described in the Summary or a precursor group thereof and a compound of formula 1-b where X is halide and $R^3$ and $R^4$ are independently hydrogen, deuterium, alkyl, halo, haloalkyl, hydroxyalkyl, or alkoxyalkyl, mediated by Zinc metal provides a compound of formula 1-c. Compounds of formula 1-a and 1-b are commercially available or they can be prepared by methods well known in the art. For example, 2-bromo-4-fluorobenzaldehyde, ethyl 2-bromo-2,2-difluoroacetate, ethyl 2-bromo-2-methylpropanoate, ethyl 2-bromopropanoate, ethyl 2-bromoacetate are commercially available. The hydroxyl group in 1-c can be oxidized under oxidative conditions such as 2-iodoxyben- A compound of Formula (I) where $R^1$ is hydroxyl group and $R^2$ is hydrogen can be synthesized by treating 1-j with a suitable reducing agent such as sodium borohydride or under transfer hydrogenation conditions well known in the art. Asymmetric reduction can also achieved. Examples of chemical asymmetric reduction of ketone include but not limited to CBS reduction, asymmetric hydrogenation and asymmetric transfer hydrogenation. For examples of methods and catalysts for ruthenium catalyzed transfer hydrogenation, see U.S. Pat. Nos. 6,184,381 and 6,887,820. Exemplary catalysts for asymmetric hydrogenation include, but are not limited to RuCl(P-cymene)[(S,S)-Ts-DPEN], RuCl(P-cymene)[(R,R)-Ts-DPEN].

Method (ii)

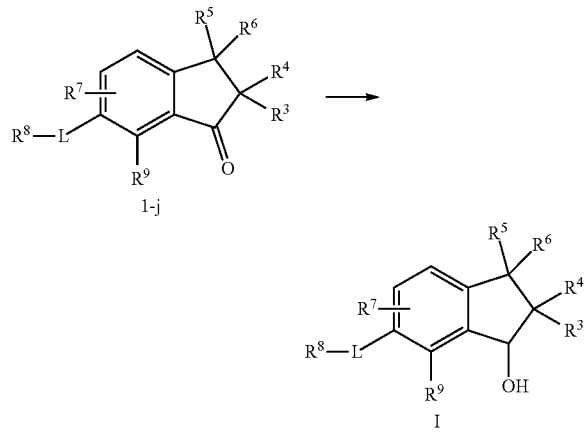

A compound of Formula (I) where $R^1$ is hydroxyl group and and $R^2$ is an alkyl group can be can be prepared by treating 1-j with an alkyl Grignard reagent under conditions well known in the art.

Method (iii)

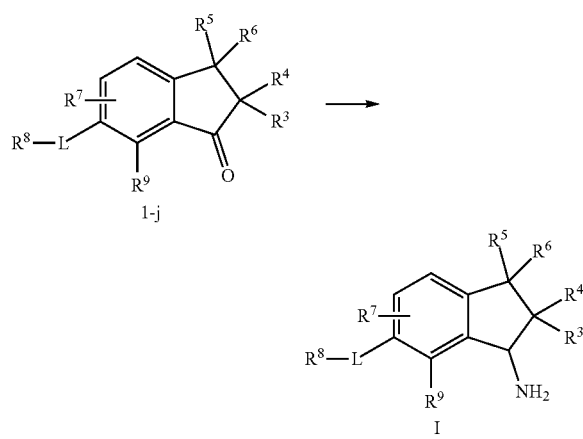

A compound of Formula (I) where $R^1$ is amine group and $R^2$ is hydrogen can be synthesized by treating 1-j under reductive amination conditions well known in the art. For example, reaction of 1-j with ammonium followed by treating the resulting mixture with sodium borohydride.

Utility

The compounds disclosed herein are useful for the treatment of HIF-2α mediated diseases, which include but are not limited to, various types of cancer, liver disease such as nonalcoholic steatohepatitis (NASH), inflammatory disease such as inflammatory bowel disease (IBD), pulmonary diseases such as pulmonary arterial hypertension (PAH), and iron load disorders.

HIF-2α plays an important role in the initiation and progression of many human cancers. Many extensive studies have demonstrated the role of increased HIF-2α activity in driving clear cell renal cell carcinoma (ccRCC) (see review by Shen and Kaelin, Seminars in Cancer Biology 23: 18-25, 2013). Abnormal HIF-2α activity is largely due to loss of function of a tumor suppressor, VHL. It is known that over eighty percent of ccRCC have defective VHL either through deletion, mutation or disturbed post-translational modification. Defective VHL leads to constitutively active HIF-2α proteins regardless of oxygen level. Various studies employing gain-of-function and loss-of-function approaches in mouse models have demonstrated that HIF-2α is an oncogenic substrate of VHL (see Kondo, et al. *Cancer Cell* 2002, 1, 237-246; Kondo, et al. *PLoS Biology* 2002, 1, 439-444; Maranchi, et al. *Cancer Cell* 2002, 1, 247-255; Zimmer, et al. *Mol. Cancer Res* 2004, 2, 89-95). For example, knockdown of HIF-2α in VHL-null tumors inhibited tumor formation; while reintroduction of VHL and overexpression of HIF-2α overcame the tumor suppressive role of VHL. Moreover, single nucleotide polymorphism in HIF-2α, is associated with resistant to PHD-mediated degradation, has been linked to an increased risk of developing RCC. In addition to serving as an archetypical tumor-initiating event in ccRCC, the VHL-HIF-2α axis has also been implicated in ccRCC tumor metastasis through its downstream CXCR4 and CYTIP (see Vanharanta et al. *Nature Medicine* 2013, 19, 50-59; Peter Staller et al. *Nature.* 2003 Sep. 18, 425(6955), 307-11). Taken together, these studies support the potential therapeutic utility of HIF-2a targeted agents for the treatment of ccRCC.

Defective VHL not only predisposes patients to kidney cancer (with a 70% lifetime risk), but also to hemangioblastomas, pheochromocytoma, endolymphatic sac tumors and pancreatic neuroendocrine tumors. Tumors derived from defective VHL are frequently driven by the constitutively active downstream HIF-α proteins, with the majority of these dependent on HIF-2α activity (see Maher, et al. *Eur. J Hum. Genet.* 2011, 19, 617-623). Both genetic and epigenetic mechanisms can lead to the loss of function in VHL. Epigenetic inactivation of VHL expression and thus constitutive activation of HIF-α proteins has been found in many cancers including RCC, multiple myeloma, retinoblastoma, NSCLC, pancreatic endocrine tumors, squamous cell carcinoma, acute myeloid leukemia, myelodysplastic syndrome, and esophageal squamous cell carcinoma (see reviewed in Nguyen, et al. *Arch. Phann. Res* 2013, 36: 252-263). HIF-2α has also been linked to cancers of the retina, adrenal gland and pancreas through both loss of function in VHL and activating mutations in HIF-2α. Recently, gain-of-function HIF-2α mutations have been identified in erythrocytosis and paraganglioma with polycythemia (see Zhuang, et al. *NEJM* 2012, 367, 922-930; Percy, et al. *NEJM* 2008, 358: 162-168; and Percy, et al. *Am. J. Hematol.* 2012, 87: 439-442). Notably, many of the known HIF-2α target gene products (e.g., VEGF, PDGF, and cyclin DI) have been demonstrated to play pivotal roles in cancers derived from kidney, liver, colon, lung, and brain. Thus, a HIF-2α targeted therapy could be beneficial for the above cancers. In addition to loss of function in VHL and activating mutation of HIF-2α, HIF-α proteins are also frequently upregulated in the intratumor environment of rapidly growing tumors, due to the hypoxic condition resulting from poor vascularization in large tumors. The activated HIF-α pathways, in turn, further promotes tumor cell survival and proliferation by transcriptionally upregulating various essential factors.

A large body of studies have demonstrated a correlation between HIF-2α overexpression and poor prognosis in various cancers including cancers of astrocytoma, breast, cervical, colorectal, glioblastoma, glioma, head and neck, liver, non-small cell lung, melanoma, neuroblastoma, ovarian, and prostate, thereby supporting the pursuit of HIF-2α as a therapeutic target in treating these cancers (see reviewed in Keith, et al. *Nature Rev. Cancer* 2012, 12, 9-22). HIF-2α has been demonstrated to augment the growth of APC mutant colorectal cancer through its regulation of genes involved in proliferation, iron utilization and inflammation (see Xue, et al. *Cancer Res* 2012, 72: 2285-2293; and Xue and Shah, Carcinogenesis 2013, 32: 163-169). In hepatocellular carcinoma (HCC), knock-down of HIF-2α in preclinical models led to the inhibition of cell proliferation in vitro and tumor growth in vivo through the downregulation of VEGF and cyclin D 1 (see He, et al. *Cancer Sci.* 2012, 103: 528-534). In NSCLC, around 50% of patients exhibited overexpression of HIF-2α protein, which strongly correlates with higher VEGF expression and reduced overall survival. On the other hand, HIF-1α does not correlate with reduced overall survival in lung cancer patients even though its expression is also often increased (see Giatromanolaki, et al. *Br. J. Cancer* 2001, 85: 881-890,). Extensive studies in mice engineered with both non-degradable HIF-2α and mutant KRAS tumors have demonstrated an increased tumor burden and a decreased survival when compared to mice with only mutant KRAS expression (see Kim, et al. *J. Clin. Invest.* 2009, 119: 2160-2170). These studies demonstrate that HIF-2α promotes tumor growth and progression in lung cancer, and also negatively correlates with clinical prognosis.

HIF-2αs activity also has been linked to the progression of chronic obstructive pulmonary disease (COPD), in addition to lung cancer, in mouse models (see Karoor, et al. *Cancer Prev. Res.* 2012, 5: 1061-1071). HIF-2α activity has also been demonstrated to be important in cancers of the central nervous system (see Holmquist-Mengelbier, et al. *Cancer Cell* 2006, 10: 413-423 and Li, et al. *Cancer Cell* 2009, 15: 501-513). HIF-2α knockdown reduced tumor growth in preclinical animal models of neuroblastoma, Conversely, increased level of HIF-2α correlated with advanced disease, poor prognosis and higher VEGF levels, which likely contribute to the poor clinical outcome. Similarly, higher HIF-2α expression has been correlated with a poor survival in glioma. Experimentally, inhibition of HIF-2α in glioma stem cells reduced cell proliferation and survival in vitro and tumor initiation in vivo. Interestingly, while HIF-1α is expressed in both neural progenitors and brain tumor stem cells, HIF-2α is found exclusively in the latter. Moreover, survival of glioma patients correlates to with HIF-2α, but not HIF-1α level.

Radiation therapy is frequently used for approximately 50% of cancer patients, either alone or in combination with other therapies. However, the hypoxia microenvironment within the tumor has long been associated with resistance to radiation therapy. Bhatt and co-workers found that decreased level of HIF-2α leads to increased sensitivity to ionizing radiation in renal cell carcinoma cell lines (see Bhatt, et al. *BJU Int.* 2008, 102: 358-363). Furthermore, mechanistic studies from Bertout et. al, have demonstrated that HIF-2α inhibition enhances the effectiveness of radiation through increased p53-dependent apoptosis (see Bertout, et al. *PNAS* 2009, 106: 14391-14396). Thus, HIF-2α targeted therapy, such as HIF-2α inhibitors, could improve the response to radiation therapy in various cancers.

In addition to a direct role in promoting the initiation, progression and metastasis of tumor cells (e.g. ccRCC), HIF-2α also indirectly contributes to tumorigenesis through augmenting the immunosuppressive effect of hypoxia within the tumor microenvironment. Expression of HIF-2α has been detected in cells of the myeloid lineage (see Talks K L, et al. *Am J Pathol.* 2000, 157(2): 411-421). For example, HIF-2α is shown to favor the polarization of macrophages to the immunosuppressive M2 phenotype and enhances migration and invasion of tumor-associated macrophages (see Imtiyaz H Z et al. *J Clin Invest.* 2010, 120(8): 2699-2714). Thus, increased level of HIF-2α in tumor-associated macrophages (TAMs) is associated with high-grade human tumors and more importantly, correlates with poor prognosis. Furthermore, HIF-2α can indirectly promote additional immunosuppressive pathways (e.g. adenosine and arginase etc.) by modulating the expression of key signaling regulators such as adenosine A2B/A2A receptors and arginase. These data strongly support that HIF-2α is a potential therapeutic target for treating a broader range of inflammatory disorders and cancer either as a single agent or in combination with other therapeutic agents e.g., immunotherapies.

Due to the key roles of HIF-α proteins in regulating physiological response to the fluctuation of oxygen levels, they have been causally associated with many hypoxia-related pathological processes in addition to cancer. One such disease is PAH, a debilitating and life-threatening disease with very poor prognosis. Recent studies demonstrated that HIF-2α contributes to the process of hypoxic pulmonary vascular remodeling, reduced plasticity of the vascular bed, and ultimately, debilitating PAH (see Andrew S., et al. *Proc Natl Acad Sci USA.* 2016 Aug. 2; 113(31): 8801-8806, Tang H, et al. *Am J Physiol Lung Cell Mol Physiol.* 2018 Feb. 1, 314(2): L256-L275.). These studies offer a new understanding in the role of pulmonary endothelial HIF-2α in regulating the pulmonary vascular response to hypoxia, and provide a new therapeutic strategy by targeting HIF-2α. Another example of hypoxia-related pathological processes is IBD, a chronic relapsing inflammatory disease of the intestine. It has been found that intestinal inflammation and subsequently IBD, arose when a dysregulated epithelial oxygen tension occurs and intensifies across epithelial villi in the intestine (see Shah Y. M., *Molecular and Cellular Pediatrics,* 2016 December; 3(1):1). Interestingly, HIF-2α activation contributes to IBD, while HIF-1α in intestinal epithelial cells is considered as a major protective factor in IBD (see Karhausen J, et al. *J Clin Invest.* 2004; 114(8): 1098-1106; Furuta G T, et al. *J Exp Med.* 2001; 193(9): 1027-1034). Mechanistically, HIF-2α activation not only leads to the upregulation of pro-inflammatory cytokines which promotes IBD directly, but also results in loss of intestine barrier integrity, thus indirectly contributes to the manifestation of IBD. (see Xue X, et al. *Gastroenterology* 2013; 145(4): 831-841; Glover L E, et al. *Proc Natl Acad Sci USA.* 2013, 110(49): 19820-19825). Therefore, a HIF-2α inhibitor holds promise of reverting the pro-inflammatory condition and increasing the intestinal barrier integrity, thus alleviating the symptoms of IBD.

HIF-2α inhibitors also represents a novel therapeutic approach in NASH, for which limited therapeutic options are available. An elegant study recently showed that an intestine-specific disruption of HIF-2α led to a significant reduction of hepatic steatosis and obesity induced by high-fat-diet. Mechanistically, intestine HIF-2α positively regulates the gene encoding neuraminidase 3, which in turn regulates ceramide metabolism which contributes to the development of NASH (see Xie C, et al. *Nat Med.* 2017 November; 23(11): 1298-1308.). Therefore, a HIF-2α inhibitor will have preventive and therapeutic effects on metabolic disorders, such as NASH.

Several connections between the level of HIF-α and iron homeostasis have been identified (see Peyssonnaux C et al., *Cell Cycle* 2008; 7(1): 28-32). In particular, multiple studies have demonstrated the important role of HIF-2α in iron load disorders. Interestingly, HIF-2α, not HIF-1α, has emerged as an important "local" regulator of intestinal iron status through its regulation of various genes essential in iron transport and absorption (see Mastrogiannaki M, et al. *J Clin Invest.* 2009; 119(5): 1159-1166). Therefore, a HIF-2α inhibitor may also be useful in improving iron homeostasis in patients with iron disorders.

Accordingly, the present invention provides a method for treating the severity of a disease, condition, or disorder where activation or over activation of HIF-2α is implicated in the disease state. In one aspect, the present disclosure provides a method of treating renal cell carcinoma of a subject with a compound of Formula (I) or (I'), or a pharmaceutically acceptable salt thereof. HIF-2α inhibitors of Formula (I) or (I'), or a pharmaceutically acceptable salt thereof also have therapeutic potentials for a broad range of non-cancer indications including but not limited to NASH, IBD, PAH, and iron overload.

Testing

The HIF2α inhibitory activity of the compounds of Formula (I) or (I'), or a pharmaceutically acceptable salt thereof can be tested using the in vitro assay described in Biological Examples 1 below.

Pharmaceutical Compositions

In general, the compounds of Formula (I) or (I'), or a pharmaceutically acceptable salt thereof will be administered in a therapeutically effective amount by any of the accepted modes of administration for agents that serve similar utilities. Therapeutically effective amounts of compounds Formula (I) or (I'), or a pharmaceutically acceptable salt thereof may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of Formula (I) or (I'), or a pharmaceutically acceptable salt thereof, i.e., the active ingredient, will depend upon numerous factors such as the severity of the disease to be treated, the age and relative health of the patient, the potency of the compound being utilized, the route and form of administration, and other factors.

In general, compounds of Formula (I) or (I'), or a pharmaceutically acceptable salt thereof will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, a compound of Formula (I) or (I'), or a pharmaceutically acceptable salt thereof in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds of Formula (I) or (I'), or a pharmaceutically acceptable salt thereof may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds of Formula (I) or (I'), or a pharmaceutically acceptable salt thereof may be administered topically, that is by non-systemic administration. This includes the application of a compound of Formula (I) or (I'), or a pharmaceutically acceptable salt thereof externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.0010% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds of Formula (I) or (I'), or a pharmaceutically acceptable salt thereof may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

Combinations and Combination Therapies

The compounds of Formula (I) or (I'), or a pharmaceutically acceptable salt thereof may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of Formula (I) or (I'), or a pharmaceutically acceptable salt thereof. When a compound of this disclosure is used contemporaneously with one or more other drugs, a pharmaceutical composition in unit dosage form containing such other drugs and the compound of Formula (I) or (I'), or a pharmaceutically acceptable salt thereof is preferred. However, the combination therapy may also include therapies in which the compound of this disclosure and one or more other drugs are administered on different overlapping schedules. It is also contemplated that when used in combination with one or more other active ingredients, the compounds of Formula (I) or (I'), or a pharmaceutically acceptable salt thereof and the other active ingredients may be used in lower doses than when each is used singly.

Accordingly, the pharmaceutical compositions of Formula (I) or (I'), or a pharmaceutically acceptable salt thereof also include those that contain one or more other drugs, in addition to a compound of Formula (I) or (I'), or a pharmaceutically acceptable salt thereof.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of Formula (I) or (I'), or a pharmaceutically acceptable salt thereof. When a compound of this disclosure is used contemporaneously with one or more other drugs, a pharmaceutical composition containing such other drugs in addition to the compound of this disclosure can be used. Accordingly, the pharmaceutical compositions of Formula (I) or (I'), or a pharmaceutically acceptable salt thereof also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Suitable anti-cancer agents also include inhibitors of kinases associated cell proliferative disorder. These kinases include but not limited to Aurora-A, BTK, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, MEK, PAK1, PAK2, PAK3, PAK4, PDK1, PKA, PKC, RAF, Rsk and SGK. For example, inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, axitinib; EGFR inhibitor such as afatinib, brivanib, carbozatinib, erlotinib, gefitinib, neratinib, lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, TG100-115; MTOR inhibitor such as rapamycin (sirolimus), temsirolimus, everolimus, XL388, XL765, AZD2013, PF04691502, PKI-587, BEZ235, GDC0349; MEK inhibitor such as AZD6244, trametinib, PD184352, pimasertinib, GDC-0973, AZD8330; CSF1R inhibitors (PLX3397, LY3022855, etc.) and CSF1R antibodies (IMC-054, RG7155, etc.); TGF beta receptor kinase inhibitor such as LY2157299; BTK inhibitor such as ibrutinib.

Other anti-cancer agents include proteasome inhibitor such as carfilzomib, MLN9708, delanzomib, or bortezomib; BET inhibitors such as INCB054329, OTX015, CPI-0610; LSD1 inhibitors such as GSK2979552, INCB059872; HDAC inhibitors such as panobinostat, vorinostat; DNA methyl transferase inhibitors such as azacytidine, decitabine), and other epigenetic modulator; SHP-2 inhibitor such as TNO155; Bcl2 inhibitor ABT-199, and other Bcl-2 family protein inhibitors; HIF-2α inhibitors such as PT2977 and PT2385; Beta catenin pathway inhibitors, notch pathway inhibitors and hedgehog pathway inhibitors; Antibodies or other therapeutic proteins against VEGF include bevacizumab and aflibercept.

Other anti-cancer agents/drugs that can be used in combination with the compounds of the invention include, but are not limited to, liver X receptor (LXR) modulators, including LXR agonists and LXR beta-selective agonists; aryl hydrocarbon receptor (AhR) inhibitors.

Other anti-cancer agents that can be employed in combination with a compound of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of the disclosure include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; tenipo-side; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula (I) or (I'), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., cytarabine), purine analogs (e.g., mercaptopurine, thioguanine, pentostatin).

Examples of natural products useful in combination with a compound of this disclosure include but are not limited to *vinca* alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of this disclosure) include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, cytarabine), purine analogs (e.g., mercaptopurine, thioguanine, pentostatin).

Examples of hormones and antagonists useful in combination a compound of this disclosure include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Other anti-cancer agents that can be employed in combination with a compound of the disclosure include: anticancer agents which act by arresting cells in the G2-M phases due to stabilized microtubules and include Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

One or more additional immune checkpoint inhibitors can be used in combination with a compound as described herein for treatment of HIF-2α-associated diseases, disorders or conditions. Exemplary immune checkpoint inhibitors include inhibitors (smack molecules or biologics) against immune checkpoint molecules such as CD27, CD28, CD40, CD122, CD96, CD73, CD39, CD47, OX40, GITR, CSF1R, JAK, PI3K delta, PI3K gamma, TAM, arginase, CD137 (also known as 4-1BB), ICOS, A2AR, A2BR, SHP-2, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383 Compounds of the invention can also be used to increase or enhance an immune response, including increasing the immune response to an antigen; to improve immunization, including increasing vaccine efficacy; and to increase inflammation. In some embodiments, the compounds of the invention can be sued to enhance the immune response to vaccines including, but not limited, *Listeria* vaccines, oncolytic viarl vaccines, and cancer vaccines such as GVAX® (granulocyte-macrophage colony-stimulating factor (GM-CF) gene-transfected tumor cell vaccine). Anti-cancer vaccines include dendritic cells, synthetic peptides, DNA vaccines and recombinant viruses. Other immune-modulatory agents also include those that block immune cell migration such as antagonists to chemokine receptors, including CCR2 and CCR4; Sting agonists and Toll receptor agonists.

Other anti-cancer agents also include those that augment the immune system such as adjuvants or adoptive T cell transfer. Compounds of this application may be effective in combination with CAR (Chimeric antigen receptor) T cell treatment as a booster for T cell activation

EXAMPLES

The following preparations of compounds of Formula (I) are given to enable those skilled in the art to more clearly understand and to practice the present disclosure. They should not be considered as limiting the scope of the disclosure, but merely as being illustrative and representative thereof. In the following examples, tR means retention time.

Example 1

Synthesis of 3-((4-(difluoromethyl)-1,1,2,2-tetrafluoro-3-hydroxy-2,3-dihydro-1H-inden-5-yl)oxy)-5-fluorobenzonitrile

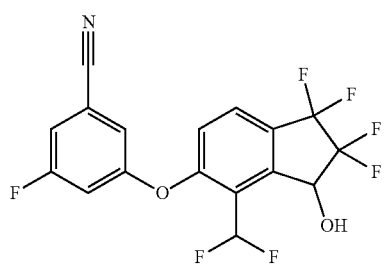 [SMILES: N#Cc1cc(F)cc(Oc2ccc3c(c2C(F)F)C(O)C(F)(F)C3(F)F)c1]

Step 1: ethyl 3-(2-bromo-4-fluorophenyl)-2,2-difluoro-3-hydroxypropanoate

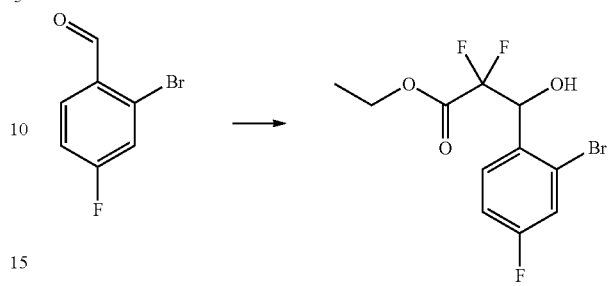

To a stirred mixture of zinc (6.97 g, 106.56 mmol, 1.0 equiv), 1,2-dibromoethane (388.71 mg, 2.069 mmol, 0.02 equiv) and chlorotrimethylsilane (1.12 g, 10.346 mmol, 0.10 equiv) in THF (200 mL) was added a solution of ethyl 2-bromo-2,2-difluoroacetate (21 g, 103.45 mmol, 1.0 equiv) and 2-bromo-4-fluorobenzaldehyde (21.0 g, 103.45 mmol, 1.0 equiv) in THF (100 mL) dropwise at room temperature under nitrogen atmosphere. The resulting mixture was stirred for 16 h at 75° C. under nitrogen atmosphere. The reaction mixture was cooled and quenched by the addition of ice water. The organic solvent was removed under vacuum and the resulting mixture was extracted with EtOAc. The combined organic layer was washed with water, dried over anhydrous $Na_2SO_4$ and concentrated under reduced pressure. The residue was purified by silica gel column chromatography, eluted with PE/EtOAc (5:1) to afford the title compound (18 g, 53.2%) as yellow oil.

Step 2: ethyl 3-(2-bromo-4-fluorophenyl)-2,2-difluoro-3-oxopropanoate

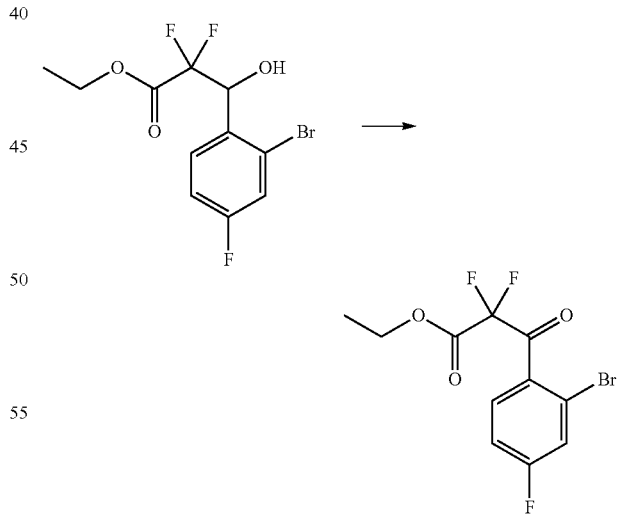

To a stirred solution of ethyl 3-(2-bromo-4-fluorophenyl)-2,2-difluoro-3-hydroxypropanoate (16 g, 48.9 mmol, 1.0 equiv) in $CH_3CN$ (200 mL) was added 2-iodoxybenzoic acid (27.4 g, 97.83 mmol, 2.0 equiv) at room temperature and the resulting mixture was stirred for 3 h at 80° C. The reaction solution was then cooled to room temperature, filtered and the filter cake was washed with EtOAc. The filtrate was concentrated under reduced pressure. The residue was purified by silica gel column chromatography, eluted with PE/EtOAc (10:1) to afford the title compound (10.3 g, 64.8%) as yellow oil.

Step 3: ethyl 3-(2-bromo-4-fluorophenyl)-2,2,3,3-tetrafluoropropanoate

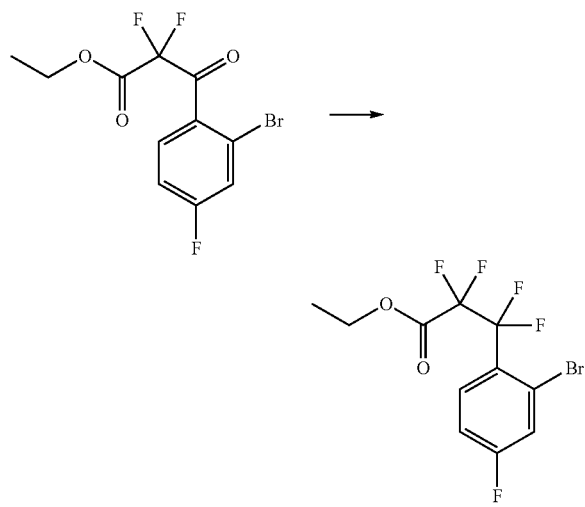

To a stirred solution of ethyl 3-(2-bromo-4-fluorophenyl)-2,2-difluoro-3-oxopropanoate (6.1 g, 18.8 mmol, 1.0 equiv) in CHCl₃ (6 mL) was added DAST (30.25 g, 187.6 mmol, 10.0 equiv) dropwise at room temperature and the resulting mixture was stirred for 16 h at 70° C. under nitrogen atmosphere. The reaction solution was allowed to cool to room temperature and quenched by the addition of ice water. The mixture was extracted with DCM. The organic layer was dried over anhydrous Na₂SO₄ and concentrated. The residue was purified by silica gel column chromatography, eluted with PE/EtOAc (10:1) to afford the title compound (2.4 g, 36.8%) as yellow oil.

Step 4: 2,2,3,3,6-pentafluoro-2,3-dihydro-1H-inden-1-one

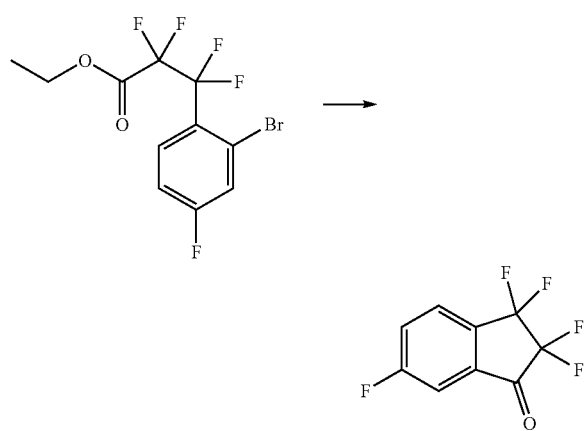

To a stirred solution of ethyl 3-(2-bromo-4-fluorophenyl)-2,2,3,3-tetrafluoropropanoate (4.20 g, 12.101 mmol, 1.0 equiv) in THF (50 mL) was added 2.5M n-BuLi (7.26 mL, 18.15 mmol, 1.5 equiv) dropwise at −78° C. under nitrogen atmosphere and the resulting mixture was stirred for 2 h between −70° C. and −80° C. The reaction mixture was quenched by the addition of saturated NH₄Cl (aq.) and extracted with EtOAc. The organic layer was dried over anhydrous Na₂SO₄ and concentrated under reduced pressure. The residue was purified by silica gel column chromatography, eluted with PE/EtOAc (20:1) to afford the title compound (2.25 g, 83.7%) as light yellow oil.

Step 5: 2,2,3,3,6-pentafluoro-2,3-dihydro-TH-inden-1-ol

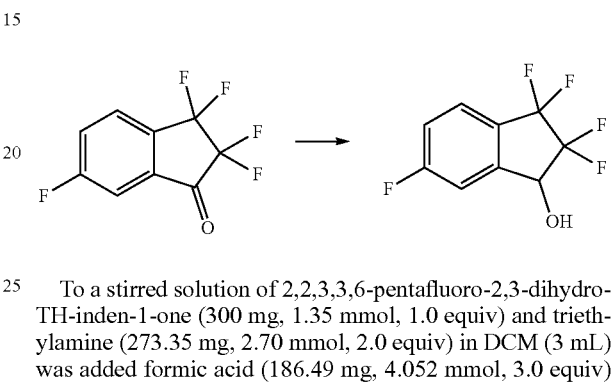

To a stirred solution of 2,2,3,3,6-pentafluoro-2,3-dihydro-TH-inden-1-one (300 mg, 1.35 mmol, 1.0 equiv) and triethylamine (273.35 mg, 2.70 mmol, 2.0 equiv) in DCM (3 mL) was added formic acid (186.49 mg, 4.052 mmol, 3.0 equiv) dropwise at 0° C., followed by the addition of RuCl(P-cymene)[(S,S)-Ts-DPEN] (8.59 mg, 0.014 mmol, 0.01 equiv). The resulting mixture was stirred for 3 h at room temperature under nitrogen atmosphere and then washed with water. The organic layer was dried over anhydrous Na₂SO₄ and concentrated under reduced pressure. The residue was purified by silica gel column chromatography, eluted with PE/EtOAc (5:1) to afford the title compound (300 mg, 99.1%) as colorless oil.

Step 6: 1,1,2,2,5-pentafluoro-3-hydroxy-2,3-dihydro-TH-indene-4-carbaldehyde

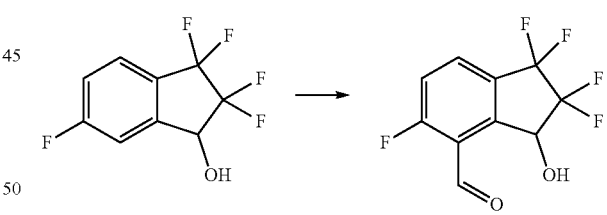

To a stirred solution of 2,2,3,3,6-pentafluoro-2,3-dihydro-TH-inden-1-ol (260.0 mg, 1.16 mmol, 1.0 equiv) in THF (3 mL) was added LDA (3.480 mmol, 3.0 equiv) dropwise at −78° C. under nitrogen atmosphere. The resulting mixture was allowed to warm to −30° C. and stirred for 2 h at this temperature under nitrogen atmosphere. To the above mixture was added ethyl formate (171.8 mg, 2.3 mmol, 2.0 equiv) dropwise at −78° C. and the resulting mixture was stirred for additional 1 h at −30° C. The reaction mixture was then quenched by the addition of water at −30° C., extracted with EtOAc. The combined organic layer was dried over anhydrous Na₂SO₄ and concentrated. The residue was purified by silica gel column chromatography, eluted with PE/EtOAc (5:1) to afford the title compound (90 mg, 30.8%) as a light yellow solid.

Step 7: 1,1,2,2,5-pentafluoro-3-oxo-2,3-dihydro-1H-indene-4-carbaldehyde

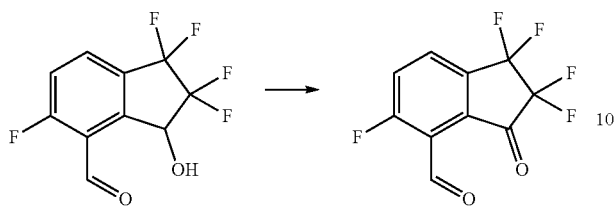

To a stirred solution of 1,1,2,2,5-pentafluoro-3-hydroxy-2,3-dihydro-1H-indene-4-carbaldehyde (92.0 mg, 0.36 mmol, 1.0 equiv) in $CH_3CN$ (2.0 mL) was added 2-iodoxybenzoic acid (204.3 mg, 0.73 mmol, 2.0 equiv) at room temperature. After stirring for 3 h at 80° C., the reaction mixture was cooled to room temperature and filtered. The filter cake was washed with ethyl acetate. The filtrate was concentrated under reduced pressure to afford the title compound (85 mg, 93.1%) as light yellow oil.

Step 8: 7-(difluoromethyl)-2,2,3,3,6-pentafluoro-2,3-dihydro-1H-inden-1-one

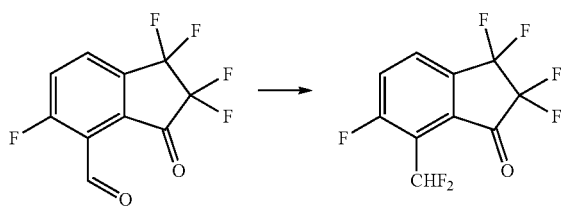 [SMILES: O=Cc1c(F)ccc2c1C(=O)C(F)(F)C2(F)F ; O=C1c2c(ccc(F)c2C(F)F)C(F)(F)C1(F)F]

To a stirred solution of 1,1,2,2,5-pentafluoro-3-oxo-2,3-dihydro-1H-indene-4-carbaldehyde (85.00 mg, 0.340 mmol, 1.00 equiv) in DCM (1.5 mL) was added DAST (82.11 mg, 0.510 mmol, 1.5 equiv) at room temperature under nitrogen atmosphere. After stirring for 3 h at room temperature, the reaction was quenched with ice water at 0° C. The phases were separated and the organic layer was washed with water, brine, and then dried over anhydrous $Na_2SO_4$. After filtration, the filtrate was concentrated under reduced pressure to afford the title compound (80 mg, 86.5%) as light yellow oil.

Step 9: 3-[[4-(difluoromethyl)-1,1,2,2-tetrafluoro-3-oxo-2,3-dihydro-1H-inden-5-yl]oxy]-5-fluorobenzonitrile

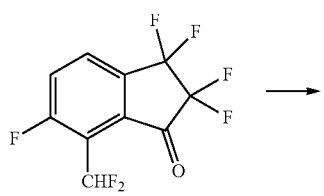

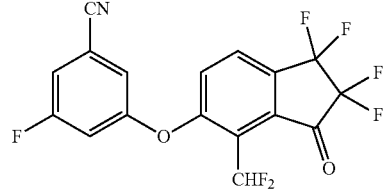

To a stirred mixture of 7-(difluoromethyl)-2,2,3,3,6-pentafluoro-2,3-dihydro-1H-inden-1-one (70.00 mg, 0.257 mmol, 1.00 equiv) and 3-fluoro-5-hydroxybenzonitrile (52.91 mg, 0.386 mmol, 1.50 equiv) in DMF (1.00 mL) was added $Cs_2CO_3$ (125.72 mg, 0.386 mmol, 1.50 equiv) at room temperature. After stirring for 4 h at 50° C., the reaction mixture was cooled to room temperature and water was added. The resulting mixture was extracted with EtOAc. The organic layer was washed with brine, dried over anhydrous $Na_2SO_4$ and concentrated under reduced pressure to afford the title compound (60 mg, crude) as brown oil, which was used in the next step without further purification

Step 10: 3-[[4-(difluoromethyl)-1,1,2,2-tetrafluoro-3-hydroxy-2,3-dihydro-1H-inden-5-yl]oxy]-5-fluorobenzonitrile

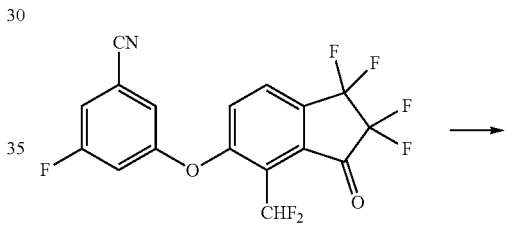

To a mixture of 3-[[4-(difluoromethyl)-1,1,2,2-tetrafluoro-3-oxo-2,3-dihydro-1H-inden-5-yl]oxy]-5-fluorobenzonitrile (10.0 mg, 0.026 mmol, 1.0 equiv) and RuCl(P-cymene)[(S,S)-Ts-DPEN] (0.84 mg, 0.0013 mmol, 0.05 equiv) in DCM (0.3 mL) were added TEA (5.20 mg, 0.051 mmol, 2.0 equiv) and a solution of HCOOH (3.55 mg, 0.077 mmol, 3.0 equiv) in DCM (0.5 mL) dropwise at 0° C. under nitrogen atmosphere. After stirring for 5 hours at 0° C., the resulting mixture was concentrated under vacuum. The residue was purified by Prep-HPLC to afford the title compound (3 mg, 29.8%) as a white solid. MS (ES, m/z): $[M-1]^-=389.9$.

Example 1A

Synthesis of (R)-3-((4-(difluoromethyl)-1,1,2,2-tetrafluoro-3-hydroxy-2,3-dihydro-1H-inden-5-yl)oxy)-5-fluoro benzonitrile [1a] and (S)-3-((4-(difluoromethyl)-1,1,2,2-tetrafluoro-3-hydroxy-2,3-dihydro-1H-inden-5-yl)oxy)-5-fluorobenzonitrile [1b]

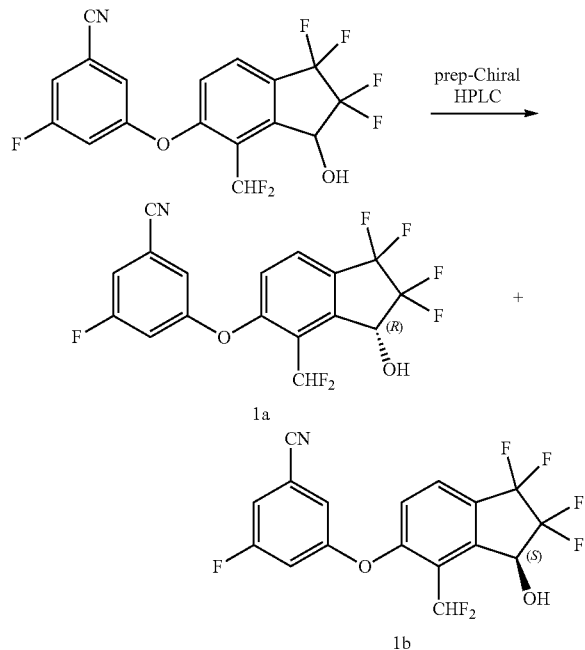

3-((4-(Difluoromethyl)-1,1,2,2-tetrafluoro-3-hydroxy-2,3-dihydro-1H-inden-5-yl)oxy)-5-fluorobenzonitrile (100 mg) was separated by chiral HPLC described below, to afford compound [1a] and [1b]. MS (ES, m/z): [M−1]⁻=390.0.

Chiral HPLC conditions: Instrument, SHIMADZU LC-20AD; Column: CHIRAPAK IA-3, 4.6*50 mm, 3 uM; Mobile phase A, n-hexane; Mobile phase B, Ethanol; Conc. Of phase B, 8%; Flow rate, 1.0 mL/min.

One of compounds [1a] and [1b] has tR: 2.03 min and and the other has tR: 2.57.

Example 1B

Synthesis of (R)-3-((4-(difluoromethyl)-1,1,2,2-tetrafluoro-3-hydroxy-2,3-dihydro-1H-inden-5-yl-3-d)oxy)-5-fluorobenzonitrile [1c] and (S)-3-((4-(difluoromethyl)-1,1,2,2-tetrafluoro-3-hydroxy-2,3-dihydro-1H-inden-5-yl-3-d)oxy)-5-fluorobenzonitrile [1d]

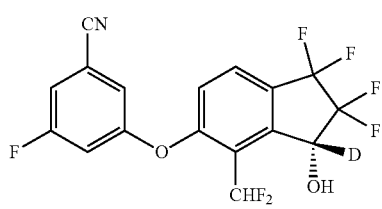

1c

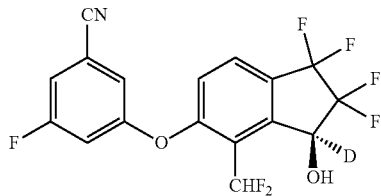

1d

To a stirred mixture of 3-((4-(difluoromethyl)-1,1,2,2-tetrafluoro-3-oxo-2,3-dihydro-1H-inden-5-yl)oxy)-5-fluorobenzonitrile (100 mg, 0.257 mmol, 1.00 equiv) and Et₃N (52 mg, 0.514 mmol, 2.00 equiv) in DCM (1 mL) were added DCOOD (37 mg, 0.771 mmol, 3.00 equiv) and RuCl(P-cymene)[(S,S)-Ts-DPEN] (1.6 mg, 0.003 mmol, 0.01 equiv) at room temperature under nitrogen atmosphere. After stirring for 16 hours at room temperature, the resulting mixture was concentrated under vacuum. The residue was purified by silica gel column chromatography, eluted with PE/EA (3/1), and then purified by chiral HPLC, described below, to afford compound [1c] and [1d]. MS (ES, m/z): [M−1]⁻=391.1

Chiral HPLC conditions: Instrument, SHIMADZU LC-20AD; Column: CHIRAPAK IA-3, 4.6*50 mm, 3 uM; Mobile phase A, n-hexane (0.1% TFA); Mobile phase B, Ethanol; Conc. Of phase B, 8%; Flow rate, 1.0 mL/min. One of compounds [1c] and [1d] has tR: 2.18 min and and the other has tR: 2.67.

Example 2

Synthesis of 3-[[4-(difluoromethyl)-1,1,2,2-tetrafluoro-3-hydroxy-3-methyl-2,3-dihydro-1H-inden-5-yl]oxy]-5-fluorobenzonitrile

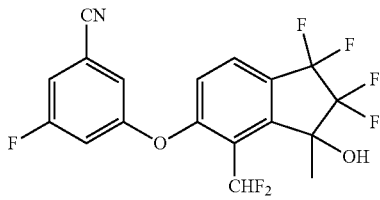 [SMILES: CC1(O)c2c(ccc(Oc3cc(F)cc(C#N)c3)c2C(F)F)C(F)(F)C1(F)F]

To a stirred solution of 3-[[4-(difluoromethyl)-1,1,2,2-tetrafluoro-3-oxo-2,3-dihydro-1H-inden-5-yl]oxy]-5-fluorobenzonitrile (20.0 mg, 0.051 mmol, 1.0 equiv) in THF (0.5 mL) was added 2.0M MeMgBr in THF (0.05 mL, 0.10 mmol, 2.0 equiv) at 0° C. under nitrogen atmosphere. After stirring for 3 h at room temperature, the reaction mixture was quenched with sat. NH₄Cl (aq.) at 0° C. and then extracted with EtOAc. The organic layer was washed with brine, dried over anhydrous Na₂SO₄ and concentrated. The residue was purified by Prep-HPLC to afford the title compound (2.2 mg, 10.5%). MS (ES, m/z): [M−1]⁻=404.1.

Example 3

Synthesis of 3-[[3-amino-4-(difluoromethyl)-1,1,2,2-tetrafluoro-2,3-dihydro-1H-inden-5-yl]oxy]-5-fluorobenzonitrile

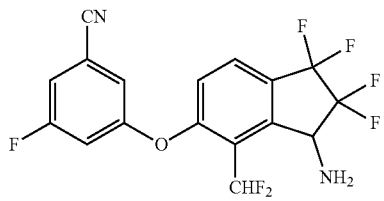 [SMILES: N#Cc1cc(F)cc(Oc2ccc3c(c2C(F)F)C(N)C(F)(F)C3(F)F)c1]

To a stirred solution of 3-((4-(difluoromethyl)-1,1,2,2-tetrafluoro-3-oxo-2,3-dihydro-1H-inden-5-yl)oxy)-5-fluorobenzonitrile (300 mg, 0.771 mmol, 1.00 equiv) in THF (5 mL) were added Ti(OEt)$_4$ (352 mg, 1.542 mmol, 2.00 equiv) and 7 mol/L NH$_3$ in MeOH (0.55 mL, 3.85 mmol, 5.00 equiv) at room temperature. The mixture was stirred for 24 h at 50° C. To the above mixture was added NaBH$_4$ (44 mg, 1.156 mmol, 1.50 equiv) at room temperature. The reaction mixture was stirred for additional 10 min. The reaction was quenched with saturated NH$_4$Cl (aq.) at room temperature. The resulting mixture was extracted with EA. The organic layer was washed with water and brine. The organic layer was concentrated in vacuum. The residue was purified by Prep-HPLC to afford 3-[[3-amino-4-(difluoromethyl)-1,1,2,2-tetrafluoro-2,3-dihydro-1H-inden-5-yl]oxy]-5-fluorobenzonitrile (60 mg) as a white solid. The (R)-3-((3-amino-4-(difluoromethyl)-1,1,2,2-tetrafluoro-2,3-dihydro-1H-inden-5-yl)oxy)-5-fluorobenzonitrile [3a] and (S)-3-((3-amino-4-(difluoromethyl)-1,1,2,2-tetrafluoro-2,3-dihydro-TH-inden-5-yl)oxy)-5-fluorobenzonitrile [3b] enantiomers, MS (ES, m/z): [M-H]$^-$=389.1, were separated using chiral HPLC described below.

Conditions: Instrument, SHIMADZU LC-20AD; Column: CHIRAPAK IA-3, 4.6*50 mm, 3 μM; Mobile phase A, n-hexane (0.1% TFA); Mobile phase B, Ethanol; Conc. Of phase B, 20%; Flow rate, 1.0 mL/min. One of the compounds [3a] and [3b] has tR: 1.45 min and the other has tR: 2.24 min.

Example 4

Synthesis of 7-(difluoromethyl)-6-(3,5-difluorophenoxy)-2,2,3,3-tetrafluoro-2,3-dihydro-1H-inden-1-ol

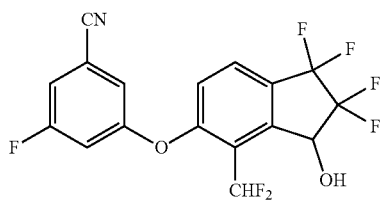

Step 1: 7-(difluoromethyl)-6-(3,5-difluorophenoxy)-2,2,3,3-tetrafluoro-2,3-dihydro-1H-inden-1-one

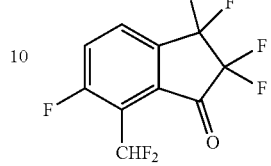
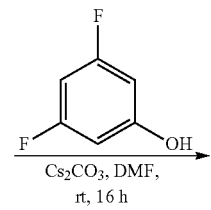

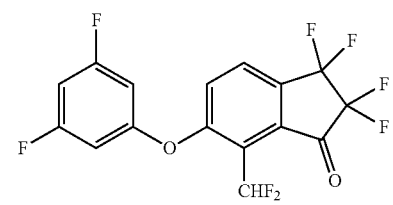

To a stirred mixture of 7-(difluoromethyl)-2,2,3,3,6-pentafluoro-2,3-dihydro-1H-inden-1-one (20 mg, 0.073 mmol, 1.00 equiv) and 3,5-difluorophenol (10 mg, 0.073 mmol, 1.00 equiv) in DMF (1 mL) was added Cs$_2$CO$_3$ (24 mg, 0.073 mmol, 1.00 equiv) at room temperature. The resulting mixture was stirred for 16 h at room temperature and then diluted with water and extracted with EtOAc. The organic layer was washed with water and brine, dried over anhydrous Na$_2$SO$_4$. After filtration, the filtrate was concentrated under reduced pressure. The residue was purified by silica gel column chromatography (PE/EtOAc=10/1), followed by Prep-HPLC to afford the title compound (8 mg, 28.5%).

Step 2: 7-(difluoromethyl)-6-(3,5-difluorophenoxy)-2,2,3,3-tetrafluoro-2,3-dihydro-1H-inden-1-ol

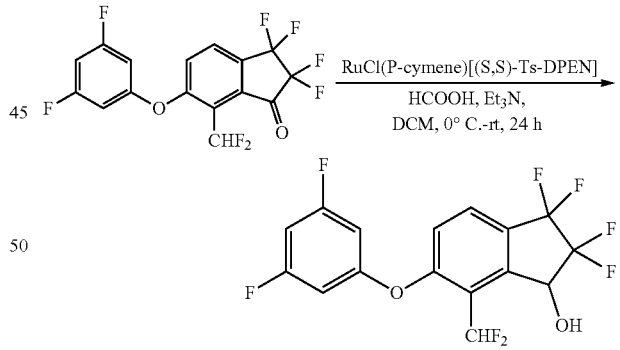

To a stirred solution of 7-(difluoromethyl)-6-(3,5-difluorophenoxy)-2,2,3,3-tetrafluoro-2,3-dihydro-1H-inden-1-one (38 mg, 0.099 mmol, 1.00 equiv), Et$_3$N (20 mg, 0.199 mmol, 2.00 equiv) and HCOOH (14 mg, 0.298 mmol, 3.00 equiv) in DCM (2 mL) was added RuCl(P-cymene)[(S,S)-Ts-DPEN] (6.3 mg, 0.010 mmol, 0.10 equiv) at 0° C. The resulting mixture was stirred for 24 h at room temperature under nitrogen atmosphere. The reaction mixture was diluted with water, extracted with EtOAc. The organic layer was washed with water and brine, concentrated in vacuum and the residue was purified by Prep-HPLC to afford the title compound (19 mg, 49.7%). MS (ES, m/z): [M-H]$^-$=383.1.

Example 5

Synthesis of 3-((4-(difluoromethyl)-1,1,2,2-tetrafluoro-3-hydroxy-2,3-dihydro-1H-inden-5-yl)oxy)-5-methylbenzonitrile

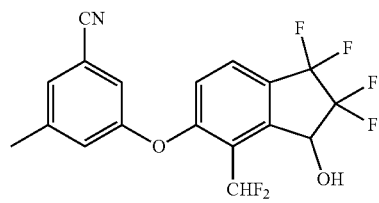 [SMILES: Cc1cc(C#N)cc(Oc2ccc3c(c2C(F)F)C(O)C(F)(F)C3(F)F)c1]

The title compound was synthesized by proceeding analogously as described in Example 4, using 3-hydroxy-5-methylbenzonitrile in Step 2. MS (ES, m/z): [M−1]⁻=386.2.

Example 6

Synthesis of 3-chloro-5-((4-(difluoromethyl)-1,1,2,2-tetrafluoro-3-hydroxy-2,3-dihydro-1H-inden-5-yl)oxy)benzonitrile

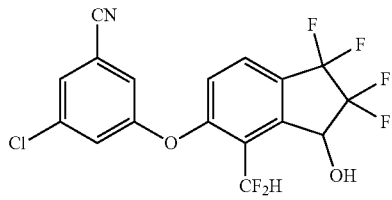

The title compound was synthesized by proceeding analogously as described in Example 4, using 3-chloro-5-hydroxybenzonitrile in Step 2. MS (ES, m/z): [M−1]⁻=406.1.

Example 7

Synthesis of 6-(3-chloro-5-fluorophenoxy)-7-(difluoromethyl)-2,2,3,3-tetrafluoro-2,3-dihydro-1H-inden-1-ol

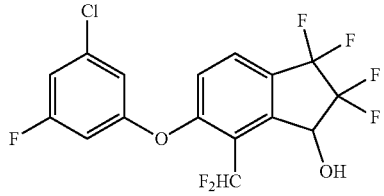 [SMILES: OC1c2c(ccc(Oc3cc(F)cc(Cl)c3)c2C(F)F)C(F)(F)C1(F)F]

The title compound was synthesized by proceeding analogously as described in Example 4, using 3-chloro-5-fluorophenol in Step 2. MS (ES, m/z): [M+1]⁻=399.1.

Example 8

Synthesis of 6-(3,3-difluorocyclobutoxy)-7-(difluoromethyl)-2,2,3,3-tetrafluoro-2,3-dihydro-1H-inden-1-ol

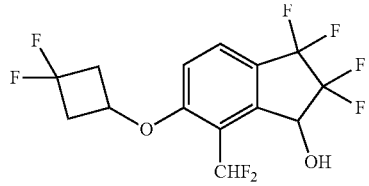 [SMILES: OC1c2c(ccc(OC3CC(F)(F)C3)c2C(F)F)C(F)(F)C1(F)F]

The title compound was synthesized by proceeding analogously as described in Example 4, using 3,3-difluorocyclobutan-1-ol in Step 2. MS (ES, m/z): [M−1]⁻=361.1.

Example 9

Synthesis of 5-((4-(difluoromethyl)-1,1,2,2-tetrafluoro-3-hydroxy-2,3-dihydro-1H-inden-5-yl)oxy)nicotinonitrile

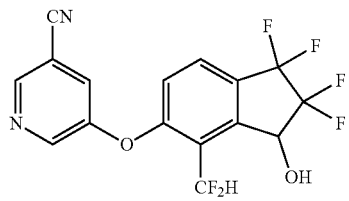 [SMILES: N#Cc1cncc(Oc2ccc3c(c2C(F)F)C(O)C(F)(F)C3(F)F)c1]

The title compound was synthesized by proceeding analogously as described in Example 4, using 5-hydroxynicotinonitrile in Step 2. MS (ES, m/z): [M+1]⁻=373.1.

Example 10

Synthesis of 7-(difluoromethyl)-2,2,3,3-tetrafluoro-6-((5-fluoropyridin-3-yl)oxy)-2,3-dihydro-1H-inden-1-ol

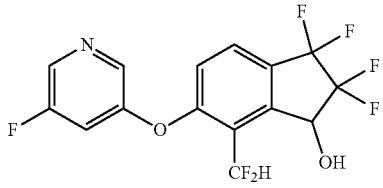 [SMILES: OC1c2c(ccc(Oc3cncc(F)c3)c2C(F)F)C(F)(F)C1(F)F]

The title compound was synthesized by proceeding analogously as described in Example 4, using 5-fluoropyridin-3-ol in Step 2. MS (ES, m/z): [M−1]⁻=366.1.

Example 11

Synthesis of (R)-7-(difluoromethyl)-2,2,3,3-tetrafluoro-6-((5-fluoropyridin-3-yl)oxy)-2,3-dihydro-1H-inden-1-d-1-ol [11a] and (S)-7-(difluoromethyl)-2,2,3,3-tetrafluoro-6-((5-fluoropyridin-3-yl)oxy)-2,3-dihydro-1H-inden-1-d-1-ol [11b]

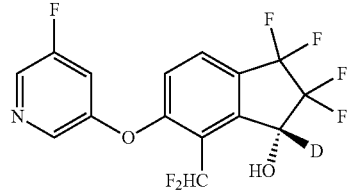

11a

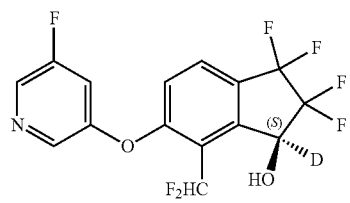

11b

Step 1: 7-(difluoromethyl)-2,2,3,3-tetrafluoro-6-((5-fluoropyridin-3-yl)oxy)-2,3-dihydro-1H-inden-1-one

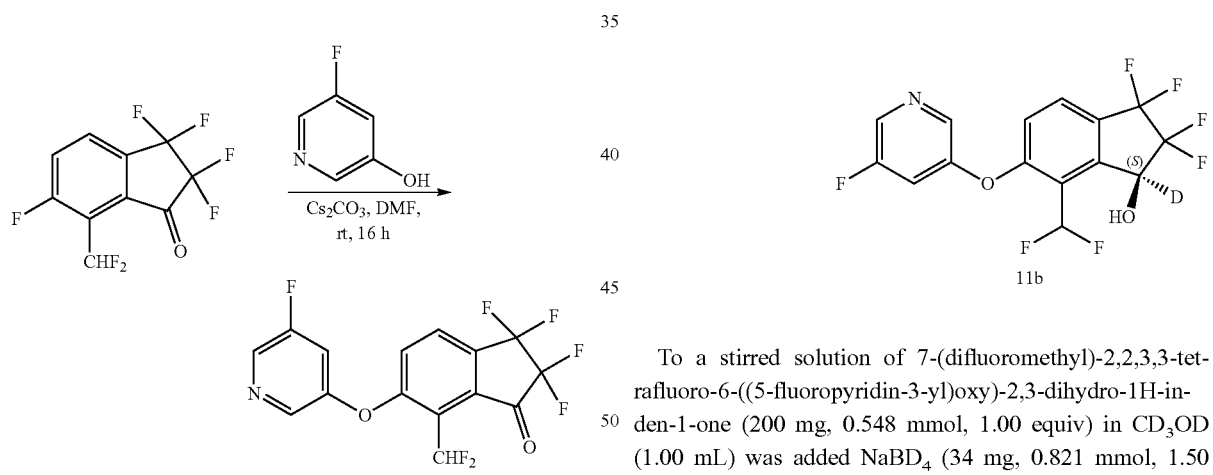

To a stirred mixture of 7-(difluoromethyl)-2,2,3,3,6-pentafluoro-2,3-dihydro-1H-inden-1-one (230 mg, 0.845 mmol, 1.00 equiv) and 5-fluoropyridin-3-ol (127 mg, 1.124 mmol, 1.33 equiv) in DMF (3.00 mL) was added $Cs_2CO_3$ (330 mg, 1.014 mmol, 1.20 equiv) at room temperature under nitrogen atmosphere. After stirring for 16 h at room temperature, the reaction was quenched with water at room temperature. The resulting mixture was extracted with EtOAc and the combined organic layers were washed with brine, dried over anhydrous $Na_2SO_4$. After filtration, the filtrate was concentrated under reduced pressure. The residue was purified by Prep-TLC (PE/EtOAc 3:1) to afford the title compound (220 mg, 71.3%).

Step 2: (R)-7-(difluoromethyl)-2,2,3,3-tetrafluoro-6-((5-fluoropyridin-3-yl)oxy)-2,3-dihydro-1H-inden-1-d-1-ol [11] and (S)-7-(difluoromethyl)-2,2,3,3-tetrafluoro-6-((5-fluoropyridin-3-yl)oxy)-2,3-dihydro-1H-inden-1-d-1-ol [12]

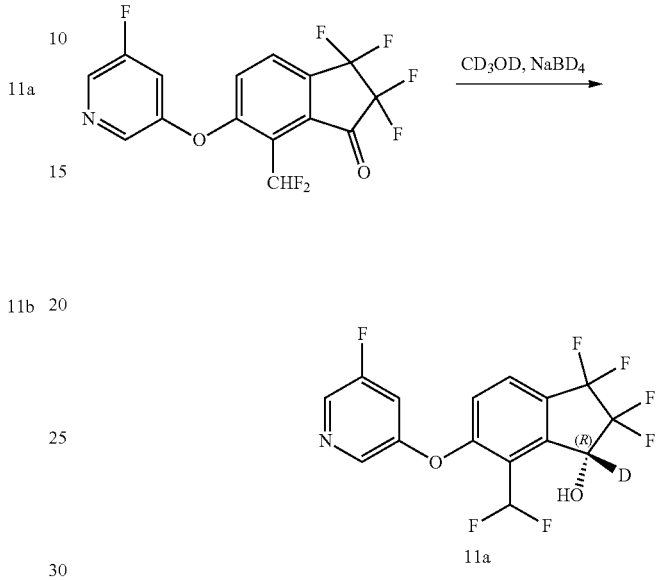

To a stirred solution of 7-(difluoromethyl)-2,2,3,3-tetrafluoro-6-((5-fluoropyridin-3-yl)oxy)-2,3-dihydro-1H-inden-1-one (200 mg, 0.548 mmol, 1.00 equiv) in $CD_3OD$ (1.00 mL) was added $NaBD_4$ (34 mg, 0.821 mmol, 1.50 equiv) at room temperature. After stirring for 1 h at room temperature, the reaction was quenched with saturated $NH_4Cl$ (aq.) at room temperature. The resulting solution was purified by Prep-HPLC to afford the racemic product. The racemic product was separated by Chiral-HPLC, described below, to afford compounds [11a] and compound [11b]. MS (ES, m/z): $[M+1]^+=369.1$ Chiral HPLC conditions: Instrument, SHIMADZU LC-20AD; Column: lux cellulose-4, 4.6*50 mm, 3 uM; Mobile phase A, n-hexane; Mobile phase B, Ethanol; Conc. Of phase B, 15%; Flow rate, 1.0 mL/min. One of compounds [11a] and [11b] has tR: 1.98 min and the other has tR: 2.31 min.

Example 12

Synthesis of (R)-5-(3-cyano-5-fluorophenoxy)-1,1,2,2-tetrafluoro-3-hydroxy-2,3-dihydro-1H-indene-4-carbonitrile [12a] and (S)-5-(3-cyano-5-fluorophenoxy)-1,1,2,2-tetrafluoro-3-hydroxy-2,3-dihydro-1H-indene-4-carbonitrile [12b]

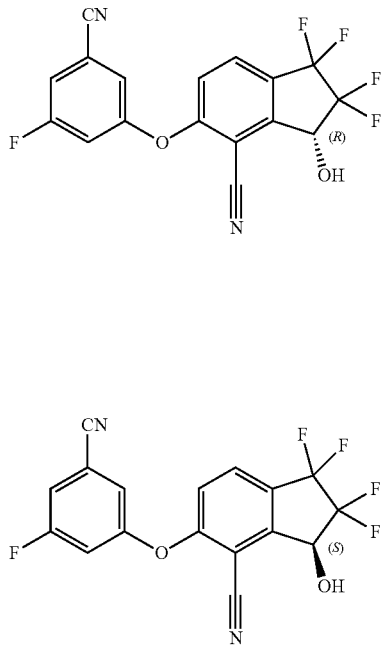

To a stirred mixture of 5-(3-cyano-5-fluorophenoxy)-1,1,2,2-tetrafluoro-3-oxo-2,3-dihydro-1H-indene-4-carbonitrile (40 mg, 0.110 mmol, 1.00 equiv) and Et₃N (22 mg, 0.220 mmol, 2.00 equiv) in DCM (1 mL) were added HCOOH (15 mg, 0.329 mmol, 3.00 equiv) and RuCl(P-cymene)[(S,S)-Ts-DPEN] (3.5 mg, 0.005 mmol, 0.05 equiv) at room temperature. The resulting mixture was stirred for 16 h at room temperature under nitrogen atmosphere and then diluted with DCM, washed with water. The organic layer was dried over anhydrous Na₂SO₄ and concentrated under reduced pressure. The residue was purified by Prep-HPLC followed by Prep-Chiral-HPLC, described below, to afford compounds [12a] and [12b] as a white solid. MS (ES, m/z): $[M-1]^-=365.1$.

Chiral HPLC conditions: Instrument, SHIMADZU LC-20AD; Column: lux cellulose-4, 4.6*50 mm, 3 uM; Mobile phase A, n-hexane (0.1% TFA); Mobile phase B, Ethanol; Conc. Of phase B, 15%; Flow rate, 1.0 mL/min. One of compounds [12a] and [12b] has tR: 4.68 min and the other has tR: 5.41 min.

Example 13

Synthesis of (S)-5-(3-cyano-5-fluorophenoxy)-1,1,2,2-tetrafluoro-3-hydroxy-2,3-dihydro-1H-indene-4-carbonitrile-3-d [13a] and (R)-5-(3-cyano-5-fluorophenoxy)-1,1,2,2-tetrafluoro-3-hydroxy-2,3-dihydro-1H-indene-4-carbonitrile-3-d [13b]

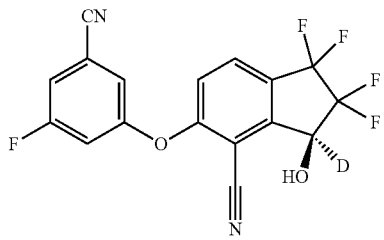

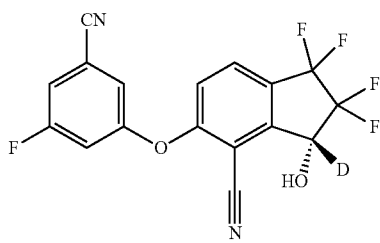

To a stirred mixture of 5-(3-cyano-5-fluorophenoxy)-1,1,2,2-tetrafluoro-3-oxo-2,3-dihydro-1H-indene-4-carbonitrile (100 mg, 0.275 mmol, 1.00 equiv) in CD₃OD (1 mL) was added NaBD₄ (23 mg, 0.549 mmol, 2.00 equiv) at room temperature. The resulting mixture was stirred for 16 h at room temperature. The mixture was neutralized to pH 7 with 1 mol/L HCl (aq.). The organic solvent was removed under vacuum. The resulting mixture was diluted with water and extracted with EtOA. The organic layer was dried over anhydrous Na₂SO₄ and concentrated under vacuum. The residue was purified by Prep-HPLC followed by Chiral-Prep-HPLC, described below, to afford compounds [13a] and compound [13b]. MS (ES, m/z):$[M-1]^-=366.1$.

Chiral HPLC condition: Instrument, SHIMADZU LC-20AD; Column: lux cellulose-4, 4.6*50 mm, 3 uM; Mobile phase A, n-hexane (0.1% TFA); Mobile phase B, Ethanol; Conc. Of phase B, 15%; Flow rate, 1.0 mL/min. One of compounds [13a] and [13b] has tR: 4.76 min and the other has tR: 5.50 min.

Example 14

Synthesis of 1,1,2,2-tetrafluoro-5-((5-fluoropyridin-3-yl)oxy)-3-hydroxy-2,3-dihydro-TH-indene-4-carbonitrile-3-d

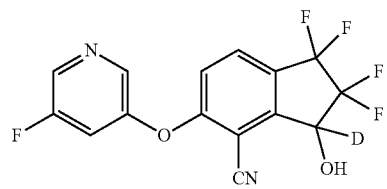 [SMILES: [2H]C1(O)c2c(ccc(Oc3cncc(F)c3)c2C#N)C(F)(F)C1(F)F]

Step 1: 1,1,2,2-tetrafluoro-5-((5-fluoropyridin-3-yl)oxy)-3-oxo-2,3-dihydro-TH-indene-4-carbonitrile

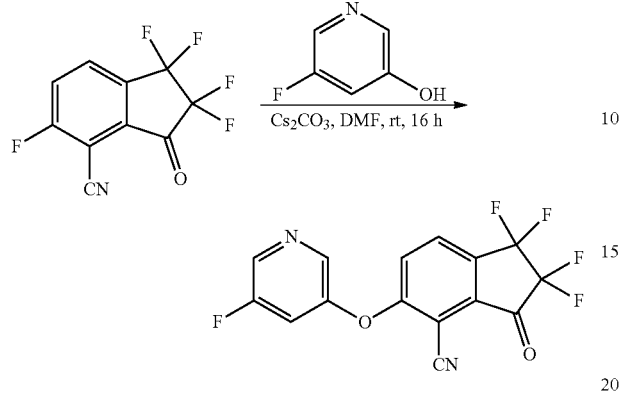

To a stirred solution of 5-fluoropyridin-3-ol (46 mg, 0.405 mmol, 1.00 equiv) and 1,1,2,2,5-pentafluoro-3-oxo-2,3-dihydro-1H-indene-4-carbonitrile (100 mg, 0.405 mmol, 1.00 equiv) in DMF (2.00 mL) was added $Cs_2CO_3$ (132 mg, 0.405 mmol, 1.00 equiv) at room temperature under nitrogen atmosphere. The resulting mixture was stirred for 16 h at room temperature under nitrogen atmosphere and then diluted with water. The resulting mixture was extracted with EtOAc and the combined organic layers were washed with brine, dried over anhydrous $Na_2SO_4$. After filtration, the filtrate was concentrated under reduced pressure and the residue was purified by Prep-TLC (PE/EtOAc 1:1) to afford the title compound (60 mg, 43.6%) as a light yellow solid.

Step 2: 1,1,2,2-tetrafluoro-5-((5-fluoropyridin-3-yl)oxy)-3-hydroxy-2,3-dihydro-1H-indene-4-carbonitrile-3-d

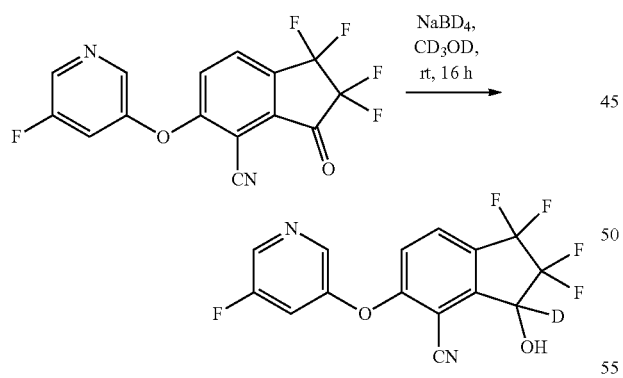

To a stirred solution of 1,1,2,2-tetrafluoro-5-((5-fluoropyridin-3-yl)oxy)-3-oxo-2,3-dihydro-1H-indene-4-carbonitrile (60 mg, 0.176 mmol, 1.00 equiv) in MeOD (1.00 mL) was added $NaBD_4$ (15 mg, 0.353 mmol, 2.00 equiv) in portions at room temperature under nitrogen atmosphere. The resulting mixture was stirred for 16 h at room temperature under nitrogen atmosphere and then quenched by water at 5° C. The mixture was neutralized to pH 7 with 1 mol/L HCl (aq.) and the resulting solution was purified by Prep-HPLC to afford the title compound (15 mg, 24.8%) as a white solid. MS (ES, m/z): $[M+1]^+=344.0$.

Example 15

Synthesis of 5-(3-cyano-5-fluorophenoxy)-1,1,2,2-tetrafluoro-3-hydroxy-3-methyl-2,3-dihydro-1H-indene-4-carbonitrile

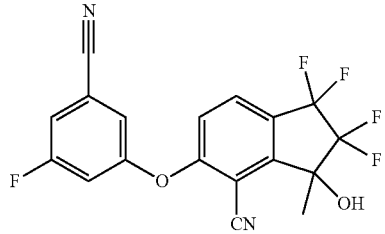 [SMILES: CC1(O)c2c(ccc(Oc3cc(F)cc(C#N)c3)c2C#N)C(F)(F)C1(F)F]

Step 1: 5-(3-cyano-5-fluorophenoxy)-1,1,2,2-tetrafluoro-3-hydroxy-3-methyl-2,3-dihydro-1H-indene-4-carbonitrile

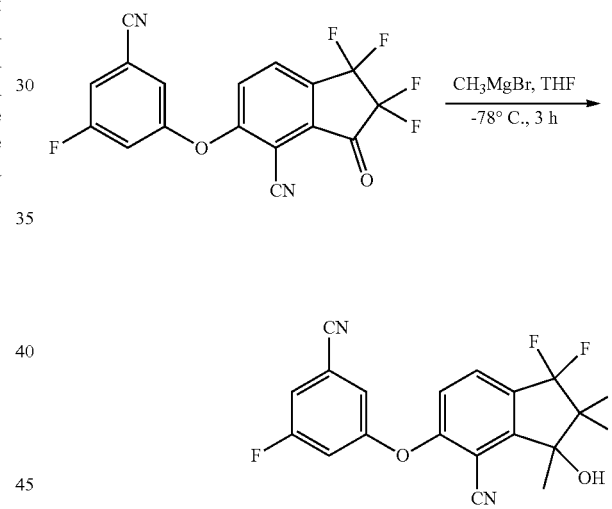

To a stirred solution of 5-(3-cyano-5-fluorophenoxy)-1,1,2,2-tetrafluoro-3-oxo-2,3-dihydro-1H-indene-4-carbonitrile (50 mg, 0.137 mmol, 1.00 equiv) in THF (2.00 mL) was added 1 mol/L $CH_3MgBr$ in THF (0.17 mL, 0.170 mmol, 1.2 equiv) dropwise at −78° C. under nitrogen atmosphere. The resulting mixture was stirred for 3 h at −78° C. under nitrogen atmosphere and then quenched by saturated aqueous $NH_4Cl$. The resulting mixture was extracted with EtOAc and the organic layer was dried over anhydrous $Na_2SO_4$ and concentrated under reduced pressure. The residue was purified by Prep-HPLC to afford the title compound (10.4 mg, 19.9%). MS (ES, m/z): $[M−1]^−=379.2$.

Example 16

Synthesis of 3-((4-bromo-1,1,2,2-tetrafluoro-3-hydroxy-3-methyl-2,3-dihydro-1H-inden-5-yl)oxy)-5-fluorobenzonitrile

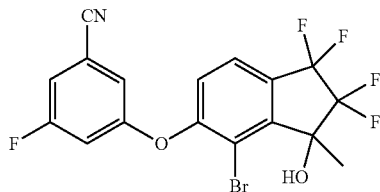 [SMILES: CC1(O)c2c(ccc(Oc3cc(F)cc(C#N)c3)c2Br)C(F)(F)C1(F)F]

Step 1: 7-bromo-2,2,3,3,6-pentafluoro-1-methyl-2,3-dihydro-1H-inden-1-ol

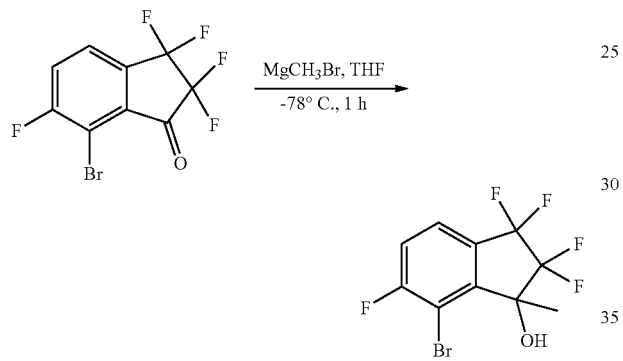

To a stirred mixture of 7-bromo-2,2,3,3,6-pentafluoro-2,3-dihydro-1H-inden-1-one (50 mg, 0.166 mmol, 1.00 equiv) in tetrahydrofuran (2 mL) was added 2.5M bromo(methyl)magnesium (0.10 mL, 0.250 mmol, 1.51 equiv) dropwise at −78° C. under nitrogen atmosphere. The resulting mixture was stirred for 1 h at −78° C. under nitrogen atmosphere. The reaction was quenched with saturated NH$_4$Cl (aq.) and extracted with EtOAc. The organic layer was dried over anhydrous Na$_2$SO$_4$ and concentrated under vacuum and the residue was purified by silica gel column chromatography, eluted with PE/EtOAc (5:1) to afford the title compound (40 mg, 76.0%).

Step 2: 3-((4-bromo-1,1,2,2-tetrafluoro-3-hydroxy-3-methyl-2,3-dihydro-1H-inden-5-yl)oxy)-5-fluorobenzo nitrile

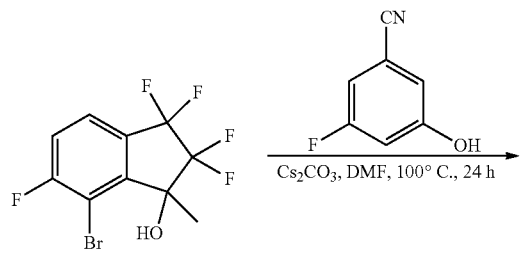

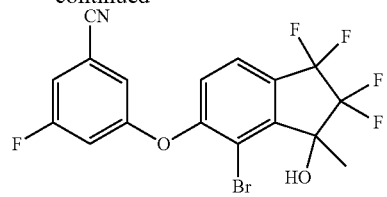

To a stirred mixture of 7-bromo-2,2,3,3,6-pentafluoro-1-methyl-2,3-dihydro-1H-inden-1-ol (30 mg, 0.095 mmol, 1.00 equiv) and 3-fluoro-5-hydroxybenzonitrile (13 mg, 0.095 mmol, 1.00 equiv) in DMF (1 mL) was added Cs$_2$CO$_3$ (31 mg, 0.095 mmol, 1.00 equiv) at room temperature. The resulting mixture was stirred for 24 h at 100° C. and then diluted with water and extracted with EtOAc. The combined organic layers were washed with water, dried over anhydrous Na$_2$SO$_4$. After filtration, the filtrate was concentrated under reduced pressure and the residue was purified by Prep-HPLC to afford the title compound (12 mg, 29.2%) as a white solid. MS (ES, m/z): [M−1]$^-$=432.1.

Example 17

Synthesis of 3-fluoro-5-((1,1,2,2-tetrafluoro-3-hydroxy-3-methyl-4-vinyl-2,3-dihydro-1H-inden-5-yl)oxy)benzonitrile

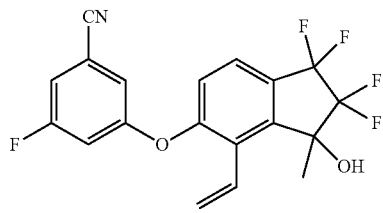 [SMILES: C=Cc1c(Oc2cc(F)cc(C#N)c2)ccc2c1C(C)(O)C(F)(F)C2(F)F]

To a stirred solution of 3-((4-bromo-1,1,2,2-tetrafluoro-3-hydroxy-3-methyl-2,3-dihydro-1H-inden-5-yl)oxy)-5-fluorobenzonitrile (20 mg, 0.048 mmol, 1.0 equiv) and 4,4,5,5-tetramethyl-2-vinyl-1,3,2-dioxaborolane (21 mg, 0.138 mmol, 3.0 equiv) in toluene (0.60 mL) were added DIEA (18 mg, 0.138 mmol, 3.0 equiv), P(t-Bu)$_3$ (2 mg, 0.009 mmol, 0.20 equiv) and Pd$_2$(dba)$_3$ (9 mg, 0.009 mmol, 0.20 equiv) at room temperature under nitrogen atmosphere. The resulting mixture was stirred for 16 h at 100° C. under nitrogen atmosphere and then diluted with H$_2$O and extracted with EtOAc. The combined organic layer was washed with H$_2$O and brine. The organic layer was concentrated under reduced pressure. The residue was purified by Prep-HPLC to afford the title compound (3.0 mg, 17.2%).

Example 18

Synthesis of 3-((4-ethyl-1,1,2,2-tetrafluoro-3-hydroxy-3-methyl-2,3-dihydro-1H-inden-5-yl)oxy)-5-fluorobenzonitrile

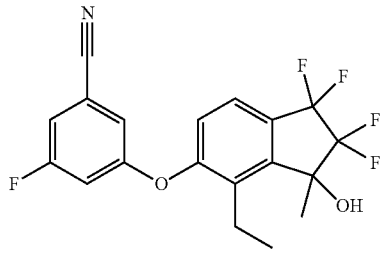 [SMILES: CCc1c(Oc2cc(F)cc(C#N)c2)ccc2c1C(C)(O)C(F)(F)C2(F)F]

To a mixture of 3-((4-bromo-1,1,2,2-tetrafluoro-3-hydroxy-3-methyl-2,3-dihydro-1H-inden-5-yl)oxy)-5-fluorobenzonitrile (30 mg, 0.069 mmol, 1.00 equiv) and Pd(dppf)Cl$_2$ (15 mg, 0.021 mmol, 0.30 equiv) in dioxane (0.30 mL) were added 1.0M diethylzinc (0.23 mL, 0.230 mmol, 3.33 equiv) at room temperature under nitrogen atmosphere. The resulting mixture was stirred for 1 h at 100° C. under nitrogen atmosphere. The resulting mixture was concentrated under reduced pressure and then diluted with water. The resulting mixture was extracted with EtOAc and the combined organic layers were washed with brine, and dried over anhydrous Na$_2$SO$_4$. After filtration, the filtrate was concentrated under reduced pressure and the residue was purified by Prep-HPLC to afford the title compound (7 mg, 26.4%). MS (ES, m/z): [M−1]$^−$=382.2.

Example 19

Synthesis of 3-((4-(difluoromethyl)-1,2,2-trifluoro-3-hydroxy-2,3-dihydro-1H-inden-5-yl)oxy)-5-fluorobenzonitrile

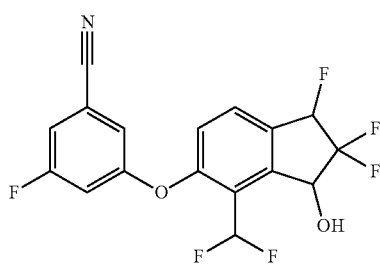

Step 1: tert-butyl 2-bromo-4-fluorobenzoate

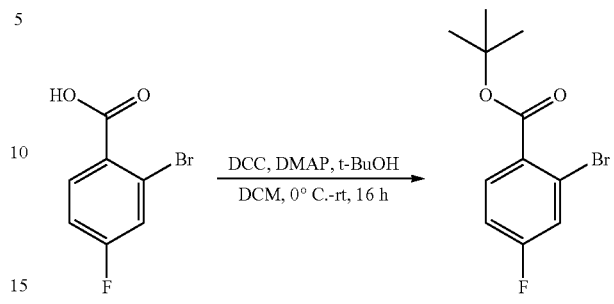

To a stirred solution of 2-bromo-4-fluorobenzoic acid (25.00 g, 114.151 mmol, 1.00 equiv), DMAP (11.16 g, 91.350 mmol, 0.80 equiv) and t-BuOH (25.38 g, 342.410 mmol, 3.00 equiv) in DCM (200.0 mL) was added DCC (25.91 g, 125.577 mmol, 1.10 equiv) in portions at 0° C. The resulting mixture was stirred for 16 h at room temperature and then filtered. The filter cake was washed with DCM and the filtrate was washed with H$_2$O and brine, and dried over anhydrous Na$_2$SO$_4$. After filtration, the filtrate was concentrated under reduced pressure and the residue was purified by silica gel column chromatography, eluted with PE/EtOAc (15:1), to afford the title compound (16.30 g, 51.9%) as colorless oil.

Step 2: tert-butyl 2-bromo-4-fluoro-3-formylbenzoate

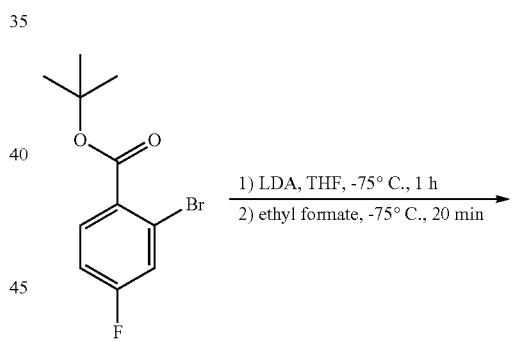

To a stirred solution of tert-butyl 2-bromo-4-fluorobenzoate (16.00 g, 58.157 mmol, 1.00 equiv) in THF (500 mL) was added 2.0M LDA (43.62 mL, 87.240 mmol, 1.50 equiv) dropwise at −78° C. under nitrogen atmosphere. The resulting mixture was stirred for 1 h at −78° C. under nitrogen atmosphere. To the above mixture was added ethyl formate (8.62 g, 116.314 mmol, 2.0 equiv) dropwise and the resulting mixture was stirred for additional 20 min at −78° C. The reaction was quenched with saturated NH₄Cl (aq.) and extracted with EtOAc. The combined organic layers were washed with water and brine, dried over anhydrous Na₂SO₄ and concentrated under reduced pressure. The residue was purified by silica gel column chromatography, eluted with PE/EtOAc (10:1) to afford (7.60 g, 43.1%) of the title compound as a yellow solid.

Step 3: tert-butyl 2-bromo-3-(difluoromethyl)-4-fluorobenzoate

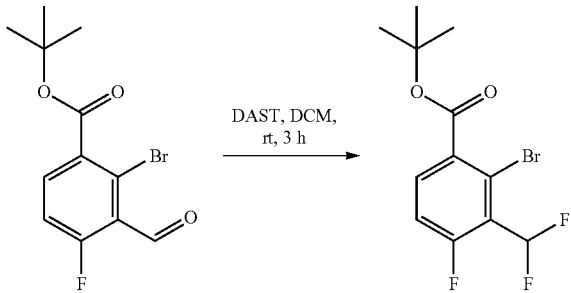 [SMILES: CC(C)(C)OC(=O)c1ccc(F)c(C=O)c1Br ; CC(C)(C)OC(=O)c1ccc(F)c(C(F)F)c1Br]

To a stirred solution of tert-butyl 2-bromo-4-fluoro-3-formylbenzoate (7.60 g, 25.072 mmol, 1.00 equiv) in DCM (150 mL) was added DAST (6.06 g, 37.608 mmol, 1.50 equiv) dropwise at 0° C. The resulting mixture was stirred for 3 h at room temperature and then quenched with saturated NH₄HCO₃ (aq.) at 0° C. The organic layer was washed with water and dried over anhydrous Na₂SO₄. After filtration, the filtrate was concentrated under reduced pressure and the residue was purified by silica gel column chromatography, eluted with PE/EtOAc (10:1) to afford the title compound (7.20 g, 88.3%) as yellow oil.

Step 4: (2-bromo-3-(difluoromethyl)-4-fluorophenyl)methanol

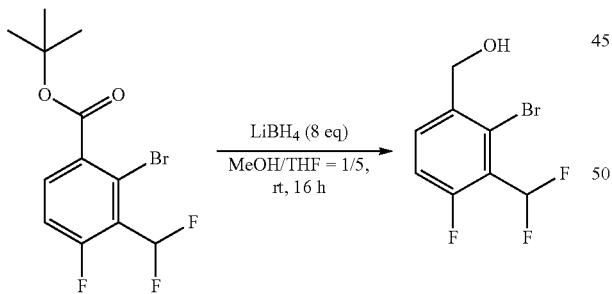

To a stirred solution of tert-butyl 2-bromo-3-(difluoromethyl)-4-fluorobenzoate (5.80 g, 17.839 mmol, 1.00 equiv) in THF (120 mL) was added LiBH₄ (3.11 g, 142.714 mmol, 8.00 equiv) in portions at 10° C. To the above mixture was added MeOH (20 mL) dropwise at 10° C. The resulting mixture was stirred for 16 h at room temperature under nitrogen atmosphere and then quenched with water at 0° C. The resulting mixture was extracted with EtOAc and the combined organic layers were washed with water, and dried over anhydrous Na₂SO₄. After filtration, the filtrate was concentrated under reduced pressure to give the title compound (4.30 g, 94.5%) as an off-white solid. The product was used directly in next step without further purification.

Step 5: 2-bromo-3-(difluoromethyl)-4-fluorobenzaldehyde

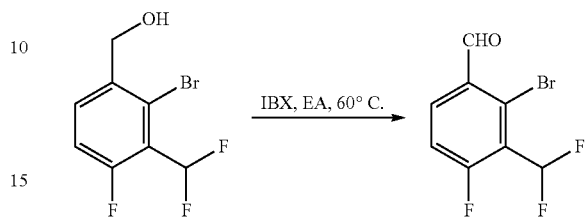

Into a 250 mL round-bottom flask were added (2-bromo-3-(difluoromethyl)-4-fluoro-phenyl)methanol (4.30 g, 16.470 mmol, 1.00 equiv), EA (100 mL) and IBX (9.44 g, 33.712 mmol, 2.00 equiv) at room temperature. The resulting mixture was stirred for 16 h at 60° C. under nitrogen atmosphere and then filtered. The filter cake was washed with EtOAc and the filtrate was concentrated under reduced pressure. The residue was purified by silica gel column chromatography, eluted with PE/EtOAc (10:1) to afford the title compound (4.00 g, 93.8%) as a yellow solid.

Step 6: ethyl 3-(2-bromo-3-(difluoromethyl)-4-fluorophenyl)-2,2-difluoro-3-hydroxypropanoate

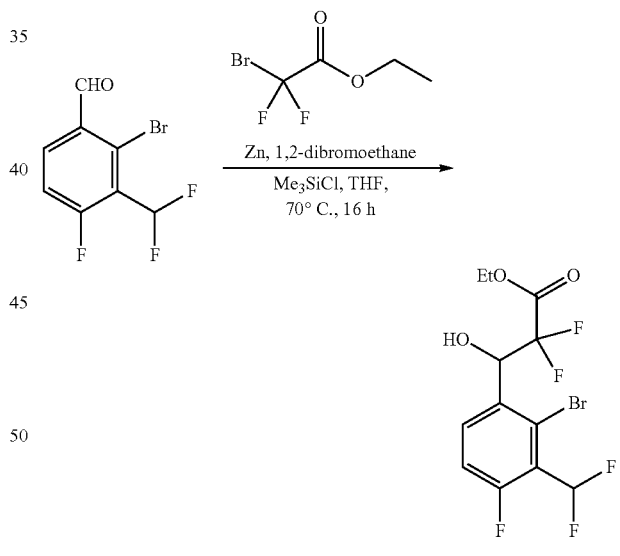

To a stirred mixture of Zn (620 mg, 9.482 mmol, 1.20 equiv), dibromoethane (30 mg, 0.158 mmol, 0.02 equiv) and chlorotrimethylsilane (86 mg, 0.791 mmol, 0.10 equiv) in THF (40 mL) was added a solution of 2-bromo-3-(difluoromethyl)-4-fluorobenzaldehyde (2.00 g, 7.905 mmol, 1.00 equiv) and ethyl 2-bromo-2,2-difluoroacetate (1.60 g, 7.883 mmol, 1.00 equiv) in THF (10 mL) dropwise at room temperature under nitrogen atmosphere. The resulting mixture was stirred for 16 h at 75° C. under nitrogen atmosphere and then filtered. The filter cake was washed with EtOAc and the filtrate was diluted with water. The resulting mixture was extracted with EtOAc and the combined organic layers were washed with brine, and dried over anhydrous Na₂SO₄. After filtration, the filtrate was concentrated under reduced pressure and the residue was purified by silica gel column chromatography, eluted with PE/EtOAc (5:1), to afford the title compound (750 mg, 25.2%) as colorless oil.

Step 7: ethyl 3-(2-bromo-3-(difluoromethyl)-4-fluorophenyl)-2,2,3-trifluoropropanoate

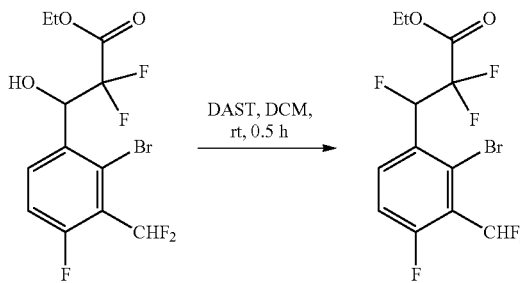

A solution of ethyl 3-(2-bromo-3-(difluoromethyl)-4-fluorophenyl)-2,2-difluoro-3-hydroxypropanoate (377 mg, 1.00 mmol, 1.00 equiv) and DAST (193 mg, 1.200 mmol, 1.20 equiv) in DCM (4 mL) was stirred for 0.5 h at room temperature under nitrogen atmosphere. The reaction was quenched with ice H₂O at 0° C. and extracted with DCM. The combined organic layers were washed with brine and dried over anhydrous Na₂SO₄. After filtration, the filtrate was concentrated under reduced pressure and the residue was purified by silica gel column chromatography, eluted with PE/EtOAc (8:1), to afford the title compound (350 mg, 92.4%) as a light yellow oil.

Step 8: 7-(difluoromethyl)-2,2,3,6-tetrafluoro-2,3-dihydro-1H-inden-1-one

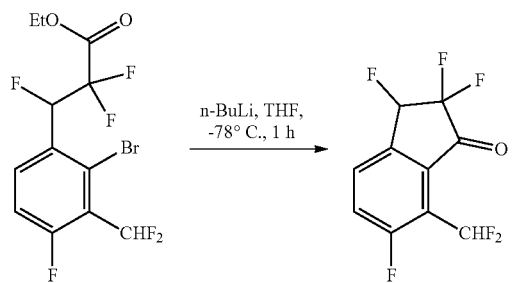 [SMILES: CCOC(=O)C(F)(F)C(F)c1ccc(F)c(C(F)F)c1Br ; O=C1c2c(ccc(F)c2C(F)F)C(F)C1(F)F]

To a stirred solution of ethyl 3-(2-bromo-3-(difluoromethyl)-4-fluorophenyl)-2,2,3-trifluoropropanoate (300 mg, 0.791 mmol, 1.00 equiv) in THF (5 mL) was added 1.0M n-BuLi (1.58 mL, 1.580 mmol, 2.00 equiv) dropwise at −78° C. under nitrogen atmosphere. The resulting mixture was stirred for 1 h at −78° C. under nitrogen atmosphere. The reaction mixture was quenched by the addition of saturated NH₄Cl (aq.) at −78° C. and then extracted with EtOAc. The combined organic layers were washed with water and brine, and dried over anhydrous Na₂SO₄.

After filtration, the filtrate was concentrated under reduced pressure and the residue was purified by silica gel column chromatography, eluted with PE/EtOAc (5:1), to afford the title compound (65 mg, 32.3%) as a yellow oil.

Step 9: 3-((4-(difluoromethyl)-1,2,2-trifluoro-3-oxo-2,3-dihydro-1H-inden-5-yl)oxy)-5-fluorobenzonitrile

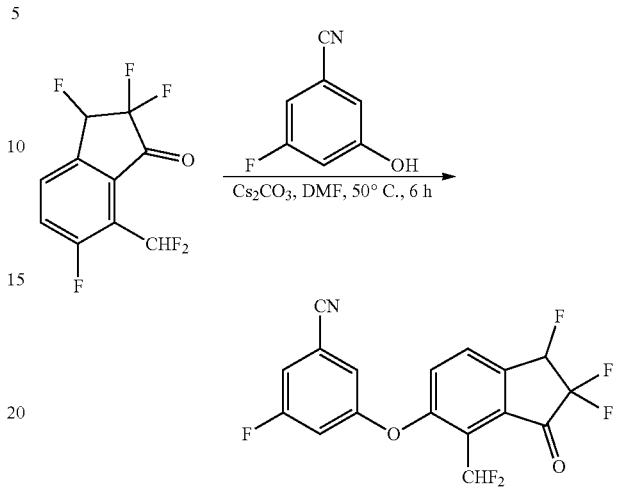

A mixture of 7-(difluoromethyl)-2,2,3,6-tetrafluoro-2,3-dihydro-1H-inden-1-one (20 mg, 0.079 mmol, 1.00 equiv), 3-fluoro-5-hydroxybenzonitrile (13 mg, 0.094 mmol, 1.20 equiv) and Cs₂CO₃ (77 mg, 0.236 mmol, 3.00 equiv) in DMF (0.40 mL) was stirred for 6 h at 50° C. The resulting mixture was diluted with water and extracted with EtOAc. The combined organic layers were washed with water and brine, and dried over anhydrous Na₂SO₄. After filtration, the filtrate was concentrated under reduced pressure. The residue was purified by Prep-TLC (PE/EtOAc=1:1) to afford the title compound (15 mg, 37.9%) as a yellow solid.

Step 10: 3-((4-(difluoromethyl)-1,2,2-trifluoro-3-hydroxy-2,3-dihydro-1H-inden-5-yl)oxy)-5-fluorobenzonitrile

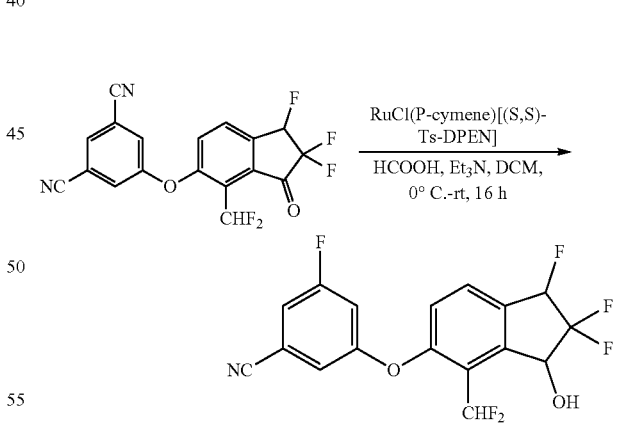

To a stirred solution of 3-((4-(difluoromethyl)-1,2,2-trifluoro-3-oxo-2,3-dihydro-1H-inden-5-yl)oxy)-5-fluorobenzonitrile (10.0 mg, 0.027 mmol, 1.00 equiv) and TEA (5.5 mg, 0.054 mmol, 2.00 equiv) in DCM (1 mL) were added formic acid (3.7 mg, 0.081 mmol, 3.00 equiv) dropwise at room temperature, followed by RuCl(P-cymene)[(S,S)-Ts-DPEN] (1.7 mg, 0.003 mmol, 0.10 equiv). The resulting mixture was stirred for 16 h at room temperature under nitrogen atmosphere and then concentrated under reduced pressure. The residue was purified by Prep-HPLC to afford the title compound (1.7 mg, 12.9%) as off-white semi-solid. MS (ES, m/z): [M−1]⁻=372.1.

Example 20

Synthesis of 3-((2-chloro-4-(difluoromethyl)-1,1,2-trifluoro-3-hydroxy-2,3-dihydro-1H-inden-5-yl)oxy)-5-fluorobenzonitrile

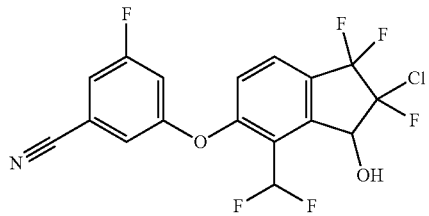 [SMILES: N#Cc1cc(F)cc(Oc2ccc3c(c2C(F)F)C(O)C(F)(Cl)C3(F)F)c1]

Step 1: ethyl 3-(2-bromo-4-fluorophenyl)-3-oxopropanoate

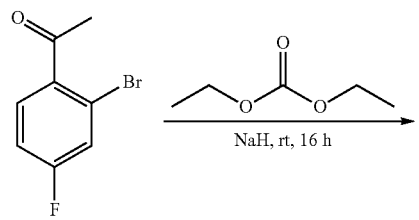

To a stirred solution of 1-(2-bromo-4-fluorophenyl)ethan-1-one (10.00 g, 46.075 mmol, 1.00 equiv) and EtOH (212 mg, 4.608 mmol, 0.10 equiv) in diethyl carbonate (60 mL) was added 60% NaH (3.69 g, 92.259 mmol, 2.00 equiv) in portions at 0° C. The resulting mixture was stirred for 16 h at room temperature and then quenched with 1 M HCl (aq.) at 0° C. The resulting mixture was extracted with EtOAc and the combined organic layers were washed with water and brine, and dried over anhydrous $Na_2SO_4$. After filtration, the filtrate was concentrated under reduced pressure and the residue was purified by silica gel column chromatography, eluted with PE/EtOAc (10:1) to afford the title compound (6.30 g, 47.3%) as a light yellow liquid.

Step 2: ethyl 3-(2-bromo-4-fluorophenyl)-2-fluoro-3-oxopropanoate

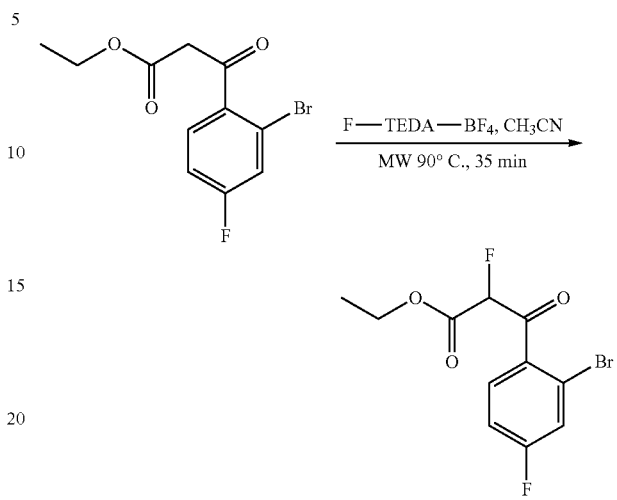

Into the microwave tube (30 mL) were added ethyl 3-(2-bromo-4-fluorophenyl)-3-oxopropanoate (6.30 g, 21.792 mmol, 1.00 equiv), $CH_3CN$ (90.0 mL) and F-TEDA-$BF_4$ (7.72 g, 21.792 mmol, 1.00 equiv) at room temperature. The resulting reaction mixture was irradiated with microwave radiation for 35 min at 90° C. The resulting mixture was concentrated under reduced pressure. The residue was purified by silica gel column chromatography, eluted with PE/EtOAc (9:1), to afford the title compound (4.50 g, 67.2%) as a light-yellow oil.

Step 3: ethyl 3-(2-bromo-4-fluorophenyl)-2-chloro-2-fluoro-3-oxopropanoate

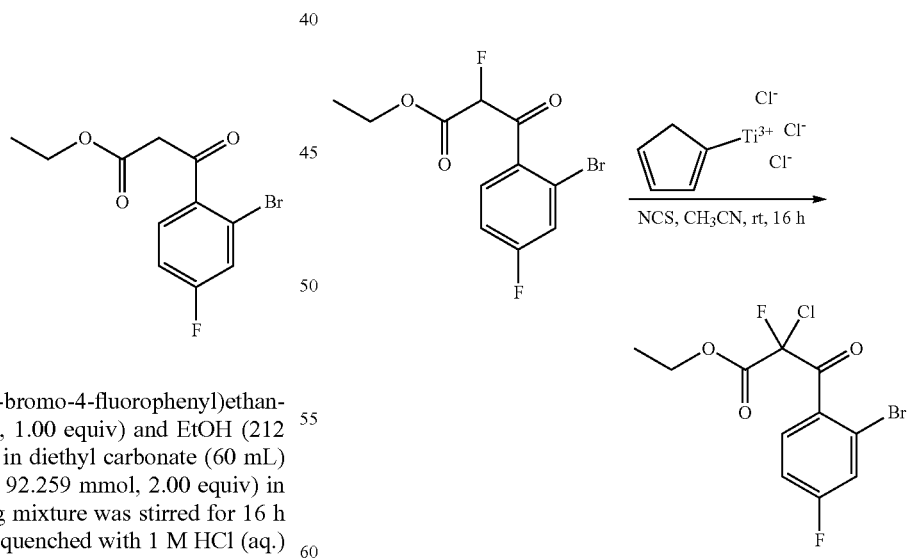

To a stirred solution of ethyl 3-(2-bromo-4-fluorophenyl)-2-fluoro-3-oxopropanoate (4.30 g, 14.002 mmol, 1.00 equiv) and NCS (2.06 g, 15.403 mmol, 1.10 equiv) in $CH_3CN$ (120 mL) were added cyclopenta-1,3-dien-1-yltitanium (IV) chloride (154 mg, 0.700 mmol, 0.045 equiv) at room temperature under nitrogen atmosphere. The resulting mixture was stirred for 16 h at room temperature under nitrogen atmosphere and then concentrated under reduced pressure. The residue was purified by silica gel column chromatography, eluted with PE/EtOAc (10:1), to afford the title compound (4.20 g, 87.8%) as a light-yellow oil.

Step 4: 3-((2-chloro-4-(difluoromethyl)-1,1,2-trifluoro-3-hydroxy-2,3-dihydro-1H-inden-5-yl)oxy)-5-fluorobenzonitrile

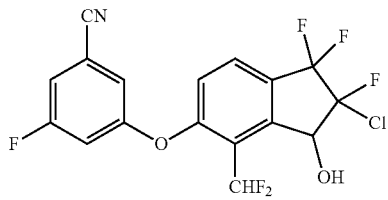 [SMILES: N#Cc1cc(F)cc(Oc2ccc3c(c2C(F)F)C(O)C(F)(Cl)C3(F)F)c1]

The title compound was synthesized by proceeding analogously as described in Example 1, Steps 4-10. MS (ES, m/z): [M−1]⁻=406.1.

Example 21

Synthesis of 3-(((2S,3S)-4-(difluoromethyl)-1,1,2-trifluoro-3-hydroxy-2,3-dihydro-1H-inden-5-yl)oxy)-5-fluorobenzonitrile [21a] and 3-(((2S,3R)-4-(difluoromethyl)-1,1,2-trifluoro-3-hydroxy-2,3-dihydro-1H-inden-5-yl)oxy)-5-fluorobenzonitrile [21b]

rac-21a
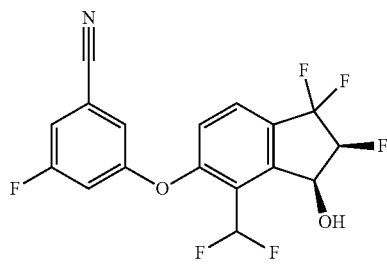

rac-21b
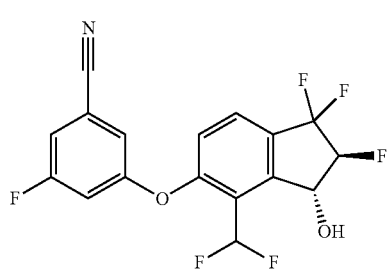

Step 1: 3-(3-bromo-2-formylphenoxy)-5-fluorobenzonitrile

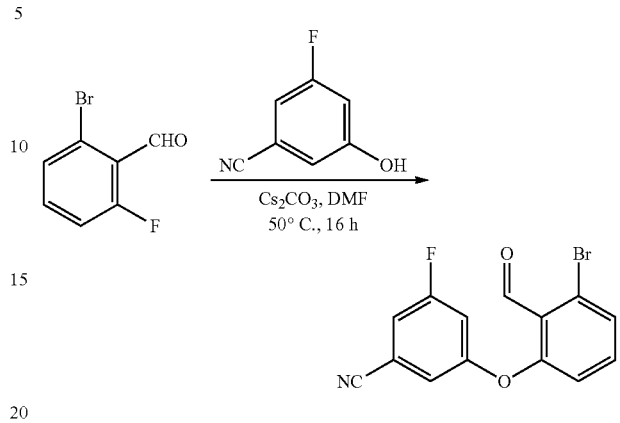

To a stirred solution of 2-bromo-6-fluorobenzaldehyde (10.00 g, 49.259 mmol, 1.00 equiv) and 3-fluoro-5-hydroxybenzonitrile (6.75 g, 49.259 mmol, 1.00 equiv) in DMF (200.0 mL) was added Cs₂CO₃ (16.05 g, 49.259 mmol, 1.00 equiv) at room temperature under nitrogen atmosphere. The resulting mixture was stirred for 16 h at 50° C. under nitrogen atmosphere and then diluted with water. The precipitated solids were collected by filtration and washed with PE to give the title compound (13 g, 82.4%) as an off-white solid.

Step 2: 3-(3-bromo-2-(difluoromethyl)phenoxy)-5-fluorobenzonitrile

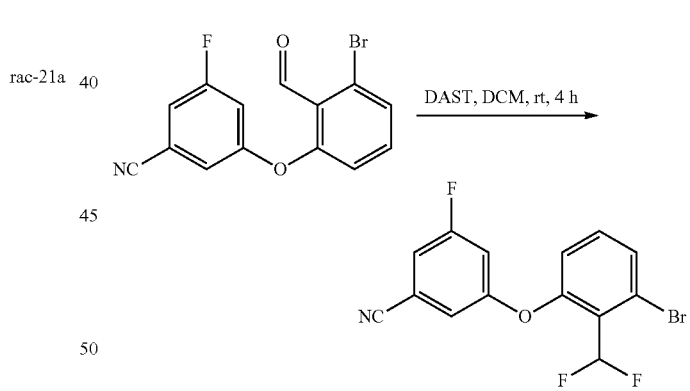

To a stirred solution of 3-(3-bromo-2-formylphenoxy)-5-fluorobenzonitrile (13.00 g, 40.610 mmol, 1.00 equiv) in DCM (200.0 mL) was added DAST (14.40 g, 89.342 mmol, 2.20 equiv) dropwise at room temperature under nitrogen atmosphere. The resulting mixture was stirred for 3 h at room temperature under nitrogen atmosphere and then quenched with water/ice at room temperature. The mixture was adjusted to pH 8 with saturated NaHCO₃(aq.) and extracted with DCM. The combined organic layers were washed with brine and dried over anhydrous Na₂SO₄. After filtration, the filtrate was concentrated under reduced pressure and the residue was purified by silica gel column chromatography, eluted with PE/EtOAc (5:1), to afford the title compound (13.0 g, 93.6%) as a light yellow semi-solid.

Step 3: ethyl 3-(3-(3-cyano-5-fluorophenoxy)-2-(difluoromethyl)phenyl)propanoate

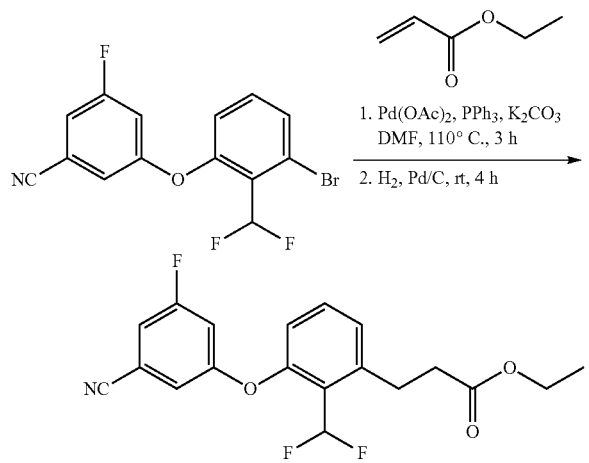

To a stirred mixture of 3-(3-bromo-2-(difluoromethyl)phenoxy)-5-fluorobenzonitrile (9.10 g, 26.599 mmol, 1.00 equiv) and ethyl acrylate (7.99 g, 79.807 mmol, 3.00 equiv) in DMF (150.0 mL) were added $K_2CO_3$ (7.35 g, 53.182 mmol, 2.00 equiv), $PPh_3$ (1.40 g, 5.320 mmol, 0.20 equiv) and $Pd(OAc)_2$ (1.20 g, 5.320 mmol, 0.20 equiv) at room temperature under nitrogen atmosphere. The resulting mixture was stirred for 3 h at 110° C. under nitrogen atmosphere. To the above mixture was added 10% Pd/C (2.65 g) and the resulting mixture was stirred for additional 4 h at room temperature under hydrogen atmosphere. The resulting mixture was filtered and the filter cake was washed with EtOAc. The filtrate was diluted with water and extracted with EtOAc and the combined organic layers were washed with water, brine and dried over anhydrous $Na_2SO_4$. After filtration, the filtrate was concentrated under reduced pressure and the residue was purified by silica gel column chromatography, eluted with PE/EtOAc (10:1), to afford the title compound (7.00 g, 77.4%) as a light yellow oil.

Step 4: 3-(3-(3-cyano-5-fluorophenoxy)-2-(difluoromethyl)phenyl)propanoic acid

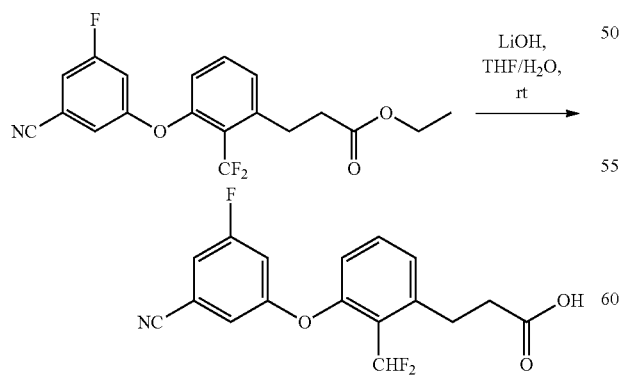

To a stirred solution of ethyl 3-(3-(3-cyano-5-fluorophenoxy)-2-(difluoromethyl)phenyl)-propanoate (7.50 g, 20.642 mmol, 1.00 equiv) in THF (160.0 mL) and $H_2O$ (40.0 mL) was added LiOH $H_2O$ (0.87 g, 20.642 mmol, 1.00 equiv) at room temperature. The resulting mixture was stirred for 4 h at room temperature and then concentrated under reduced pressure. The residue was dissolved in water and the mixture was acidified to pH 5 with 1M HCl (aq.). The resulting mixture was extracted with EtOAc and the combined organic layers were washed with brine and dried over anhydrous $Na_2SO_4$. After filtration, the filtrate was concentrated under reduced pressure to give the title compound (6.50 g, 93.9%) as an off-white solid.

Step 5: 3-((4-(dichloromethyl)-1-oxo-2,3-dihydro-1H-inden-5-yl)oxy)-5-fluorobenzonitrile

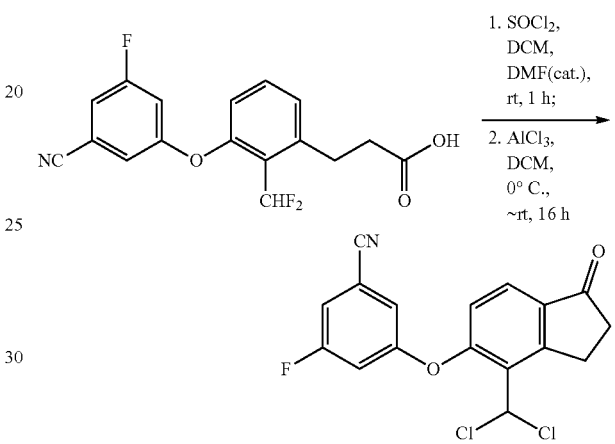

To a stirred solution of 3-(3-(3-cyano-5-fluorophenoxy)-2-(difluoromethyl)phenyl)propanoic acid (6.50 g, 19.387 mmol, 1.00 equiv) in DCM (130.0 mL) was added $SOCl_2$ (23.06 g, 193.830 mmol, 10.00 equiv) dropwise at room temperature under nitrogen atmosphere. The resulting mixture was stirred for 2 h at room temperature and then concentrated under reduced pressure. The residue was dissolved in DCM. To the above mixture was added $AlCl_3$ (15.51 g, 116.318 mmol, 6.00 equiv) in portions over 20 min at 0° C. The resulting mixture was stirred for additional 16 h at room temperature and then quenched with water at 5° C. The resulting mixture was extracted with DCM and the combined organic layers were washed with brine and dried over anhydrous $Na_2SO_4$. After filtration, the filtrate was concentrated under reduced pressure and the residue was purified by silica gel column chromatography, eluted with PE/EtOAc (3:1), to afford the title compound (5.8 g, 85.4%) as an off-white semi-solid.

Step 6: 3-fluoro-5-((4-formyl-1-oxo-2,3-dihydro-1H-inden-5-yl)oxy)benzonitrile

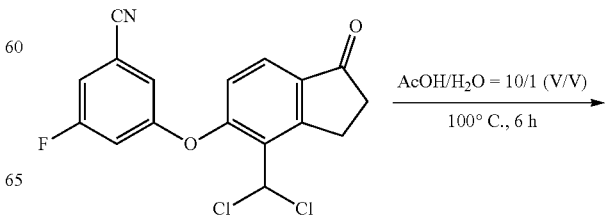

-continued

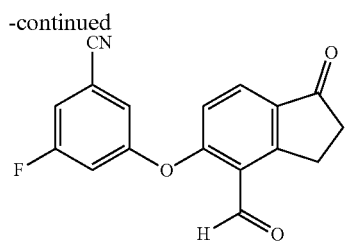

A solution of 3-((4-(dichloromethyl)-1-oxo-2,3-dihydro-1H-inden-5-yl)oxy)-5-fluorobenzonitrile (5.50 g, 15.707 mmol, 1.00 equiv) in AcOH (110.0 mL) and H$_2$O (11.0 mL) was stirred for 6 h at 100° C. under nitrogen atmosphere. The resulting mixture was concentrated under reduced pressure, and then diluted with water. The resulting mixture was extracted with EtOAc and the combined organic layers were washed with brine and dried over anhydrous Na$_2$SO$_4$. After filtration, the filtrate was concentrated under reduced pressure and the residue was purified by silica gel column chromatography, eluted with PE/EtOAc (4:1), to afford the title compound (1.03 g, 22.2%) as an off-white solid.

Step 7: 3-((4-(difluoromethyl)-1-oxo-2,3-dihydro-1H-inden-5-yl)oxy)-5-fluorobenzonitrile

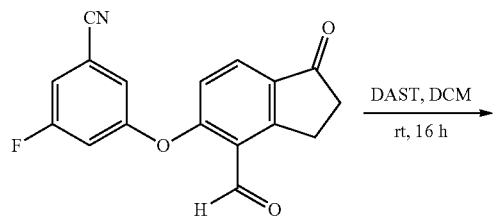

To a stirred solution of 3-fluoro-5-((4-formyl-1-oxo-2,3-dihydro-1H-inden-5-yl)oxy)-benzonitrile (1.00 g, 3.387 mmol, 1.00 equiv) in DCM (20.0 mL) was added DAST (1.2 g, 7.451 mmol, 2.20 equiv) dropwise at room temperature under nitrogen atmosphere. The resulting mixture was stirred for 16 h at room temperature under nitrogen atmosphere and then quenched with water/ice at 5° C. The mixture was neutralized to pH 7 with saturated Na$_2$CO$_3$ (aq.) and then extracted with EtOAc. The combined organic layers were washed with brine and dried over anhydrous Na$_2$SO$_4$. After filtration, the filtrate was concentrated under reduced pressure and the residue was purified by Prep-TLC (PE/EtOAc 5:1) to afford the title compound (830 mg, 77.3%) as an off-white solid.

Step 8: 3-((4-(difluoromethyl)-2-fluoro-1-oxo-2,3-dihydro-1H-inden-5-yl)oxy)-5-fluorobenzonitrile

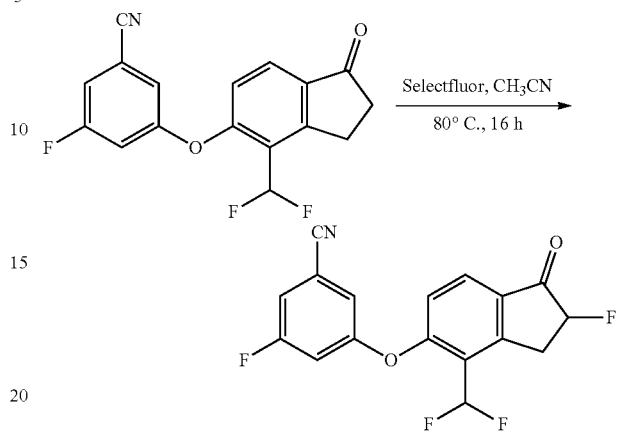

A mixture of 3-((4-(difluoromethyl)-1-oxo-2,3-dihydro-1H-inden-5-yl)oxy)-5-fluoro-benzonitrile (750 mg, 2.364 mmol, 1.00 equiv) and F-TEDA-BF$_4$ (1005 mg, 2.837 mmol, 1.20 equiv) in MeCN (15.0 mL) was stirred for 16 h at 80° C. under nitrogen atmosphere. The resulting mixture was filtered and the filter cake was washed with EtOAc. The filtrate was concentrated under reduced pressure and the residue was purified by silica gel column chromatography, eluted with PE/EtOAc (5:1), to afford the title compound (650 mg, 82.0%) as a light yellow solid.

Step 9: 3-((4-(difluoromethyl)-1,1,2-trifluoro-2,3-dihydro-1H-inden-5-yl)oxy)-5-fluorobenzonitrile

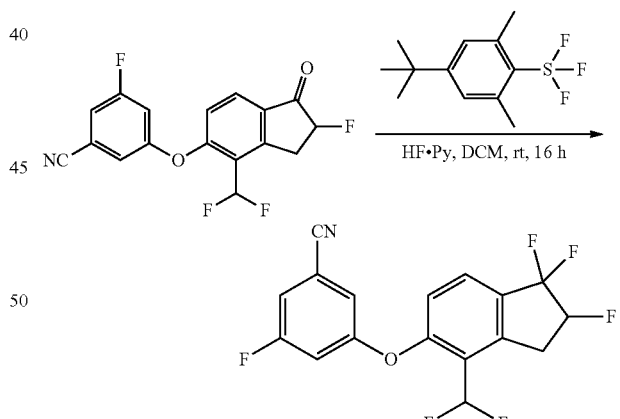

Into a 50 mL of plastic vial was added 3-((4-(difluoromethyl)-2-fluoro-1-oxo-2,3-dihydro-1H-inden-5-yl)oxy)-5-fluorobenzonitrile (800 mg, 2.386 mmol, 1.00 equiv), (4-(tert-butyl)-2,6-dimethylphenyl)trifluoro-λ$^4$-sulfane (1493 mg, 5.966 mmol, 2.50 equiv), DCM (16.0 mL), and HF-pyridine (0.86 mL, 9.545 mmol, 4.00 equiv) at room temperature. The resulting mixture was stirred for 16 h at room temperature under nitrogen atmosphere and then quenched with water/ice at room temperature. The mixture was neutralized to pH 7 with saturated Na$_2$CO$_3$ (aq.) and the resulting mixture was extracted with DCM. The combined organic layers were dried over anhydrous Na$_2$SO$_4$. After filtration, the filtrate was concentrated under reduced pressure and the residue was purified by silica gel column chromatography, eluted with PE/EtOAc (5:1), to afford the title compound (600 mg, 70.4%) as a yellow solid.

Step 10: 3-((3-bromo-4-(difluoromethyl)-1,1,2-trifluoro-2,3-dihydro-1H-inden-5-yl)oxy)-5-fluorobenzonitrile

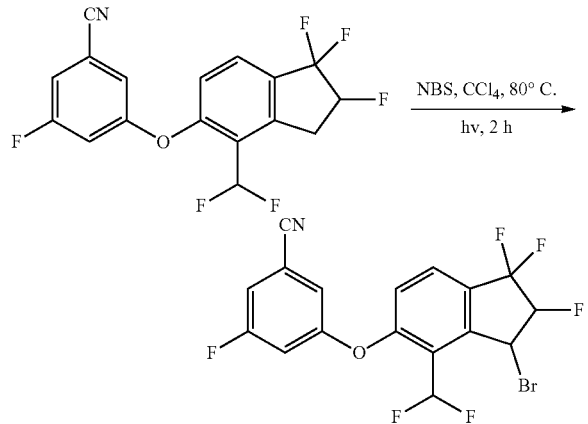

A mixture of 3-((4-(difluoromethyl)-1,1,2-trifluoro-2,3-dihydro-1H-inden-5-yl)oxy)-5-fluorobenzonitrile (120 mg, 0.336 mmol, 1.00 equiv) and NBS (149 mg, 0.840 mmol, 2.50 equiv) in CCl$_4$ (3.0 mL) was stirred and irradiated with a tungsten-filament light bulb for 2 h at 80° C. The resulting mixture was concentrated under vacuum. The residue was purified by Prep-TLC (PE/EtOAc=5:1) to afford the title compound (70 mg, 47.8%) as light yellow oil.

Step 11: rac-3-(((2S,3S)-4-(difluoromethyl)-1,1,2-trifluoro-3-hydroxy-2,3-dihydro-1H-inden-5-yl)oxy)-5-fluorobenzonitrile [21a] and rac-3-(((2S,3R)-4-(difluoromethyl)-1,1,2-trifluoro-3-hydroxy-2,3-dihydro-1H-inden-5-yl)oxy)-5-fluorobenzonitrile [21b]

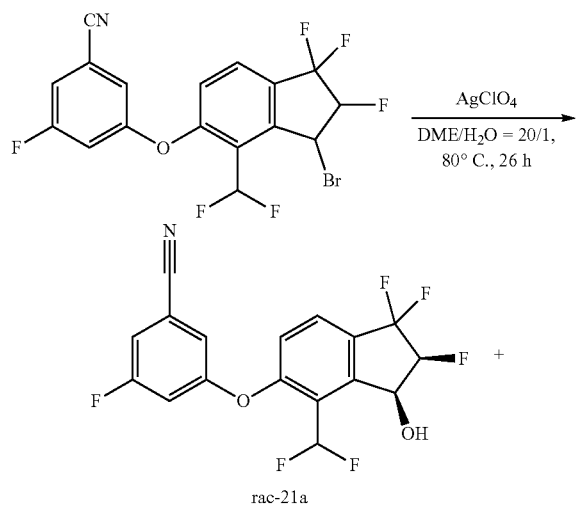

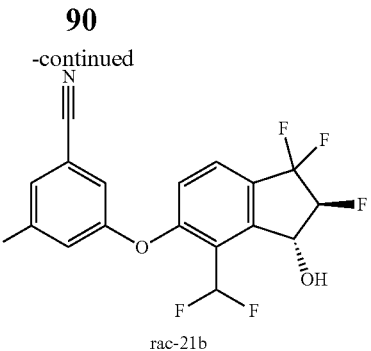

To a stirred solution of 3-((3-bromo-4-(difluoromethyl)-1,1,2-trifluoro-2,3-dihydro-1H-inden-5-yl)oxy)-5-fluorobenzonitrile (70 mg, 0.160 mmol, 1.00 equiv) in DME (1.0 mL) and H$_2$O (0.05 mL) was added AgClO$_4$ (67 mg, 0.321 mmol, 2.00 equiv) at room temperature. The resulting mixture was stirred for 26 h at 80° C. and then diluted with water. The resulting mixture was extracted with EtOAc and the combined organic layers were washed with water and dried over anhydrous Na$_2$SO$_4$. After filtration, the filtrate was concentrated under reduced pressure. The residue was purified by Prep-HPLC to afford compound [21a] and [21b]. MS (ES, m/z): [M−1]$^-$=372.1

BIOLOGICAL EXAMPLES

Example 1

VEGF ELISA Assay

The ability of the disclosed compounds to inhibit HIF-2α was measured by determining VEGF expression in 786-O cells. About 7500 786-O cells were seeded into each well of a 96-well, white, clear bottom plate (07-200-566, Fisher Scientific) with 200 ul growth medium. Four hours later, compounds were dispensed into wells by Tecan D300e digital dispenser with starting concentration of 10 uM and ½ log of dilution down to 1 nM as final concentration. Each concentration of treatment was performed in duplicate. About 20 hours later, medium was removed and fresh medium was added, followed by compounds treatment as described above. After 24 hours, cell culture medium was collected to determine VEGF concentration using an ELISA kit (R&D systems, cat #DVE00) following the manufacturer's instruction.

The EC$_{50}$ was calculated by GraphPad Prism using the dose-response-inhibition (four parameter) equation. The plate with cells was then subjected to CellTiter-Glo luminescence cell viability assay (Promega) to determine the effect of these compounds on cell numbers after the above treatment.

| Comp | Structure | EC$_{50}$ (nM) |
| --- | --- | --- |
| I-1 | 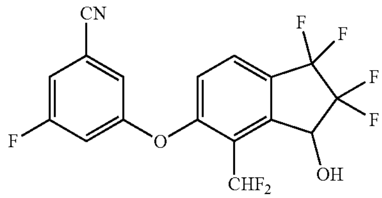 [SMILES: N#Cc1cc(F)cc(Oc2ccc3c(c2C(F)F)C(O)C(F)(F)C3(F)F)c1] | 6 |
| I-1a | | One of I-1a and I-1b is 6 and the other of I-1a and I-1b is 112. |
| I-1b | | |
| I-1c | | One of I-1c and I-1d is 4 and the other of I-1c and I-1d is 498. |
| I-1d | 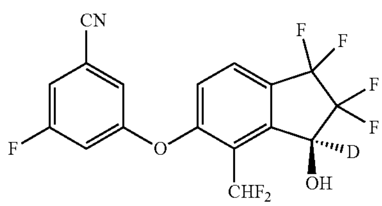 [SMILES: [2H][C@]1(O)c2c(ccc(Oc3cc(F)cc(C#N)c3)c2C(F)F)C(F)(F)C1(F)F] | |
| I-2 | 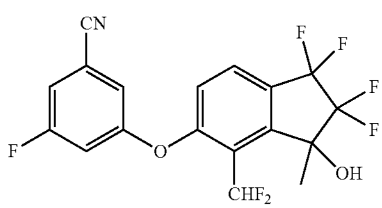 [SMILES: CC1(O)c2c(ccc(Oc3cc(F)cc(C#N)c3)c2C(F)F)C(F)(F)C1(F)F] | 770 |
| I-3 | 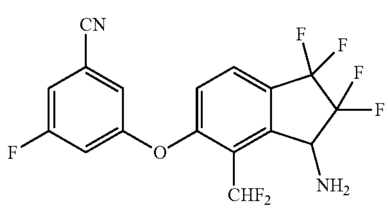 [SMILES: N#Cc1cc(F)cc(Oc2ccc3c(c2C(F)F)C(N)C(F)(F)C3(F)F)c1] | 166 |

-continued

| Comp | Structure | EC$_{50}$ (nM) |
|---|---|---|
| I-3a | 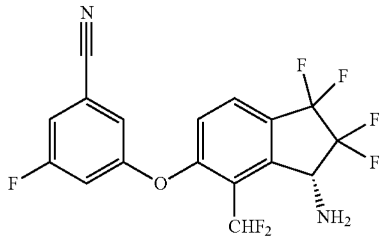 [SMILES: N#Cc1cc(F)cc(Oc2ccc3c(c2C(F)F)[C@@H](N)C(F)(F)C3(F)F)c1] | One of I-3a and I-3b is 129. |
| I-3b | 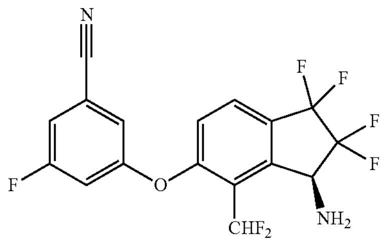 [SMILES: N#Cc1cc(F)cc(Oc2ccc3c(c2C(F)F)[C@H](N)C(F)(F)C3(F)F)c1] | |
| I-4 | 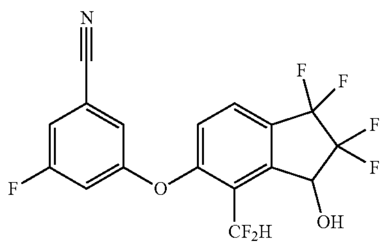 [SMILES: N#Cc1cc(F)cc(Oc2ccc3c(c2C(F)F)C(O)C(F)(F)C3(F)F)c1] | 4 |
| I-5 | 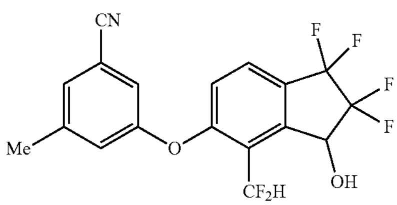 [SMILES: Cc1cc(C#N)cc(Oc2ccc3c(c2C(F)F)C(O)C(F)(F)C3(F)F)c1] | 67 |
| I-6 | 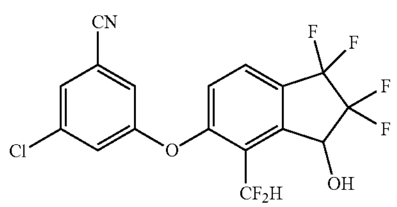 | 27 |
| I-7 | 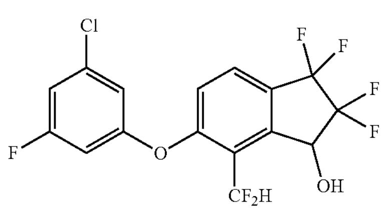 [SMILES: OC1c2c(ccc(Oc3cc(F)cc(Cl)c3)c2C(F)F)C(F)(F)C1(F)F] | 8 |
| I-8 | 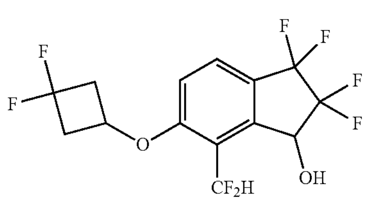 [SMILES: OC1c2c(ccc(OC3CC(F)(F)C3)c2C(F)F)C(F)(F)C1(F)F] | 105 |

-continued

| Comp | Structure | EC$_{50}$ (nM) |
|---|---|---|
| I-9 | 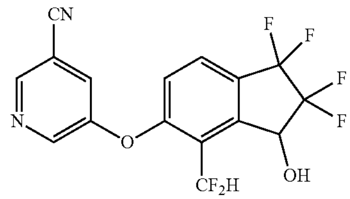 [SMILES: N#Cc1cncc(Oc2ccc3c(c2C(F)F)C(O)C(F)(F)C3(F)F)c1] | 147 |
| I-10 | 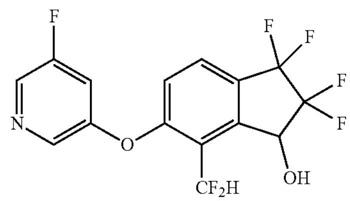 | 54 |
| I-11a | 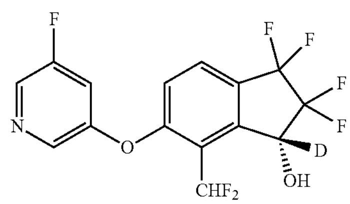 [SMILES: [2H][C@@]1(O)c2c(ccc(Oc3cncc(F)c3)c2C(F)F)C(F)(F)C1(F)F] | One of I-11a and I-11b is 28 and the other of I-11a and I-11b is 4846. |
| I-11b | 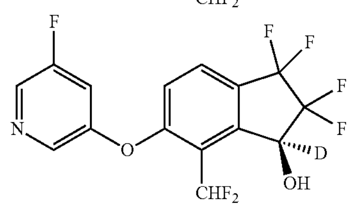 | |
| I-12a | 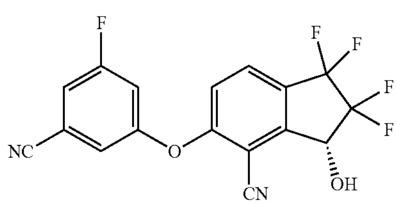 [SMILES: N#Cc1cc(F)cc(Oc2ccc3c(c2C#N)[C@@H](O)C(F)(F)C3(F)F)c1] | One of I-12a and I-12b is 16 and the other of I-12a and I-12b is 374. |
| I-12b | 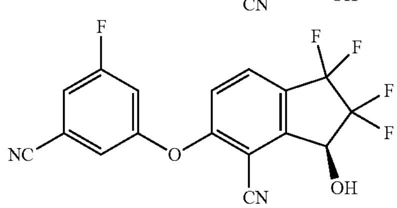 | |
| I-13b | 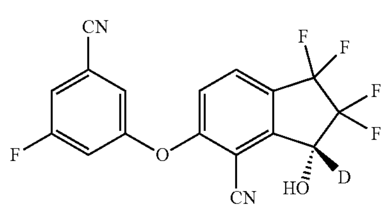 [SMILES: [2H][C@@]1(O)c2c(ccc(Oc3cc(F)cc(C#N)c3)c2C#N)C(F)(F)C1(F)F] | 12 |
| I-13a | 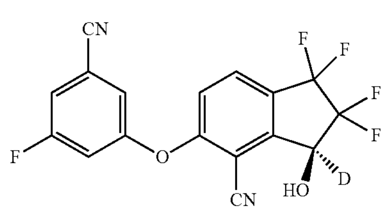 [SMILES: [2H][C@]1(O)c2c(ccc(Oc3cc(F)cc(C#N)c3)c2C#N)C(F)(F)C1(F)F] | 464 |

-continued

| Comp | Structure | EC$_{50}$ (nM) |
|---|---|---|
| I-14 | 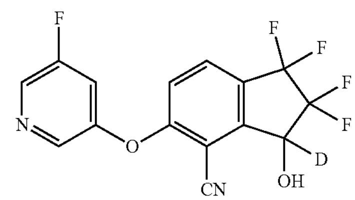 [SMILES: [2H]C1(O)c2c(ccc(Oc3cncc(F)c3)c2C#N)C(F)(F)C1(F)F] | 183 |
| I-15 | 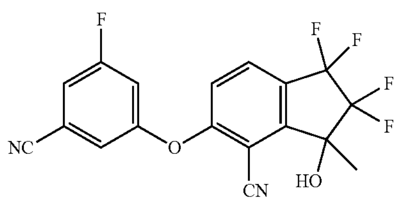 [SMILES: CC1(O)c2c(ccc(Oc3cc(F)cc(C#N)c3)c2C#N)C(F)(F)C1(F)F] | 287 |
| I-16 | 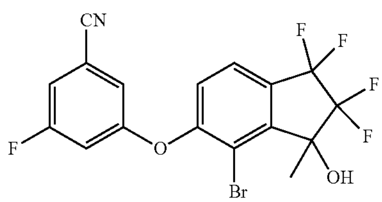 [SMILES: CC1(O)c2c(ccc(Oc3cc(F)cc(C#N)c3)c2Br)C(F)(F)C1(F)F] | 2073 |
| I-17 | 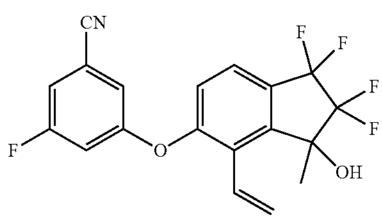 [SMILES: C=Cc1c(Oc2cc(F)cc(C#N)c2)ccc2c1C(C)(O)C(F)(F)C2(F)F] | 5769 |
| I-18 | 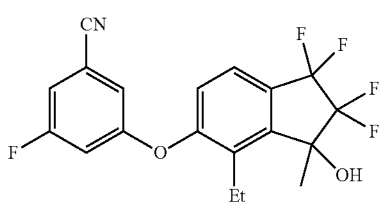 [SMILES: CCc1c(Oc2cc(F)cc(C#N)c2)ccc2c1C(C)(O)C(F)(F)C2(F)F] | 2496 |
| I-19 | 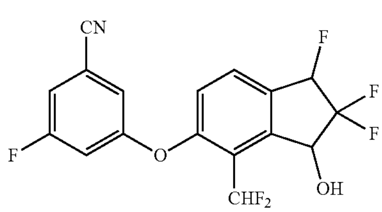 | 151 |
| I-20 | 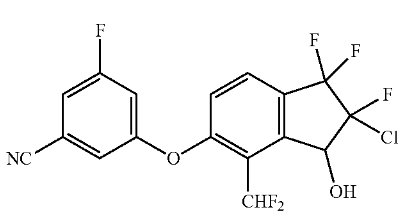 [SMILES: N#Cc1cc(F)cc(Oc2ccc3c(c2C(F)F)C(O)C(F)(Cl)C3(F)F)c1] | 20 |

| Comp | Structure | EC$_{50}$ (nM) |
| --- | --- | --- |
| I-21a | rac- | One of I-21a and I-21b is 34 and the other of I-21a and I-21b is 117. |
| I-21b | Rac- | |

FORMULATION EXAMPLES

The following are representative pharmaceutical formulations containing a compound Formula (I) or (I'), or a pharmaceutically acceptable salt thereof.

Tablet Formulation

The following ingredients are mixed intimately and pressed into single scored tablets.

| Ingredient | Quantity per tablet (mg) |
| --- | --- |
| compound of Formula (I) or (I') | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule (mg) |
| --- | --- |
| compound of Formula (I) or (I') | 200 |
| lactose spray dried | 148 |
| magnesium stearate | 2 |

Injectable Formulation

Compound of Formula (I) or (I') (e.g., compound 1) in 2% HPMC, 1% Tween 80 in DI water, pH 2.2 with MSA, q.s. to at least 20 mg/mL

Inhalation Composition

To prepare a pharmaceutical composition for inhalation delivery, 20 mg of a compound of Formula (I) or (I') is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound of Formula (I) or (I') is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound of Formula (I) or (I') is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound of Formula (I) or (I') is mixed with 30 mL of a 0.05M phosphate buffer solution (pH 4.4). The solution is placed in a nasal administrator designed to deliver 100 l of spray for each application.

What is claimed:

1. A compound of Formula (I):

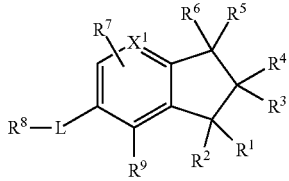
(I)

wherein:
X¹ is CH or N;
R¹ is hydroxy, amino, —OP(O)(OH)$_2$, -OCH$_2$OP(O)(OH)$_2$, -OCOR$^{10}$, -OCOOR$^{11}$, -OCONR$^{12}$R$^{13}$, -OCHR$^{14}$OCOR$^{15}$ or -OCHR$^{14}$OCOOR$^{15}$ where R$^{10}$, R$^{11}$, and R$^{15}$ are independently alkyl or alkyl substituted with amino, carboxy or hydroxy, R$^{12}$ and R$^{13}$ are independently alkyl or alkyl substituted with amino, carboxy or hydroxy or R$^{12}$ and R$^{13}$ together with the nitrogen atom to which they are attached form optionally substituted heterocyclyl, and R$^{14}$ is hydrogen, alkyl, or haloalkyl;
R² is hydrogen, deuterium, alkyl, haloalkyl, alkynyl, or alkenyl;
R³ and R⁴ are independently hydrogen, deuterium, alkyl, cycloalkyl, halo, haloalkyl, hydroxyalkyl, or alkoxyalkyl; provided that one of R³ and R⁴ is halo; or
R³ and R⁴ together with the carbon to which they are attached form oxo, cycloalkylene, or 4 to 6 membered optionally substituted heterocyclylene;
R⁵ is hydrogen, deuterium, alkyl, halo, haloalkyl, hydroxy, or alkoxy;
R⁶ is hydrogen, deuterium, alkyl, cycloalkyl, or halo; or
R⁵ and R⁶ together with the carbon to which they are attached form cycloalkylene or 4 to 6 membered optionally substituted heterocyclylene provided R¹ and R² and R³ and R⁴ together with the carbon to which they are attached do not form cycloalkylene or optionally substituted 4 to 6 membered heterocyclylene simultaneously;
R⁷ is hydrogen, deuterium, alkyl, alkoxy, cyano, halo, haloalkyl, or haloalkoxy;
L is a bond, S, SO, SO$_2$, O, CO, or NR$^{16}$ where R$^{16}$ is hydrogen or alkyl;
R⁸ is cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with R$^a$, R$^b$, and/or R$^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl; and
R⁹ is haloalkyl; or
a pharmaceutically acceptable salt thereof.

2. The compound of claim 1, or a pharmaceutically acceptable salt thereof, having the structure of formula (IIa) or (IIb):

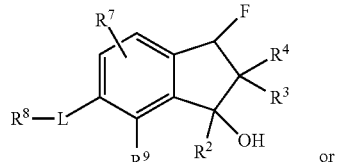
(IIa)

or

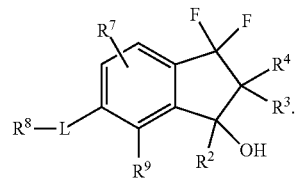
(IIb)

3. The compound of claim 1, or a pharmaceutically acceptable salt thereof, having the structure of formula (IVa):

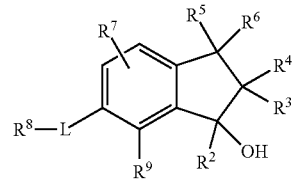
(IVa)

where R⁵ and R⁶ together with the carbon to which they are attached form cyclopropylene, cyclobutylene or cyclopentylene, each ring optionally substituted with one or two fluoro.

4. The compound of claim 1, or a pharmaceutically acceptable salt thereof, having the structure of formula (VIa) or (VIb):

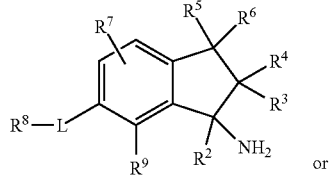
(VIa)

or

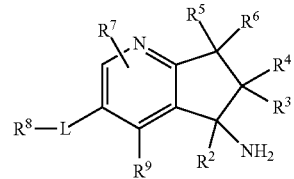
(VIb)

where R⁵ and R⁶ together with the carbon to which they are attached form cycloalkylene.

5. The compound of claim 1, or a pharmaceutically acceptable salt thereof, having the structure of formula (VIIa) or (VIIb):

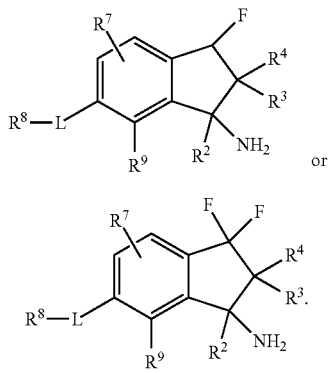

(VIIa)

(VIIb)

6. The compound of claim 2, or a pharmaceutically acceptable salt thereof, wherein R³ is fluoro.

7. The compound of claim 2, or a pharmaceutically acceptable salt thereof, where R³ and R⁴ are fluoro.

8. The compound of claim 19, or a pharmaceutically acceptable salt thereof, wherein L is O, S, SO, SO₂, or NH.

9. The compound of claim 8, or a pharmaceutically acceptable salt thereof, wherein L is O.

10. The compound of claim 9, or a pharmaceutically acceptable salt thereof, wherein R⁹ is trifluoromethyl or difluoromethyl.

11. The compound of claim 6, or a pharmaceutically acceptable salt thereof, wherein R⁹ is trifluoromethyl or difluoromethyl.

12. The compound of claim 10, or a pharmaceutically acceptable salt thereof, wherein R⁸ is phenyl substituted with Rᵃ, Rᵇ, and/or R⁶ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl.

13. The compound of claim 12, or a pharmaceutically acceptable salt thereof, wherein Rᵃ, Rᵇ, and R^c are independently selected from hydrogen, alkyl, alkoxy, hydroxy, halo, haloalkyl, haloalkoxy, and cyano.

14. The compound of claim 10, or a pharmaceutically acceptable salt thereof, wherein R⁸ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methylphenyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, or 3-cyano-5-difluoromethylphenyl.

15. The compound of claim 10, or a pharmaceutically acceptable salt thereof, wherein R⁸ is heteroaryl substituted with Rᵃ, Rᵇ, and/or R⁶ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl.

16. The compound of claim 15, or a pharmaceutically acceptable salt thereof, wherein R⁸ is 5- or 6-membered heteroaryl substituted with Rᵃ, Rᵇ, and/or R^c wherein Rᵃ and Rᵇ are independently selected from hydrogen, alkyl, alkoxy, hydroxy, halo, haloalkyl, haloalkyloxy, and cyano and R^c is selected from hydrogen, alkyl, halo, haloalkyl, and haloalkoxy.

17. The compound of claim 12, or a pharmaceutically acceptable salt thereof, wherein R⁷ is hydrogen, methyl, ethyl, methoxy, fluoro, trifluoromethyl or trifluoromethoxy.

18. The compound of claim 17, or a pharmaceutically acceptable salt thereof, wherein R² is hydrogen, deuterium, methyl, or ethyl.

19. The compound of claim 18, or a pharmaceutically acceptable salt thereof, wherein R² is hydrogen.

20. A pharmaceutical composition comprising a compound of claim 1, or a pharmaceutically acceptable salt thereof; and a pharmaceutically acceptable excipient.

21. A method of treating cancer selected from renal cancer, glioblastoma, neuroblastoma, paraganglioma, pheochromocytoma, pancreatic neuroendocrine tumors, liver cancer, colorectal cancer, hemangioblastomas, retinal cancers, von Hippel-Lindau disease, astrocytoma, lung cancer, non-small cell lung cancer, melanoma, breast cancer, cervical cancer, head and neck cancer, ovarian cancer, prostate cancer, and esophageal squamous cell carcinoma, inflammatory disease, liver disease, iron overload, or pulmonary disease in a patient which method comprises administering to the patient in recognized need thereof, a therapeutically effective amount of a pharmaceutical composition comprising a compound of claim 1, or a pharmaceutically acceptable salt thereof; and a pharmaceutically acceptable excipient.

22. The method of claim 21 wherein the disease is cancer selected from renal cancer, glioblastoma, neuroblastoma, paraganglioma, pheochromocytoma, pancreatic neuroendocrine tumors, liver cancer, colorectal cancer, hemangioblastomas, retinal cancers, von Hippel-Lindau disease, astrocytoma, lung cancer, non-small cell lung cancer, melanoma, breast cancer, cervical cancer, head and neck cancer, ovarian cancer, prostate cancer, and esophageal squamous cell carcinoma and the compound, or a pharmaceutically acceptable salt thereof, is further administered in combination with at least one other anticancer agent.

23. The method of claim 21 wherein the cancer is renal cancer, liver cancer, ovarian cancer, non-small cell lung cancer, or pancreatic cancer.

\* \* \* \* \*